US012765994B2

(12) United States Patent
Clarke et al.

(10) Patent No.: US 12,765,994 B2
(45) Date of Patent: Oct. 20, 2026

(54) DEVICES TO SUPPORT AND POSITION AN INTRAOCULAR LENS WITHIN THE EYE AND METHODS OF USE

(71) Applicant: Long Bridge Medical, Inc., Brisbane, CA (US)

(72) Inventors: Matthew Clarke, Brisbane, CA (US); Ayman Naseri, Brisbane, CA (US)

(73) Assignee: Long Bridge Medical, Inc., South San Francisco, CA (US)

( * ) Notice: Subject to any disclaimer, the term of this patent is extended or adjusted under 35 U.S.C. 154(b) by 408 days.

(21) Appl. No.: 18/485,218

(22) Filed: Oct. 11, 2023

(65) Prior Publication Data

US 2024/0033073 A1 Feb. 1, 2024

Related U.S. Application Data

(63) Continuation of application No. 17/396,048, filed on Aug. 6, 2021, now Pat. No. 12,419,736, which is a (Continued)

(51) Int. Cl.

*A61F 2/16* (2006.01)
*A61F 2/14* (2006.01)

(52) U.S. Cl.

CPC .................. *A61F 2/16* (2013.01); *A61F 2/14* (2013.01); *A61F 2/15* (2015.04); (Continued)

(58) Field of Classification Search

CPC .......... A61H 1/0244; A61H 2201/1659; A61H 2201/5028; A61H 2201/5061; (Continued)

(56) References Cited

U.S. PATENT DOCUMENTS 3,673,616 A 7/1972 Fedorov et al.
3,866,249 A 2/1975 Flom
(Continued)

FOREIGN PATENT DOCUMENTS

CA 2928918 A1 3/2017
CN 2328346 Y 7/1999
(Continued)

OTHER PUBLICATIONS

Alwitry, Amir (n.d.) IC-8 pinhole IOL. 1 page. https://amaralwitry.com/about/our-procedures/premium-lenses-refractive-procedures/ic-8-pinhole-iol.
(Continued)

*Primary Examiner* — Yashita Sharma
*Assistant Examiner* — Aren Patel
(74) *Attorney, Agent, or Firm* — Mintz Levin Cohn Ferris Glovsky and Popeo, P.C.

(57) ABSTRACT

An implantable device for supporting an artificial intraocular lens in an eye having an anterior segment of a capsular bag, an iris, and a sclera. The device includes a posterior platform having an anterior-facing surface and an inner wall defining, at least in part, a central aperture. When the device is implanted in the eye, light passes through the intraocular lens and the central aperture of the posterior platform towards the retina. The device includes at least one awning positioned over the anterior-facing surface of the posterior platform forming at least one recess anterior to the posterior platform. The device is configured to be deployed in the eye posterior of the iris so that no portion of the device rests in contact with the sclera after implantation. Related tools, systems, and methods are provided.

28 Claims, 32 Drawing Sheets

Related U.S. Application Data continuation-in-part of application No. 16/988,519, filed on Aug. 7, 2020, now Pat. No. 11,759,309.

(60) Provisional application No. 63/183,488, filed on May 3, 2021, provisional application No. 63/129,448, filed on Dec. 22, 2020, provisional application No. 63/089,241, filed on Oct. 8, 2020, provisional application No. 63/063,110, filed on Aug. 7, 2020, provisional application No. 63/053,450, filed on Jul. 17, 2020, provisional application No. 63/017,423, filed on Apr. 29, 2020.

(52) U.S. Cl.
CPC ................. *A61F 2002/1681* (2013.01); *A61F 2002/1689* (2013.01); *A61F 2002/169* (2015.04); *A61F 2002/16902* (2015.04); *A61F 2002/169053* (2015.04); *A61F 2002/1696* (2015.04); *A61F 2230/0006* (2013.01)

(58) Field of Classification Search
CPC . A61H 2201/5097; B25J 9/0006; B25J 9/163; A61F 2002/047; A61F 2002/072; A61F 2002/8486; A61F 2210/0014; A61F 2250/0039
See application file for complete search history.

(56) References Cited

U.S. PATENT DOCUMENTS 3,922,728 A 12/1975 Krasnov
3,925,825 A 12/1975 Richards et al.
3,986,214 A 10/1976 Krasnov
4,014,049 A 3/1977 Richards et al.
4,073,014 A 2/1978 Poler
4,110,848 A 9/1978 Jensen
4,118,808 A 10/1978 Poler
4,168,547 A 9/1979 Konstantinov et al.
4,190,049 A 2/1980 Hager et al.
4,215,440 A 8/1980 Worst
4,242,762 A 1/1981 Tennant
4,254,511 A 3/1981 Chase et al.
4,262,370 A 4/1981 Hartstein
4,298,996 A 11/1981 Barnet
4,316,291 A 2/1982 Severin
4,429,421 A 2/1984 Levy
4,437,194 A 3/1984 Hahs
4,576,607 A 3/1986 Kelman
4,585,457 A 4/1986 Kalb
4,617,023 A 10/1986 Peyman
4,629,460 A 12/1986 Dyer
4,718,905 A 1/1988 Freeman
4,737,322 A 4/1988 Bruns et al.
4,790,847 A 12/1988 Woods
4,878,910 A 11/1989 Koziol et al.
4,932,971 A 6/1990 Kelman
5,026,396 A 6/1991 Darin
5,152,787 A 10/1992 Hamblen
5,222,981 A 6/1993 Werblin
5,258,025 A 11/1993 Fedorov et al.
5,275,624 A 1/1994 Hara et al.
5,326,347 A 7/1994 Cumming
5,336,262 A 8/1994 Chu
5,466,233 A 11/1995 Weiner et al.
5,476,512 A 12/1995 Sarfarazi
5,507,805 A 4/1996 Koeniger
5,628,795 A 5/1997 Langerman
5,628,798 A 5/1997 Eggleston et al.
5,697,973 A 12/1997 Peyman et al.
5,752,960 A 5/1998 Nallakrishnan
5,776,191 A 7/1998 Mazzocco
5,843,184 A 12/1998 Cionni
6,027,531 A 2/2000 Tassignon
6,066,171 A 5/2000 Lipshitz et al.
6,113,633 A 9/2000 Portney
6,136,026 A 10/2000 Israel
6,152,959 A 11/2000 Portney
6,228,115 B1 5/2001 Hoffmann et al.
6,261,321 B1 7/2001 Kellan
6,264,693 B1 7/2001 Ross
6,299,641 B1 10/2001 Woods
6,342,058 B1 1/2002 Portney
6,398,809 B1 6/2002 Hoffmann et al.
6,409,763 B1 6/2002 Brady
6,443,985 B1 9/2002 Woods
6,488,708 B2 12/2002 Sarfarazi
6,551,354 B1 4/2003 Ghazizadeh et al.
6,596,026 B1 7/2003 Gross et al.
6,616,691 B1 9/2003 Tran
6,616,692 B1 9/2003 Glick et al.
6,660,036 B2 12/2003 Cumming
6,685,741 B2 2/2004 Landreville et al.
6,767,363 B1 7/2004 Bandhauer et al.
6,797,004 B1 9/2004 Brady et al.
6,881,225 B2 4/2005 Okada
6,921,415 B2 7/2005 Callahan et al.
6,972,033 B2 12/2005 McNicholas
7,125,422 B2 10/2006 Woods et al.
7,223,288 B2 5/2007 Zhang et al.
7,300,464 B2 11/2007 Tran
7,311,194 B2 12/2007 Jin et al.
7,354,451 B2 4/2008 Koch
7,416,561 B2 8/2008 Worst et al.
7,462,194 B1 12/2008 Blake
7,569,048 B2 8/2009 Brown
7,597,678 B2 10/2009 Brown
7,662,179 B2 2/2010 Sarfarazi
7,763,069 B2 7/2010 Brady et al.
7,794,498 B2 9/2010 Pinchuk
7,806,929 B2 10/2010 Brown
7,806,930 B2 10/2010 Brown
7,875,270 B2 1/2011 Zhang
7,931,686 B2 4/2011 Vaudant et al.
8,012,204 B2 9/2011 Weinschenk, III et al.
8,109,998 B2 2/2012 Cumming
8,128,693 B2 3/2012 Tran et al.
8,162,927 B2 4/2012 Peyman
8,216,305 B2 7/2012 Salvati et al.
8,273,123 B2 9/2012 Ben Nun
8,377,125 B2 2/2013 Kellan
8,551,164 B2 10/2013 Willis et al.
8,585,758 B2 11/2013 Woods
8,663,235 B2 3/2014 Tassignon
8,764,823 B2 7/2014 Cumming
8,778,022 B2 7/2014 Blum et al.
8,821,166 B2 9/2014 Akura et al.
8,852,275 B2 10/2014 Park
8,888,845 B2 11/2014 Vaquero et al.
8,900,300 B1 12/2014 Wortz
8,920,495 B2 12/2014 Mirlay
8,932,351 B2 1/2015 Dell
8,945,215 B2 2/2015 Basinger
8,956,408 B2 2/2015 Smiley et al.
9,034,035 B2 5/2015 Betser et al.
9,039,762 B2 5/2015 Hong et al.
9,072,600 B2 7/2015 Tran
9,078,744 B2 7/2015 Van Noy
9,084,673 B2 7/2015 Dell
9,095,424 B2 8/2015 Kahook et al.
9,125,736 B2 9/2015 Kahook et al.
9,198,752 B2 12/2015 Woods
9,289,287 B2 3/2016 Kahook et al.
9,326,845 B2 5/2016 Ichikawa et al.
9,333,072 B2 5/2016 Ichikawa
9,339,375 B2 5/2016 Lee et al.
9,358,103 B1 6/2016 Wortz et al.
9,364,316 B1 6/2016 Kahook et al.
9,364,318 B2 6/2016 Beer
9,387,069 B2 7/2016 Kahook et al.
9,398,949 B2 7/2016 Werblin
9,421,088 B1 8/2016 Kahook et al.
9,439,754 B2 9/2016 Wortz

(56) References Cited

U.S. PATENT DOCUMENTS

| | | | |
|---|---|---|---|
| 9,445,891 | B2 | 9/2016 | Ichikawa |
| 9,445,892 | B2 | 9/2016 | Brown |
| 9,468,523 | B2 | 10/2016 | Dell |
| 9,498,325 | B2 | 11/2016 | Salvati et al. |
| 9,504,558 | B2 | 11/2016 | Wortz et al. |
| 9,517,127 | B2 | 12/2016 | Wortz et al. |
| 9,522,060 | B2 | 12/2016 | Wortz et al. |
| 9,622,857 | B2 | 4/2017 | Coroneo |
| 9,629,711 | B2 | 4/2017 | Cumming |
| 9,681,945 | B2 | 6/2017 | Shahinpoor et al. |
| 9,681,946 | B2 | 6/2017 | Kahook et al. |
| 9,713,526 | B2 | 7/2017 | Rombach |
| 9,744,027 | B2 | 8/2017 | Jansen |
| 9,757,227 | B2 | 9/2017 | Kushlin et al. |
| 9,763,771 | B1 | 9/2017 | Wortz et al. |
| 9,877,825 | B2 | 1/2018 | Kahook et al. |
| 9,925,037 | B2 | 3/2018 | Wortz et al. |
| 9,925,040 | B2 | 3/2018 | Kahook et al. |
| 9,962,256 | B2 | 5/2018 | McCafferty |
| 10,004,591 | B2 | 6/2018 | Ichikawa |
| 10,010,405 | B2 | 7/2018 | Hayes |
| 10,080,648 | B2 | 9/2018 | Kahook et al. |
| 10,085,886 | B2 | 10/2018 | Schuele et al. |
| 10,201,415 | B2 | 2/2019 | Aharoni et al. |
| 10,271,944 | B2 | 4/2019 | Ichikawa et al. |
| 10,271,945 | B2 | 4/2019 | Wortz et al. |
| 10,286,107 | B2 | 5/2019 | Kahook et al. |
| 10,299,910 | B2 | 5/2019 | Cady |
| 10,383,721 | B2 | 8/2019 | Marcos Celestino et al. |
| 10,433,950 | B2 | 10/2019 | Shadduck |
| 10,449,036 | B2 | 10/2019 | Christie et al. |
| 10,470,873 | B2 | 11/2019 | Ichikawa et al. |
| 10,524,900 | B2 | 1/2020 | Beer |
| 10,548,713 | B2 | 2/2020 | Aharoni |
| 10,575,943 | B2 | 3/2020 | Ingram |
| 10,603,162 | B2 | 3/2020 | Wortz et al. |
| 10,765,509 | B2 | 9/2020 | Olson et al. |
| 10,799,340 | B2 | 10/2020 | Collins et al. |
| 10,973,624 | B1 | 4/2021 | Clarke et al. |
| 11,364,110 | B2 | 6/2022 | Webb |
| 11,382,736 | B2 | 7/2022 | Zacher et al. |
| 11,759,311 | B2 | 9/2023 | Whitsett |
| 11,833,029 | B2 | 12/2023 | Dudee |
| 2002/0087210 | A1 | 7/2002 | Stenger et al. |
| 2002/0103535 | A1 | 8/2002 | Portney |
| 2002/0161433 | A1 | 10/2002 | Baikoff et al. |
| 2003/0055499 | A1 | 3/2003 | Nguyen et al. |
| 2003/0158560 | A1 | 8/2003 | Portney |
| 2003/0158599 | A1 | 8/2003 | Brady et al. |
| 2003/0220652 | A1 | 11/2003 | Srael |
| 2004/0042073 | A1 | 3/2004 | Pynson |
| 2004/0064182 | A1 | 4/2004 | Kelman |
| 2004/0148022 | A1 | 7/2004 | Eggleston |
| 2004/0236422 | A1 | 11/2004 | Zhang et al. |
| 2004/0249455 | A1 | 12/2004 | Tran |
| 2005/0021138 | A1 | 1/2005 | Woods |
| 2005/0021140 | A1 | 1/2005 | Liao |
| 2005/0085907 | A1 | 4/2005 | Hanna |
| 2005/0177229 | A1 | 8/2005 | Boxer Wachler |
| 2006/0047339 | A1 | 3/2006 | Brown |
| 2006/0047340 | A1 | 3/2006 | Brown |
| 2006/0235515 | A1 | 10/2006 | Chassain |
| 2007/0027541 | A1 | 2/2007 | Aharoni et al. |
| 2007/0032868 | A1 | 2/2007 | Woods |
| 2007/0123982 | A1 | 5/2007 | Yablonski et al. |
| 2007/0162115 | A1 | 7/2007 | Hermeking |
| 2007/0260308 | A1 | 11/2007 | Tran |
| 2008/0086208 | A1 | 4/2008 | Nordan |
| 2008/0154364 | A1 | 6/2008 | Richardson et al. |
| 2009/0171458 | A1 | 7/2009 | Kellan et al. |
| 2009/0198247 | A1 | 8/2009 | Ben Nun |
| 2009/0204209 | A1 | 8/2009 | Tran |
| 2010/0030331 | A1 | 2/2010 | Zhang et al. |
| 2010/0057095 | A1 | 3/2010 | Khuray et al. |
| 2010/0094415 | A1 | 4/2010 | Bumbalough |
| 2010/0121444 | A1 | 5/2010 | Ben Nun |
| 2010/0131059 | A1 | 5/2010 | Callahan et al. |
| 2010/0152848 | A1 | 6/2010 | Williamson et al. |
| 2010/0262234 | A1 | 10/2010 | Tran et al. |
| 2011/0071628 | A1 | 3/2011 | Gross et al. |
| 2011/0295368 | A1 | 12/2011 | Betser |
| 2011/0313521 | A1 | 12/2011 | Angelopoulos |
| 2011/0313522 | A1 | 12/2011 | Hayes |
| 2011/0313523 | A1 | 12/2011 | Hayes |
| 2012/0290086 | A1 | 11/2012 | Malyugin et al. |
| 2012/0303119 | A1 | 11/2012 | Callahan et al. |
| 2012/0330415 | A1 | 12/2012 | Callahan et al. |
| 2013/0116781 | A1* | 5/2013 | Ben Nun .............. A61F 2/1651 623/6.43 |
| 2013/0190868 | A1 | 7/2013 | Kahook et al. |
| 2014/0094908 | A1 | 4/2014 | Zaldivar et al. |
| 2014/0121768 | A1 | 5/2014 | Simpson |
| 2014/0316520 | A1 | 10/2014 | Barsam et al. |
| 2014/0330375 | A1 | 11/2014 | McCafferty |
| 2014/0371851 | A1 | 12/2014 | Aharoni |
| 2014/0371852 | A1* | 12/2014 | Aharoni .................... A61F 2/14 623/6.43 |
| 2015/0025627 | A1 | 1/2015 | Christie et al. |
| 2015/0127102 | A1 | 5/2015 | Wortz |
| 2015/0202040 | A1 | 7/2015 | McCafferty |
| 2015/0265398 | A1 | 9/2015 | Hartkens et al. |
| 2015/0305857 | A1 | 10/2015 | Ichikawa |
| 2015/0366656 | A1 | 12/2015 | Wortz et al. |
| 2015/0366659 | A1 | 12/2015 | Wortz et al. |
| 2016/0000558 | A1 | 1/2016 | Honigsbaum |
| 2016/0128828 | A1 | 5/2016 | Dalvi |
| 2016/0157995 | A1 | 6/2016 | Beer |
| 2016/0184089 | A1 | 6/2016 | Dudee et al. |
| 2016/0256260 | A1 | 9/2016 | Wortz et al. |
| 2016/0256262 | A1 | 9/2016 | Wortz et al. |
| 2016/0256267 | A1 | 9/2016 | Wortz et al. |
| 2016/0256315 | A1 | 9/2016 | Wortz et al. |
| 2016/0331520 | A1 | 11/2016 | Beer |
| 2016/0338825 | A1 | 11/2016 | Wortz et al. |
| 2016/0361156 | A1 | 12/2016 | Brown |
| 2017/0020662 | A1 | 1/2017 | Shadduck |
| 2017/0049560 | A1 | 2/2017 | Cherne |
| 2017/0258575 | A1 | 9/2017 | Wortz et al. |
| 2017/0319332 | A1 | 11/2017 | Kahook et al. |
| 2017/0348095 | A1 | 12/2017 | Wortz et al. |
| 2018/0014928 | A1 | 1/2018 | Kahook et al. |
| 2018/0110613 | A1 | 4/2018 | Wortz et al. |
| 2018/0263757 | A1* | 9/2018 | Wanders ................. A61F 9/007 |
| 2018/0271642 | A1 | 9/2018 | Wortz et al. |
| 2018/0338825 | A1 | 11/2018 | Aharoni |
| 2019/0015197 | A1 | 1/2019 | Wortz et al. |
| 2019/0076236 | A1 | 3/2019 | Scharioth et al. |
| 2019/0076239 | A1 | 3/2019 | Wortz et al. |
| 2019/0083235 | A1 | 3/2019 | Wortz |
| 2019/0091009 | A1 | 3/2019 | Collins et al. |
| 2019/0125944 | A1 | 5/2019 | Wiley |
| 2019/0133754 | A1 | 5/2019 | Dalvi |
| 2019/0151079 | A1 | 5/2019 | Zaldivar |
| 2019/0223998 | A1 | 7/2019 | de Juan, Jr et al. |
| 2019/0254809 | A1 | 8/2019 | Dworschak et al. |
| 2019/0269499 | A1 | 9/2019 | Ellis |
| 2019/0269500 | A1* | 9/2019 | de Juan, Jr. ........... A61F 2/1618 |
| 2019/0343621 | A1 | 11/2019 | Wortz et al. |
| 2019/0380828 | A1 | 12/2019 | Wortz |
| 2020/0000575 | A1* | 1/2020 | Kojima ................. A61F 2/1694 |
| 2020/0022840 | A1 | 1/2020 | Kahook et al. |
| 2020/0121446 | A1 | 4/2020 | Cady |
| 2020/0253721 | A1 | 8/2020 | Cuevas et al. |
| 2020/0276011 | A1 | 9/2020 | Akura |
| 2020/0323626 | A1 | 10/2020 | Akinay et al. |
| 2021/0137674 | A1 | 5/2021 | Webb |
| 2021/0315687 | A1* | 10/2021 | Brodie ...................... A61F 2/16 |
| 2021/0338416 | A1 | 11/2021 | Clarke et al. |
| 2021/0338417 | A1 | 11/2021 | Clarke et al. |
| 2021/0353406 | A1 | 11/2021 | Brodie et al. |
| 2022/0000605 | A1 | 1/2022 | Clarke et al. |
| 2022/0079744 | A1 | 3/2022 | Arrieta |
| 2022/0211487 | A1 | 7/2022 | Clarke et al. |
| 2022/0362010 | A1 | 11/2022 | Akura |

(56) References Cited

U.S. PATENT DOCUMENTS

| | | | |
|---|---|---|---|
| 2023/0031555 A1 | 2/2023 | Wortz et al. | |
| 2023/0127407 A1 | 4/2023 | So | |
| 2024/0058115 A1 | 2/2024 | Kim et al. | |

FOREIGN PATENT DOCUMENTS

| | | | |
|---|---|---|---|
| CN | 101031257 | A | 9/2007 |
| CN | 101325925 | A | 12/2008 |
| CN | 102090942 | A | 6/2011 |
| CN | 102090946 | A | 6/2011 |
| CN | 102970942 | A | 3/2013 |
| CN | 204698755 | U | 10/2015 |
| CN | 110811924 | A | 2/2020 |
| DE | 20 2016 105 208 | U1 | 11/2016 |
| DE | 10 2019 115 408 | B3 | 9/2020 |
| EP | 0 106 488 | A1 | 4/1984 |
| EP | 0 346 245 | A1 | 12/1989 |
| EP | 0 089 335 | B2 | 3/1993 |
| EP | 0 931 521 | A1 | 7/1999 |
| EP | 1037572 | A1 | 9/2000 |
| EP | 1 138 282 | A1 | 10/2001 |
| EP | 1 341 485 | B1 | 11/2006 |
| EP | 2422746 | A1 | 2/2012 |
| EP | 3 061 420 | A1 | 8/2016 |
| EP | 3 158 974 | A1 | 4/2017 |
| EP | 2 117 465 | B1 | 7/2017 |
| EP | 3 171 821 | B1 | 3/2020 |
| EP | 3700466 | A1 | 9/2020 |
| FR | 2997624 | A1 | 5/2014 |
| FR | 3 033 694 | A1 | 9/2016 |
| GB | 124500 | A | 4/1919 |
| IT | 102014902224032 | A1 | 7/2015 |
| JP | 2006-525824 | A | 11/2006 |
| JP | 4892156 | B2 | 3/2012 |
| JP | 2013123616 | A | 6/2013 |
| JP | 5383782 | B2 | 1/2014 |
| JP | 2014090772 | A | 5/2014 |
| JP | 2015-223341 | A | 12/2015 |
| JP | 2019-063534 | A | 4/2019 |
| KR | 20030051903 | A | 6/2003 |
| KR | 10-2011-0075018 | A | 7/2011 |
| KR | 10-1555298 | B1 | 9/2015 |
| KR | 2016-0010428 | A | 1/2016 |
| RU | 2132667 | C1 | 7/1999 |
| RU | 86462 | U1 | 9/2009 |
| RU | 2367380 | C2 | 9/2009 |
| RU | 2440076 | C1 | 1/2012 |
| TW | 201630576 | A | 9/2016 |
| WO | WO-99/56670 | A1 | 11/1999 |
| WO | WO-00/30566 | A1 | 6/2000 |
| WO | WO-2006/103674 | A2 | 10/2006 |
| WO | WO-2007/005893 | A2 | 1/2007 |
| WO | WO-2008/077795 | A2 | 7/2008 |
| WO | WO-2008/108525 | A1 | 9/2008 |
| WO | WO-2010/091420 | A1 | 8/2010 |
| WO | WO-2011/101310 | A1 | 8/2011 |
| WO | WO-2013/112589 | A1 | 8/2013 |
| WO | WO-2014/197170 | A1 | 12/2014 |
| WO | WO-2015/026226 | A1 | 2/2015 |
| WO | WO-2016/071755 | A1 | 5/2016 |
| WO | WO-2016/159910 | A1 | 10/2016 |
| WO | WO-2016/182520 | A1 | 11/2016 |
| WO | WO-2017/212352 | A1 | 12/2017 |
| WO | WO-2019/050925 | A1 | 3/2019 |
| WO | WO-2019/094768 | A1 | 5/2019 |
| WO | WO-2019/097099 | A1 | 5/2019 |
| WO | WO-2019/106011 | A1 | 6/2019 |
| WO | WO-2019/208746 | A1 | 10/2019 |
| WO | WO-2019/235912 | A1 | 12/2019 |
| WO | WO-2020/086312 | A1 | 4/2020 |
| WO | WO-2020/086631 | A1 | 4/2020 |
| WO | WO-2020/086312 | A8 | 7/2020 |

OTHER PUBLICATIONS

Can, E. (2018). "Flapless and sutureless intrascleral fixation of posterior chamber intraocular lens for correction of aphakia." Journal of Cataract and Refractive Surgery, 44(8), 929-931.

Entokey. (2017, Nov. 21, 2017). Intraocular Lens Implantation in the Capsular Bag and Posterior Capsulotomy Techniques. Retrieved Sep. 16, 2024, from https://entokey.com/intraocular-lens-implantation-in-the-capsular-bag-and-posterior-capsulotomy-techniques/ 4 pages.

Gabor, S.G. et al. (2007). "Sutureless intrascleral posterior chamber intraocular lens fixation." Journal of Cataract and Refractive Surgery, 33(11), 1851-1854.

Hu, Z. X. et al. (2018). "Sutureless Intrascleral Haptic-Hook Lens Implantation Using 25-Gauge Trocars." Journal of Ophthalmology, 2018, 9250425. 5 pages.

Omega Ophthalmics. (n.d.) The Gemini Refractive Capsule™ Revolutionary, Not Evolutionary. 1 page. https://www.omegaophthalmics.com/video/.

Schaaf, Tracy. (Oct. 23, 2018). 'In MedTech History'—Ophthalmic Implants—Part 2. MyStrategist. 3 pages. https://www.mystrategist.com/blog/article/ophthalmic-part-2.

U.S. Appl. No. 17/284,578, filed Apr. 12, 2021, US 20210315687.

U.S. Appl. No. 17/396,048, filed Aug. 6, 2021, US202200000605.

U.S. Appl. No. 17/576,573, filed Jan. 14, 2022, US 20220211487.

U.S. Appl. No. 18/369,693, filed Sep. 18, 2023, US 20240074846.

U.S. Appl. No. 18/369,694, filed Sep. 18, 2023, US 20240074847.

U.S. Appl. No. 18/485,214, filed Oct. 11, 2023, US 20240033072.

U.S. Appl. No. 18/511,340, filed Nov. 16, 2023, US 20240180691.

U.S. Appl. No. 18/615,908, filed Mar. 25, 2024, US 20240225817.

PCT/US2023/79993, Nov. 16, 2023, WO 2024/107942.

U.S. Appl. No. 17/190,169, filed Mar. 2, 2021, US 20210338417.

U.S. Appl. No. 17/284,561, filed Apr. 12, 2021, US 20210353406.

U.S. Appl. No. 17/396,048, filed Aug. 6, 2021, US 20220000605.

Carlevale, C., et al. (Nov. 15, 2018), "New IOL dedicated for scleral fixation," Ocular Surgery News. Web. Nov. 2, 2020. 4 pages. https://www.healio.com/news/ophthalmology/20181113/new-iol-dedicated-for-scleral-fixation?M_BT=3592487855654.

Carlevale Lens (Carlo Carlevale) by Soleko, "Scleral Suturefree IOL—Product Description." Alyko Medical, www.alykomedical.com/en-GB/products/implants/scleral-sutureless-iol-34097888. Accessed Oct. 29, 2020. 1 page.

Hao, Y. et al. (2001). "Intracapsular IOL implantation of cataract with subluxation of lens." Journal of Ocular Trauma and Occupational Eye Diseases (with Ophthalmology Surgery), Issue 05, Sep. 30, 2001. 2 pages. [English abstract translation—p. 2].

* cited by examiner

DEVICES TO SUPPORT AND POSITION AN INTRAOCULAR LENS WITHIN THE EYE AND METHODS OF USE

CROSS-REFERENCE TO RELATED APPLICATIONS

This application is a continuation of U.S. patent application Ser. No. 17/396,048 filed Aug. 6, 2021, which claims the benefit of priority to U.S. Provisional Application Ser. No. 63/063,110, filed Aug. 7, 2020; 63/089,241, filed Oct. 8, 2020; 63/129,448, filed Dec. 22, 2020; and 63/183,488, filed May 3, 2021. The entire contents of these applications are incorporated by reference in their entireties.

U.S. patent application Ser. No. 17/396,048, filed Aug. 6, 2021, is a continuation-in-part of U.S. application Ser. No. 16/988,519, filed Aug. 7, 2020, now U.S. Pat. No. 11,759,309, which claims the benefit of priority to U.S. Provisional Application Ser. No. 63/017,423, filed Apr. 29, 2020, and 63/053,450, filed Jul. 17, 2020. The entire contents of these applications are incorporated by reference in their entireties.

BACKGROUND

The present disclosure relates generally to the field of ophthalmics, more particularly to ophthalmic devices for supporting and positioning intraocular lenses in the eye.

Implantation of an intraocular lens (IOL) requires support within the eye to hold it in the correct position. Normally, this is achieved through the native capsular bag suspended by the zonules (fine thread like structures). However, lens support can be compromised iatrogenically either during the time of surgery (either anterior or posterior segment surgery) or from other ocular procedures such as intravitreal injection. Commonly the posterior capsule is affected, thus preventing secure placement of the IOL in the capsular bag.

To overcome the absence of posterior capsular support due to posterior capsule rupture surgeons often place the IOL on top of the anterior capsule with the IOL haptics directed toward the ciliary sulcus. However, this can introduce a host of complications since commercially available IOLs are not optimized for this location. Specifically, neither the sizing nor the surface contours are ideal for placement between the anterior capsular and the iris. Because of this, the IOL optic or haptics can cause chafing of the iris or ciliary body leading to untoward complications including Uveitis, Glaucoma, Hyphema (UGH) syndrome. This is particularly problematic with one-piece IOLs so three-piece IOLs are typically used in this scenario. However, three-piece IOLs with square-edged optics, although commonly used, can also cause iris chafe, inflammation, pigment release, and glaucoma. Additionally, most toric, multifocal, trifocal, and extended depth of focus lenses are only available in the one-piece design. As a result, these technologies cannot be safely implanted for the patient after posterior capsular rupture.

Unless special maneuvers are undertaken (e.g., optic capture) a sulcus placed IOL can decenter causing decreased vision and photopsias, frequently requiring additional surgery. This problem can be exacerbated if the decentered IOL erodes into iris, ciliary body or retina, which risks permanent vision loss.

The management of secondary IOL placement in the absence of posterior capsular support continues to evolve. Currently the only FDA approved solution is placement of an anterior chamber IOL (ACIOL). The ACIOL is a larger lens with the ability to sit anterior to the iris; however over time these lenses can cause UGH syndrome as well as endothelial cell loss and corneal decompensation, and as a result are contraindicated in many patients. Off-label techniques can be employed, such as iris suturing IOL, but this is technically difficult and can lead to iris pigment loss causing glaucoma. Lastly, scleral suturing IOLs with islets is technically complex, risks rotation, and the durability of the sutures is limited leading to cases of suture breakage and lens subluxation. Additionally, all of these techniques force the surgeon to use an alternative lens type, instead of their preferred lens for the patient. Lastly, the decision of timing is critical, as lens calculations are often inadequate during the initial vitrectomy/lensectomy yet there is the desire to avoid additional surgery, so sub-optimal lenses are frequently implanted.

SUMMARY

In an aspect, provided is an implantable device for supporting an artificial intraocular lens in an eye having an anterior segment of a capsular bag, an iris, and a sclera. The device includes a posterior platform having an anterior-facing surface and an inner wall defining, at least in part, a central aperture. When the device is implanted in the eye, light passes through the intraocular lens and the central aperture of the posterior platform towards the retina. The device includes at least one awning positioned over the anterior-facing surface of the posterior platform forming at least one recess anterior to the posterior platform. The device is configured to be deployed in the eye posterior of the iris so that no portion of the device rests in contact with the sclera after implantation.

The at least one awning positioned over the anterior-facing surface of the posterior platform can define an anterior opening. The at least one awning can include a visualization feature that projects inward from the at least one awning so as to narrow a dimension of the anterior opening. In use, the visualization feature can be directly visualized through a pupil of the eye. The device can have an elongate shape having a long axis and a short axis. The dimension of the anterior opening that is narrowed can be a distance between central-most edges of the anterior opening along the long axis of the device. The distance can be at least about 5.0 mm up to about 7.0 mm. The distance can be greater than a diameter of the central aperture. During use, at least a portion of the intraocular lens can be positioned within the at least one recess against the anterior-facing surface. An external surface of the at least one awning can have a smooth geometry to protect the iris from the intraocular lens upon implantation of the device. An internal surface of the at least one awning can provide counter pressure to a haptic of the intraocular lens upon positioning of the intraocular lens on the anterior-facing surface.

The device can further include one or more stabilization features. The one or more stabilization features can extend posteriorly from a posterior surface of the posterior platform and include a posterior stabilization feature configured to engage with at least a portion of the capsular bag. The posterior stabilization feature can include a first portion projecting posteriorly from a posterior surface of the posterior platform and a second portion projecting laterally outward from the first portion. The one or more stabilization features can include a plurality of radially extending structures coupled to the device. Each of the plurality of radially extension structures can include a radially outermost portion for sutureless positioning of the device within the eye. The radially outermost portion can be configured to provide non-penetrating contact with ciliary tissue in the eye to prevent rotation around the visual axis and aid in centration of the device relative to the eye. The posterior platform can include an outer perimeter that is substantially non-circular and an inner perimeter that is substantially circular. The outer perimeter can be substantially rectangular and can have a pair of elongate sides and a pair of short sides. The plurality of radially extending structures can include four radially extending structures. Each of the four radially extending structures can extend radially outward from a location where and elongate side meets a short side. The posterior platform can lie within a plane and the radially outermost portion of the plurality of radially extension structures lies within the plane of the posterior platform. The posterior platform can lie within a plane and the radially outermost portion of the plurality of radially extension structures lies anterior to the plane of the platform. The at least one awning can project anterior to the radially outermost portion.

An anterior segment of the capsular bag can provide support for the device along a Z-axis of the eye. The posterior platform can further include one or more cut-outs peripheral to the central aperture. The posterior platform can be sized and shaped to support a central optic of the intraocular lens on an anterior-facing surface of the posterior platform and the one or more cut-outs can be sized and shaped to receive at least a portion of a haptic of the intraocular lens when the intraocular lens is implanted within the at least one recess of the device. The device can further include one or more stabilization features configured to engage with at least a portion of the capsular bag. The one or more stabilization features can extend posterior to the at least one recess. The one or more stabilization features can extend anterior to the at least one recess.

In an interrelated aspect, provided is a system including the implantable device for supporting an artificial intraocular lens in an eye and the artificial intraocular lens. The intraocular lens can be a one-piece intraocular lens or a multi-piece intraocular lens. The one-piece intraocular lens can be a unifocal, toric, multi-focal, extended depth of focus, or accommodating intraocular lens.

In an interrelated aspect, provided is a method of implanting the device for supporting an artificial intraocular lens in an eye. The method includes inserting the device posterior of the iris into the posterior chamber of the eye; and positioning a one-piece intraocular lens relative to the posterior platform so at least a portion of the intraocular lens is positioned under the at least one awning and at least a portion of the intraocular lens is against the anterior-facing surface. A haptic of the intraocular lens can be positioned under the at least one awning. Inserting the device into the posterior chamber of the eye can include inserting the device without fixing the device trans-sclerally.

In an interrelated aspect, provided is a method for supporting an artificial intraocular lens (IOL) in an eye including preparing a lens support device for insertion into the eye. The lens support device includes a posterior platform having an anterior-facing surface and a posterior-facing surface; a central aperture extending through the posterior platform, wherein, when the lens support device is implanted in the eye light passes through the central aperture towards a retina; at least one awning projecting over at least a portion of the anterior-facing surface of the posterior platform, the at least one awning having an internal surface and an external surface, the awning forming at least one recess between the internal surface of the awning and the anterior-facing surface of the posterior platform; and a plurality of radially extending structures coupled to and projecting radially outward from the device, the radially extending structures having a radially-outermost portion for sutureless positioning within a posterior chamber for positioning of the lens support device in the eye. The method further includes placing the lens support device posterior of the iris in the eye so the posterior-facing surface of the posterior platform is positioned anteriorly to an anterior segment of the capsular bag of the eye and without placing any portion of the device in contact with a sclera of the eye; positioning the radially outermost portion of the radially extending structures adjacent the sulcus to position the central aperture posterior to a pupil of the eye; positioning an optical portion of the IOL over the central aperture and anterior to at least a portion of the anterior-facing surface of the posterior platform; and positioning at least a portion of a haptic of the IOL within the at least one recessed portion to affix the IOL to the lens support device.

In an interrelated aspect, provided is a method for implanting an artificial intraocular lens (IOL) in an eye including creating an opening in an anterior wall of a capsular bag of the eye and preparing a lens-support device for insertion into the eye. The lens-support device including a body portion having a central opening and a lens-support structure. The lens-support structure includes a substantially planar lens-support surface at least partially surrounding a perimeter of the central opening, and at least one recess anterior to the lens-support surface. When the device is implanted in the eye, light passes through the central opening towards a retina. The method further includes a plurality of radially extending structures coupled to the body portion. Each of the plurality of radially extended structures includes a radially outermost portion for sutureless positioning of the device within a posterior chamber of the eye; and a plurality of stabilization features extending posteriorly from a posterior surface of the lens-support structure. The method further includes inserting the lens-support device into the eye and posterior of an iris in the eye, such that, after insertion, no portion of the device rests in contact with a sclera of the eye. The method further includes positioning the radially outermost portion of each of the plurality of structures adjacent a sulcus of the posterior chamber to stably position the central opening posterior to a pupil of the eye; inserting each of the plurality of stabilization features through the opening in the anterior wall of the capsular bag to assist in anchoring the device relative to the capsular bag; inserting an IOL into the eye; positioning an optical portion of the IOL over the central opening and anterior to at least a portion of the substantially planar lens-support surface; and positioning at least a portion of a haptic of the IOL within the at least one recess of the lens-support structure to affix the IOL to the lens-support device.

In an interrelated aspect, provided is a method for implanting an artificial intraocular lens (IOL) in an eye including creating an opening in an anterior wall of a capsular bag of the eye; preparing a lens-support device for insertion into the eye. The lens-support device includes a body portion having a central opening, wherein, when the lens-support device is implanted in the eye, light passes through the central opening towards a retina. The body portion further includes a lens-support surface at least partially surrounding a perimeter of the central opening, and at least one recess anterior to the lens-support surface; and at least one stabilization feature extending posteriorly from a posterior surface of the lens-support structure. The method further includes inserting the lens-support device into the eye and posterior of an iris in the eye, such that, after insertion, no portion of the device rests in contact with a sclera of the eye; inserting the at least one stabilization feature through the opening in the anterior wall of the capsular bag to anchor the lens-support device relative to the capsular bag and position the central opening posterior to a pupil of the eye; inserting an IOL into the eye; positioning an optical portion of the IOL over the central opening and anterior to at least a portion of the lens-support surface; and positioning at least a portion of a haptic of the IOL within the at least one recess to secure the IOL to the lens-support device.

The lens-support device can further include a plurality of radially extending structures coupled to the body portion. Each of the plurality of radially extended structures can include a radially outermost portion for sutureless positioning of the device within the eye. The method can further include positioning the radially outermost portion of each of the plurality of radially extending structures adjacent a sulcus of the eye to prevent rotation around the visual axis and aid in centration of the device relative to the eye.

In some variations, one or more of the following can optionally be included in any feasible combination in the above compositions, methods, devices, and systems. More details of compositions, methods, devices, and systems are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally speaking the figures are not to scale in absolute terms or comparatively but are intended to be illustrative. Also, relative placement of features and elements may be modified for the purpose of illustrative clarity.

It should be appreciated that the drawings herein are for illustration only and are not meant to be to scale.

DETAILED DESCRIPTION

The present disclosure relates generally to the field of ophthalmics, more particularly to ophthalmic devices, including artificial support structures that can be used to support an intraocular lens (IOL) or other ophthalmic implant when "in the bag" implantation is not desirable.

The most common treatment for aphakia caused by removal of a cataractous lens is placement of an IOL within the native lenticular capsular bag. The capsular bag, which has an anterior component and a posterior component creating an inner chamber, is supported by zonules, thus providing a stable structure for IOL support. Typical IOLs include an optic and one or more haptics that support the optic within the eye. The design of the IOL largely dictates where the IOL may be implanted in the eye. For example, one-piece IOLs such as multi-focus, toric, and accommodating IOLs are sometimes preferred by both surgeons and patients. These premium lenses are not typically suitable for implantation within the sulcus due to their haptic edge sharp geometries and greater anterior-to-posterior haptic thickness, which can cause damage to the iris. However, in some cases, implantation within the bag is not desirable, for example, due to a torn or missing anterior or posterior capsule or zonules.

The devices described herein can be implanted into the posterior chamber of the eye and fixed atop the anterior capsule to stably hold IOLs of all designs (one-piece or multi-piece IOLs) with a variety of haptic and optical designs to provide a reliable refractive result. The devices described herein can incorporate features specifically designed to accommodate toric IOLs by maintaining IOL orientation. The devices also allow for posterior segment placement that greatly reduces risk of damage to iris, anterior chamber angle, or cornea. Implantation posterior to the iris and cornea eliminates or reduces risk of corneal injury, iris bleeding and glaucoma. The devices described herein reduce the risk of complications compared to current technologies such as ACIOL, Iris-sutured lens, or Scleral-sutured lens, or to placement of commercially-available IOLs in the ciliary sulcus. The devices described herein provide a full range of IOL options to surgeons and patients.

Figure 1A:
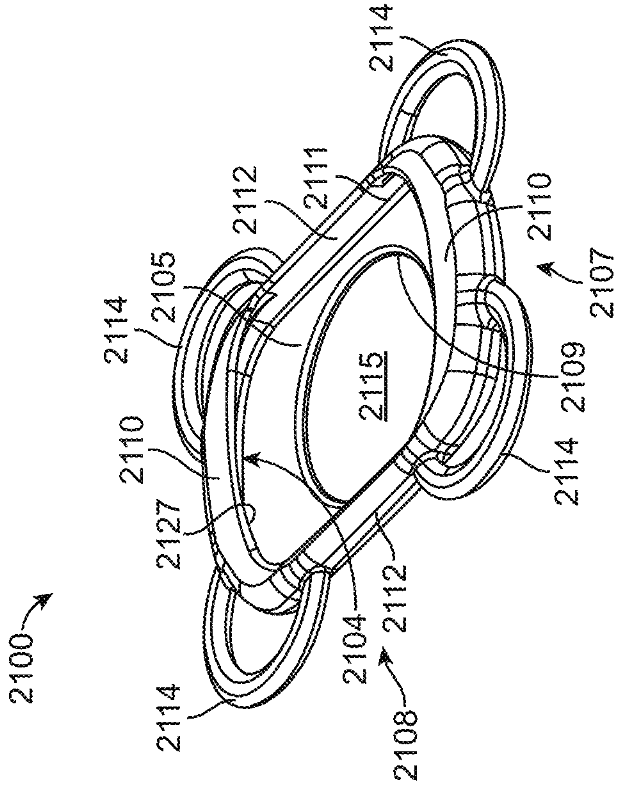
FIG. 1A shows a perspective view of an implementation of a device.
Figure 1B:
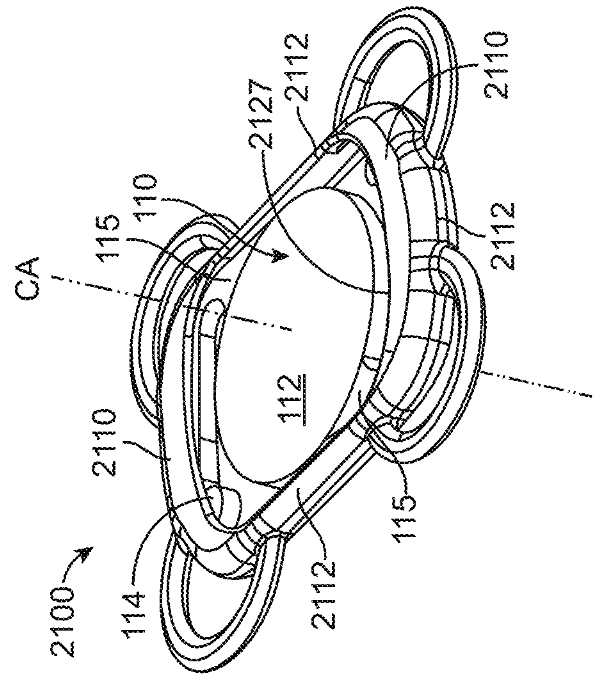
FIG. 1B shows the device of FIG. 1A having an intraocular lens (IOL) deployed within it.
Figure 1D:
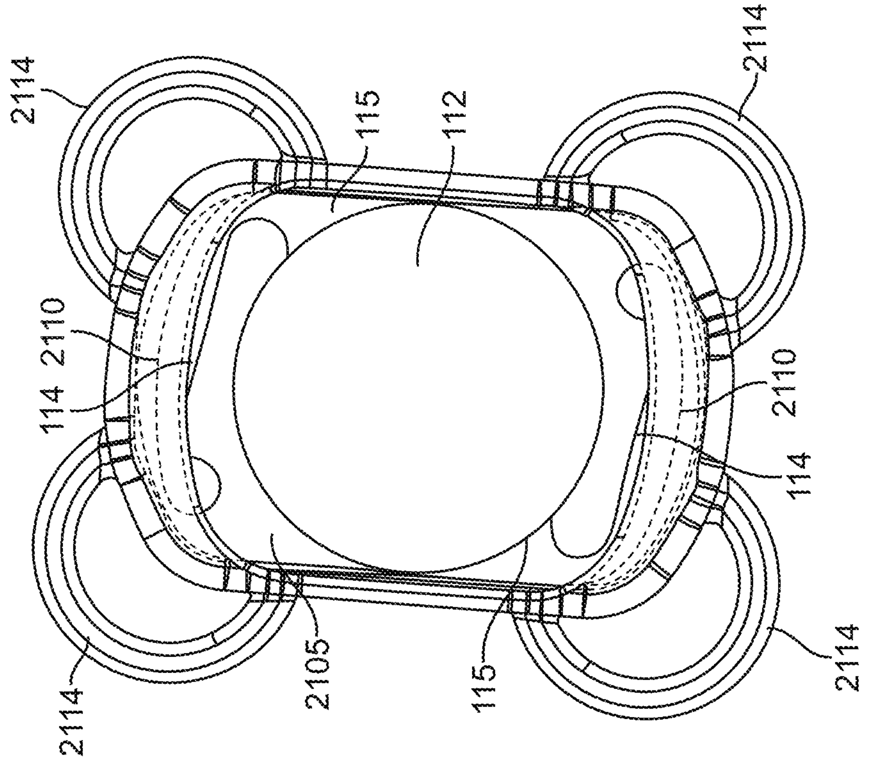
FIGS. 1C-1D are top down views of the device of FIG. 1B.
Figure 1C:
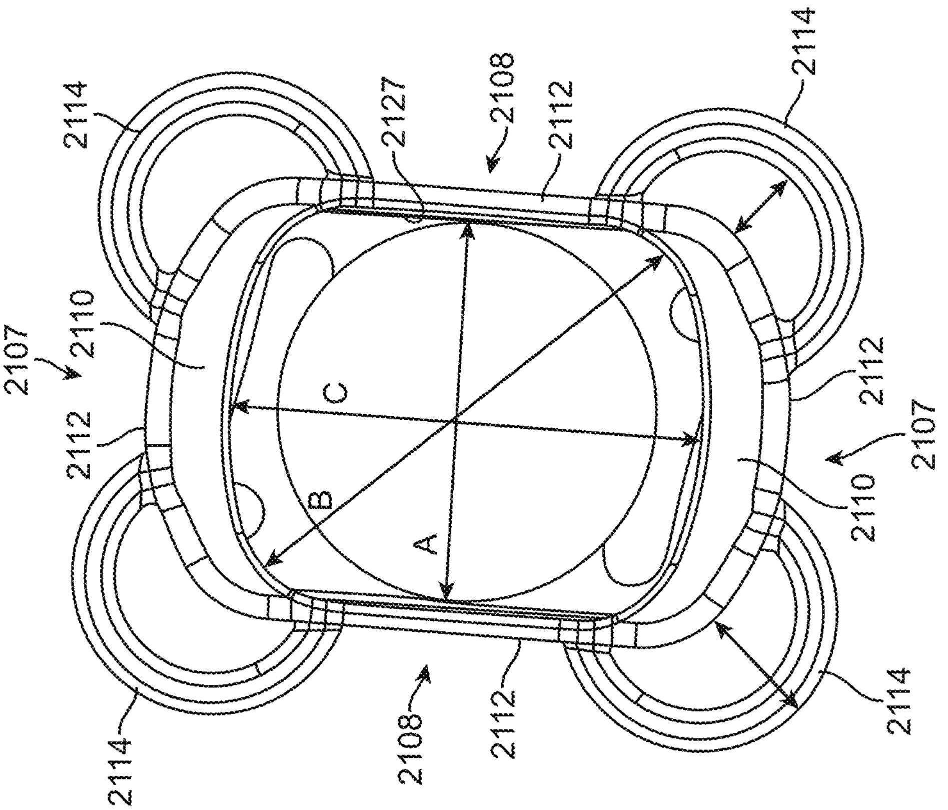
Figure 2A:
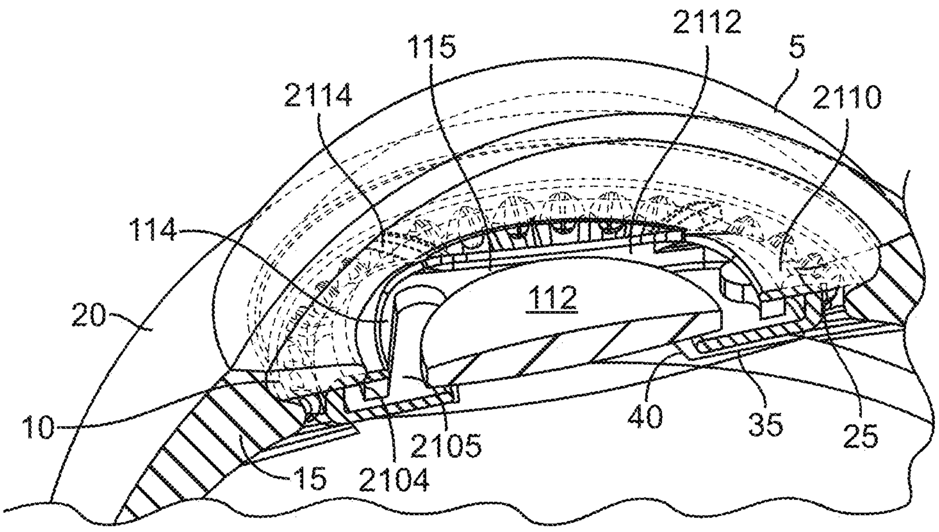
FIG. 2A shows a cross-sectional view of the device of FIG. 1B deployed within an eye to support an IOL.
Figure 2B:
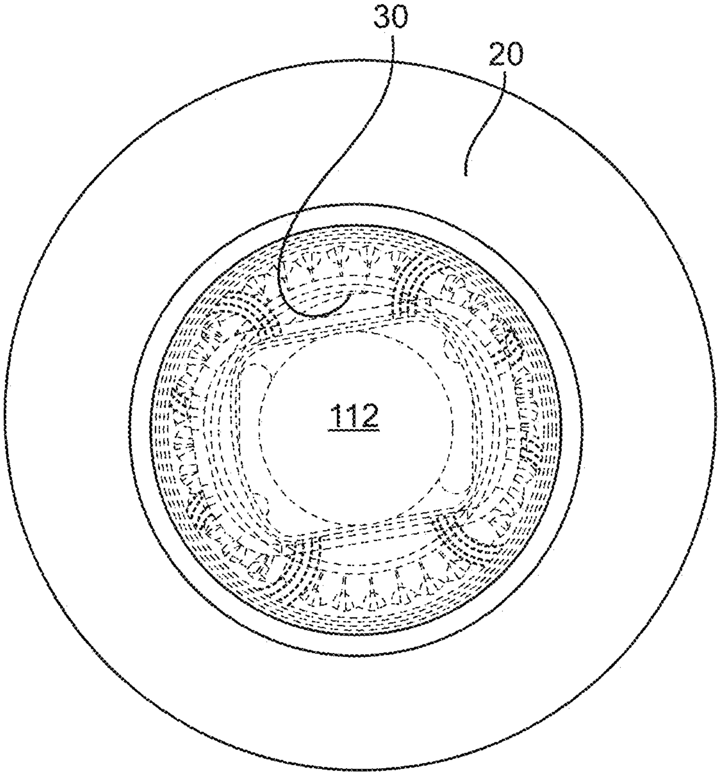
FIG. 2B shows a top down view of the eye implanted as in FIG. 2A.

FIGS. 1A-1D illustrate an implementation of a lens-support device 2100 for supporting and positioning an IOL 110 within the eye. FIG. 1A is a perspective view of the device 2100 prior to positioning of an IOL 110. FIGS. 1B-1D show the device 2100 after positioning of the IOL 110 with the device 2100. FIG. 2A shows a model of an eye and a cross-sectional view of the device 2100 deployed to support the IOL 110. FIG. 2B shows the eye looking through the iris 10, which is illustrated as transparent. FIG. 2B also shows the cornea 5, the ciliary body 15, the sclera 20, the ciliary sulcus 25, and the pupil 30 defined centrally through the iris 10. The device 2100 is configured to be positioned against the anterior segment 35 of the capsular bag between the anterior capsular segment 35 and the iris within the posterior chamber over a capsulorhexis 40. The capsulorhexis 40 is an opening created in an anterior wall of the capsular bag. The anterior capsular segment 35 is preferably intact although in some implementations of the device 2100 the anterior segment of the capsular bag may be partially torn. The device 2100 can include a posterior lens-support structure or platform 2105 for positioning against the anterior capsular bag 35, one or more awnings 2110 projecting over a portion of the platform 2105, and one or more stabilization features, such as a plurality of radially extending structures or bumpers 2114 coupled to the body portion of the device and configured to provide non-penetrating contact with eye tissues. The posterior platform 2105 can support an IOL 110 and prevent it from falling into the posterior chamber upon implantation. The anterior segment 35 of the capsular bag can provide Z-axis support for the posterior platform 2105. The one or more awnings 2110 together with the platform 2105 form a body portion that helps to position and fix the IOL 110 against the platform 2105 while protecting surrounding eye tissues such as the iris from damaging contact with the IOL 110. Even portions of the IOL 110 that are not covered by the awnings 2110 may be effectively shielded because they are recessed relative to the anterior-most surface of the device 2100 (i.e., the anterior-facing surfaces of the awnings 2110). The one or more bumpers 2114 positioned near a perimeter of the platform 2105 and project outward from the device 2100 so as to atraumatically contact ciliary eye tissues such as the ciliary body 15 or the ciliary sulcus 25 to provide centration of the device 2100. The one or more bumpers 2114 can also provide anti-rotation function in the Z-plane and/or prevent displacement within the Z-plane to maintain proper alignment between the central aspect of the device and the eye's visual axis. In some implementations, one or more stabilization features can be positioned relative to the device to engage with at least a portion of the capsular bag, such as the anterior capsule, to stabilize and provide centration and fixation of the device relative to the eye (see stabilization feature 2138 of FIGS. 5A, FIGS. 8A-8F, 9A-9B, and 10A-10D). The stabilization features 2138 can engage with the capsulorhexis in the anterior segment of the capsule. The device can be configured to position the IOL 110 anterior to the capsulorhexis outside the capsular bag or posterior to the capsulorhexis inside the capsular bag. Each of these implementations will be described in more detail below.

An IOL 110 typically includes a central optic 112 and two haptics 114 each coupled to the optic 112. The device 2100 may accommodate IOLs 110 having any of a variety conventional designs, including multi-piece IOLs, one-piece IOL, and plate designs. Similarly, the haptics 114 of the IOL 110 can be of any of a variety of configurations. The haptics 114 can be conventional open loop haptics such as C-loop, J-loop, modified J-loop, or other haptics. One-piece IOLs can have open loop haptics similar to conventional three-piece IOLs. One-piece IOLs may also incorporate monobloc-plate style haptics. Where the device 2100 is shown with one type of IOL (e.g., multi-piece IOLs or one-piece IOL), it should be appreciated that another type of IOL can be mated with the device.

Again with respect to FIG. 1A, the posterior lens support structure or platform 2105 of the device 2100 can have an anterior-facing, lens-support surface directed towards a front of the eye when the platform 2105 is in use and a posterior-facing surface directed towards a back of the eye against the capsular bag when the platform 2105 is in use. The posterior platform 2105 can provide several functions. The posterior platform 2105 can have a surface (the anterior-facing surface or posterior-facing surface) forming a stable platform against which an IOL 110 can be placed during use. The posterior platform 2105 can take the place of a capsular bag and can set the effective lens position of the IOL 110 within the eye. The geometric and mechanical function of the posterior platform 2105 not only supports the IOL 110 when in use, it can also serve to assist in the centration of an IOL 110 in the case of an asymmetric eye or asymmetric surgical procedure. The posterior platform 2105 provides artificial anterior capsule support for the IOL and a stable platform structure in the eye recapitulating the native anterior capsule. The posterior platform 2105 can be substantially flat or planar between the anterior-facing surface and the posterior-facing surface. The thickness of the posterior platform 2105 between the anterior-facing surface and the posterior-facing surface can be minimized while still providing sufficient support to the IOL. The thickness can be between about 0.02 mm and 1.5 mm, or between about 0.5 mm and 1.0 mm. The posterior platform 2105 can be about 0.2 mm. The thickness of the posterior platform 2105 can be thinner than 0.2 mm and still provide sufficient support for an IOL. For example, the posterior platform 2105 can be reinforced with a stiffer material to reinforce it and limit its distortion despite being only 0.2 mm thick. Alternatively, the posterior platform 2105 can have an increased thickness (e.g., about 0.50 mm up to about 1.0 mm) and the material thickness sufficient to limit distortion of the device even when placed under tension and/or compression. Increased stiffness of the lens support structure can facilitate easier insertion of the IOL following implantation. This can additionally increase the hoop strength of an aperture 2115 extending through the posteriori platform 2105 as described in more detail below, which can limit the risk of the IOL accidentally passing through the aperture 2115 upon implantation of the IOL in the device 2100. Reinforcement of the devices described herein to avoid distortion and risk of the IOL passing through the device is discussed in more detail below.

Still with respect to FIGS. 1A-1D, the posterior platform 2105 can include an outer region 2111 defining the overall shape of the posterior platform 2105 and an inner wall 2109 defining the central opening or aperture 2115 extending through the full thickness of the posterior platform 2105 from the anterior-facing surface through to the posterior-facing surface. The central aperture 2115 is configured to be substantially co-axial with an optical axis of an IOL once positioned on the posterior platform 2105 of the device 2100. When the device is implanted in the eye, light passes through the central aperture 2115 and through the optical axis of the IOL towards the retina. The device securely fixes the IOL 110 in a coaxial position. The central aperture 2115 can provide a generally ring-shape to the posterior platform 2105. However, the posterior platform 2105 need not be circular in shape on both its inner and outer perimeter surfaces. For example, the inner wall 2109 of the posterior platform 2105 can be substantially circular or have a circumference that forms a uniform, substantially circular shape. The outer region 2111 of the posterior platform 2105 can, but need not be circular in shape. The outer region 2111 of the posterior platform 2105 can have any of a variety of non-circular shapes including rounded rectangle as shown in FIGS. 1A-1D, or oval, elliptical, rounded triangle, or other geometric or free-form shape, etc. In some implementations, the non-circular shape of the outer region 2111 includes a plurality of lobes projecting outward from a plurality of sides. The plurality of lobes can project radially away from the central aperture 2115. The plurality of sides can be substantially flat or concave. The posterior platform 2105, thus, can have a width between the outer region 2111 and the inner wall 2109 that varies around the circumference. The shape of the outer region 2111 of the posterior platform 2105 and the interaction of the device 2100 within the eye will be described in more detail below. The non-circular shape of the outer perimeter surface can be a rounded rectangle having a pair of shorts sides 2107 and a pair of elongate sides 2108.

The IOL 110 may be positioned against the posterior platform 2105 above the central aperture 2115 so that the central axis CA extending anterior-to-posterior through the central aperture 2115 extends through the optic 112 of the IOL 110 (see FIG. 1B). Light is permitted to pass through the aperture 2115 as well as the IOL 110 positioned on the posterior platform 2105. The central aperture 2115 can be substantially co-axial with the optical axis of the IOL 110 once the IOL is positioned against the posterior platform 2105. The central aperture 2115 has a diameter sized to allow the optic 112 of the IOL to be supported on the anterior-facing surface of the posterior platform 2105 without the IOL 110 falling through into the posterior chamber. The diameter of the central aperture 2115 avoids the posterior platform 2105 from overlapping substantially with the optic 112 of the IOL 110 so that it allows light to pass through the device without any optical disturbance as it passes towards the retina. The diameter of the aperture 2115 is designed to be generally universal for a wide range of IOL types. Conventional IOLs typically have optics with an outer diameter of 6 mm although this size can vary depending on the IOL. A central aperture 2115 having a diameter that is less than 5.0 mm down to about 4.0 mm, preferably about 4.75 mm, can be used with some IOLs. A central aperture 2115 having a diameter that is between 5.0 mm to about 6.0 mm can be used with most IOLs such that the device is nearly universal for use with any conventional haptic-stabilized IOL. The minimum inner diameter of the aperture 2115 can be greater than about 4.0 mm, greater than about 4.5 mm, greater than about 5.0 mm, greater than about 5.5 mm, greater than about 6.0 mm, greater than about 6.5 mm, up to about 7.0 mm, up to about 8.0 mm, up to about 9.0 mm, up to about 10 mm, up to about 15 mm, and any range in between. The central aperture 2115 inner diameter can be between about 4 mm to about 8 mm, or between about 4 mm up to 6 mm. The inner diameter of the central aperture 2115 can approach the outer diameter of a common IOL optic 112, for instance at least about 5.5 mm or 6.0 mm.

The aperture diameter can be selected to maintain a particular hoop strength to limit the risk of accidentally passing the IOL through the aperture 2115 upon implantation. Smaller aperture diameters can increase the hoop strength compared to larger aperture diameters. A stiffer IOL housing limits distortion of the aperture 2115 when placed under tension and/or compression. The increased stiffness of the IOL housing can also facilitate easier insertion of the IOL following fixation in the eye.

The central aperture 2115 need not be smaller than the IOL diameter. Where the central aperture 2115 has an inner diameter that is larger than the outer diameter of the IOL optic 112, the posterior platform 2105 may incorporate one or more features that extend out into the central aperture 2115 to effectively reduce the inner diameter of the central aperture 2115 so the platform 2105 may support the IOL optic and prevent the IOL 110 from falling through the central aperture 2115. The device 2100 can include a plurality of leaflets configured to support the optic of the IOL. The leaflets can project inwardly relative to the inner wall 2109 of the platform 2105 such that they extend within the opening of the central aperture 2115. The leaflets can support the optic on their anterior-facing surface or can be deflected so that the optic passes to and is support by the posterior-facing surface of the leaflet. The haptic 114 of the IOL 110 can remain on the anterior-facing surface of the platform 2105 and the optic 112 of the IOL 110 can be positioned on the posterior-facing surface of the leaflet thereby maintain a Z-position of the IOL 110. The leaflets can be full thickness or partial thickness. Meaning, the leaflets can be as thick as the platform 2105 or can be thinner than the platform 2105. The leaflets can stem from the anterior-facing surface of the platform 2105. The leaflets can also stem from the posterior-facing surface of the platform 2105. If stemming from the posterior-facing surface, the optic 112 of the IOL 110 can be positioned within the recess formed by the central aperture 2115 and the anterior-facing surface of the leaflets. The device 2100 can include one, two, three, or more leaflets. Each of the leaflets can be arranged symmetrically around the platform 2105. The leaflets can define a narrower inner diameter than the inner diameter of the central aperture 2115. The narrower inner diameter of the leaflets can be from about 4.0 mm to 6.0 mm, or from about 5.0 mm to 5.5 mm, or about 5.0 mm. Each leaflet can have a thickness that is from about 0.10 mm to 0.50 mm, or about 0.15 mm to about 0.35 mm, or about 0.25 mm.

The central aperture 2115 can be the only aperture extending through the posterior platform 2105 such that the platform 2105 has a single optical aperture extending through its full thickness. In some implementations, the posterior platform 2105 incorporates full-thickness openings in addition to the central aperture 2115. These additional openings can create a discontinuous posterior surface to the device 2100 that can reduce its overall bulk while still providing sufficient surface area for supporting the IOL 110. In some implementations, the discontinuous posterior surface can include one or more cut-outs 2144 through the posterior platform 2105 (see FIGS. 8A-8E). In other implementations, the device 2100 has no posterior support 2105 and instead relies upon the anterior capsular bag to support the central optic 112 along the Z-plane (see FIGS. 9A-9B). Each will be described in more detail below. In still other implementations, the posterior platform 2105 (whether having a discontinuous or continuous surface) has no central aperture 2115 defined by an inner perimeter 2109. The solid posterior platform 2105 can aid in preventing vitreous loss. In some implementations, the solid posterior platform 2105 can be a plano optical surface configured to allow light to pass through. In other implementations, the posterior platform 2105 has refractive or light-filtering optical properties.

In some implementations, the posterior-facing surface of the posterior platform 2105 is configured to sit against the anterior capsule 35 (see FIG. 2A). The posterior-facing surface of the posterior platform 2105 may include one or more features or can be textured to increase friction and prevent inadvertent movement of the device relative to the anterior capsule 35 following implantation. The increased friction can help to minimize lateral and/or rotational movement of the device 2100 relative to the anterior capsule 35.

The IOL 110 is shown in FIG. 1B positioned against the anterior-facing surface of the posterior platform 2105. In some circumstances, there may be limited space between the anterior surface of the device 2100 and the posterior surface of the iris 10. In order to reduce the risk of iris damage or pupillary block, the IOL 110 can be fixed on or posterior to the plane of the posterior platform 2105. The posterior platform 2105 can be constructed such that a surgeon can use the "optic capture" technique for implantation of the IOL 110 relative to the device 2100. In this technique, the optic 112 of the IOL 110 is passed partially or completely through the central aperture 2115 to a posterior side of the posterior platform 2105 while the haptics 114 of the IOL 110 can remain substantially anterior to the posterior platform 2105. This technique provides secure fixation of the IOL 110 so that it cannot drift in the X, Y or Z axes following surgery and reduces bulk in the space anterior to the lens. The technique additionally allows for safe use of "square edge" IOL designs by mitigating IOL contact with the posterior surface of the iris 10. Surgeons have added flexibility in modifying IOL power by offering a choice in effective lens position. The technique also allows for the use astigmatism-correcting (toric) IOLs by limiting IOL rotation. Additionally, securing the optic while enhancing the predictability of its refractive position makes pre-operative lens choice calculations more accurate.

In order to facilitate the use of the optic capture technique, the aperture 2115 can have a diameter that is similar to that of common IOL optic diameters, for instance 5.5 mm or 6.0 mm. In this circumstance, the surgeon can pass the IOL 110 through the aperture 2115 with force parallel to the optical axis or by slightly tilting the IOL 110 to ease the IOL 110 through the aperture 2115. Alternatively, the device 2100 can incorporate features that allow the diameter of the aperture 2115 to temporarily enlarge to allow the IOL 110 to pass through the aperture 2115. As mentioned, the platform 2105 can include an inner wall 2109 defining the central aperture 2115. The inner wall 2109 can be discontinuous such that the platform 2105 forms a split-ring having a gap between terminal ends of the ring. In this implementation, the inner diameter of the aperture 2115 can change depending on whether the terminal ends of the ring are positioned toward one another or spread apart. In another implementations, the inner wall 2109 defining the central aperture 2115 can be discontinuous. The device 2100 can have one or more slits in the inner wall 2109 circumferentially located around the aperture 2115. The slits can preferably have a length radially outward from the inner wall 2109 (e.g., 0.25 mm-2.0 mm) to thereby increase flexibility of the platform 2105 and expand the effective diameter of the central aperture 2115 to pass the optic 112 through the pliable lens platform 2105. Alternatively, the device 2100 can incorporate one or more deflectable flaps molded into the platform 2105. The device 2100 can include more than a single deflectable flap, for example, 2 to 40 flaps that would deflect to pass the IOL 110 through the aperture 2115 when sufficient force is imparted by the surgeon. Alternatively, the inner wall 2109 can have a brush-like structure that deflects and allows the IOL 110 to pass when under sufficient force imparted by the surgeon. In still further implementations, the cross-sectional thickness profile of the platform 2105 may be tapered towards the aperture 2115. The outer region 2111 of the platform 2105 can have a greater thickness (e.g., thickness measured anteriorly-to-posteriorly when the device is positioned in the eye) than the thickness of the inner perimeter of the platform 2105 near the inner wall 2109. Thus, the center-most portion of the platform 2105 (i.e., the inner wall 2109) can have greater flexibility due to the reduced thickness allowing an IOL 110 to pass through the aperture 2115 and deflect the inner wall 2109 when placed under sufficient force. Despite the greater flexibility near the inner wall 2109 whether due to slits, flaps, or a reduced thickness, the platform 2105 has sufficient strength to support an IOL 110 resting on the anterior surface of the platform 2105 or an IOL that is partially or completely posterior to the platform 2105.

Again with respect to FIG. 1A-1B, the outer region 2111 of the posterior platform 2105 can couple to one or more side walls 2112 that project anteriorly from the outer region 2111. The side walls 2112 can curve out over the anterior-facing surface of the posterior platform 2105 forming one or more awnings 2110. The awnings 2110 in combination with the side walls 2112 can create a body portion defining one or more recesses 2104 anterior to the anterior-facing lens-support surface. At least a portion of the IOL 110 can be positioned within the one or more recesses 2104 of the body portion. As discussed above, the device 2100 can be inserted into the eye posterior of the iris such that after insertion, no portion of the device rests in contact with a sclera of the eye. The radially outermost portion of each of the plurality of radially extending structures can be positioned adjacent the sulcus of the posterior chamber to stably position the central opening 2115 posterior to the pupil of the eye. The IOL 110 can then be inserted into the eye and positioned so that the optic 112 of the IOL 110 is over the central aperture 2115 of the posterior platform 2105 and anterior to at least a portion of the lens-support surface of the platform 2105. A perimeter region of a posterior-facing surface of the optic 112 can be positioned against the anterior-facing surface of the posterior platform 2105. Each of the haptics 114 of the IOL 110 can be positioned substantially or at least in part within respective recesses 2104 on opposing sides of the central aperture 2115 while a majority of the optic 112 of the IOL 110 remains outside the recesses 2104 and exposed through the anterior opening 2127 of the device 2100 (see FIG. 1B) to affix the IOL 110 to the device 2100.

An elongated, anterior opening 2127 can be defined by the space between the awnings 2110 and/or side walls 2112. The anterior opening 2127 can be large enough to allow for the easy passage and implantation of all IOL types (one-piece, three-piece, plate, etc.) while still capable of capturing at least a portion of the haptics 114 of the IOL 110 under the awnings 2110 within the recesses 2104 so that the IOL 110 is retained posterior to the awnings 2110. The side walls 2112 can project anteriorly from the anterior-facing surface of the posterior platform 2105 a sufficient distance providing a height to the recess 2104 to allow for easy passage of the haptic 114 under the awnings 2110 and into the recesses 2104. This is particularly helpful to allow a surgeon to implant one-piece IOLs that patients prefer. One-piece intraocular lenses can include unifocal, toric, multi-focal, extended depth of focus, and accommodating intraocular lenses. However, the size of the recesses 2104 and thickness of the device 2100 is minimized to mitigate contact between the device and the back side of the iris upon positioning of the device against the anterior capsule. For example, the device 2100 can have a thickness from an anterior-facing surface of the awnings 2110 to a posterior-facing surface of the platform 2105 that is between about 0.3 mm and about 2.0 mm. This anterior-to-posterior thickness of the device is minimized to avoid interaction or contact between the awnings 2110 and the iris, the smooth outer surface geometry and rounded edges of the awnings 2110 and side walls 2112 prevents iris trauma in the case of contact. The height of the recess 2104 between the anterior-facing surface of the posterior platform 2105 to an inner-facing surface of the awnings 2110 can be at least about 0.65 mm, at least about 0.70 mm, at least about 0.75 mm, up to about 1.00 mm. The height of the recess 2104 provides space within which the IOL can be manipulated relative to the device. In some implementations, the posterior platform 2105 has a thickness that is about 0.20 mm and a recess height that is about 0.65 mm. In some implementations, the posterior platform 2105 has a thickness that is about 0.50 mm and a recess height that is about 0.75 mm. Thus, even despite the thicker posterior platform 2105 the height of the recess 2104 can be greater.

The awnings 2110 can be sized and shaped to cover potentially traumatic surfaces of the IOL 110 once the IOL 110 is positioned on the device 2100. For example, haptics 114 of an IOL 110 or the junctions 115 between the haptics 114 and the optic 112 of IOLs 110, particularly those designed to be implanted fully inside a capsular bag, can be formed of a material or have a surface geometry that is traumatic to the eye tissue. For example, edges of an IOL that are sharp or square can cause damage to delicate eye tissues like the iris. The awnings 2110 of the device 2100 are designed to cover at least these surfaces of the IOL 110 protecting the iris from contacting them.

In further implementations, the awnings 2110 can be sized and shaped to have at least a portion that projects more centrally than another to allow for anterior visualization of the device through the pupil. Intra-operative pupil diameter can be unpredictable during IOL implantation and can change mid-surgery. The centrally projecting visualization feature 2117 of the awnings 2110 can be designed for direct visualization of the device 2100 through the pupil while avoiding interfering with optics of the IOL after implantation. The centrally-projecting feature narrows an inner diameter of the anterior opening 2127, for example, an inner diameter along the long axis of the device. Awnings 2110 on opposite sides of the device 2100 can define a distance between their central-most edges that is at least about 7.0 mm down to about 5.0 mm, preferably about 6.0 mm. The direct visualization of the device 2100 during implantation of the IOL increases the likelihood that the IOL will be properly secured within the device. The anterior visualization feature of the device will be described in more detail below with respect to FIGS. 18E-18J.

In some implementations, the device 2100 has a single side wall 2112 extending around a perimeter of the platform 2105 and forms a single awning 2110 that extends 360 degrees around the central aperture 2115 and so that the edges of the optic 112 as well as the haptics 114 of the IOL 110 are at least partially covered. In other implementations, the device 2100 has a plurality of awnings 2110 coupled to the platform 2105 by a plurality of side walls 2112. For example, as shown in FIG. 1A-1B, the device 2100 can have a first awning 2110 projecting over an anterior-facing surface of a first short side 2107 of the platform 2105 and a second awning 2110 projecting over an anterior-facing surface of the opposite short side 2107 of the platform 2105. Each awning 2110 can have an arc length around the central aperture 2115 so that the collective surface area of the awnings 2110 and side walls 2112 is less than 360 degrees around the central aperture 2115. Each of the awnings 2110 can cover only a portion of each haptic 114 of the IOL and the edges of the optic 112 are left exposed. The awnings 2110 preferably do not overhang the optic portion 112 of the IOL 110 so that the elongated anterior opening 2127 is much larger than the diameter of the optic portion 112. This is in contrast to the smaller, central aperture 2115 of the posterior platform 2105 that approaches the diameter of the central optic portion 112 of the IOL 110. The anterior opening 2127 is generally significantly larger than the central aperture 2115. Even where the awnings 2110 can incorporate one or more visualization features 2117, the anterior opening 2127 defined by the awnings 2110 can be larger than the central aperture 2115 (see FIGS. 1E, 3, 15, 18A, 18I, and others).

The implementation shown in FIGS. 1A-1D has a single side wall 2112 extending around an entire perimeter of the platform 2105 along both elongated sides 2108 and both short sides 2107 at the location of the awnings 2110. In this implementation, the opposing awnings 2110 can be fully connected to one another along the sides 2108 forming a complete enclosure around the posterior platform 2105 that defines the anterior opening 2127. However, the side wall 2112 need not extend around the entire perimeter of the platform 2105. A first side wall 2112 can project anteriorly from a short side 2107 of the platform 2105 to connect to the awning 2110 and a second side wall 2112 can project anteriorly from the opposite short side 2107 of the platform 2105 to connect to its respective awning 2110. In this implementation, the anterior opening 2127 in the space between the awnings 2110 is not bordered on all sides by a wall forming a continuous opening 2127. Nevertheless, an opening 2127 for insertion of the IOL 110 into the recesses 2104 exists.

Figure 19A:
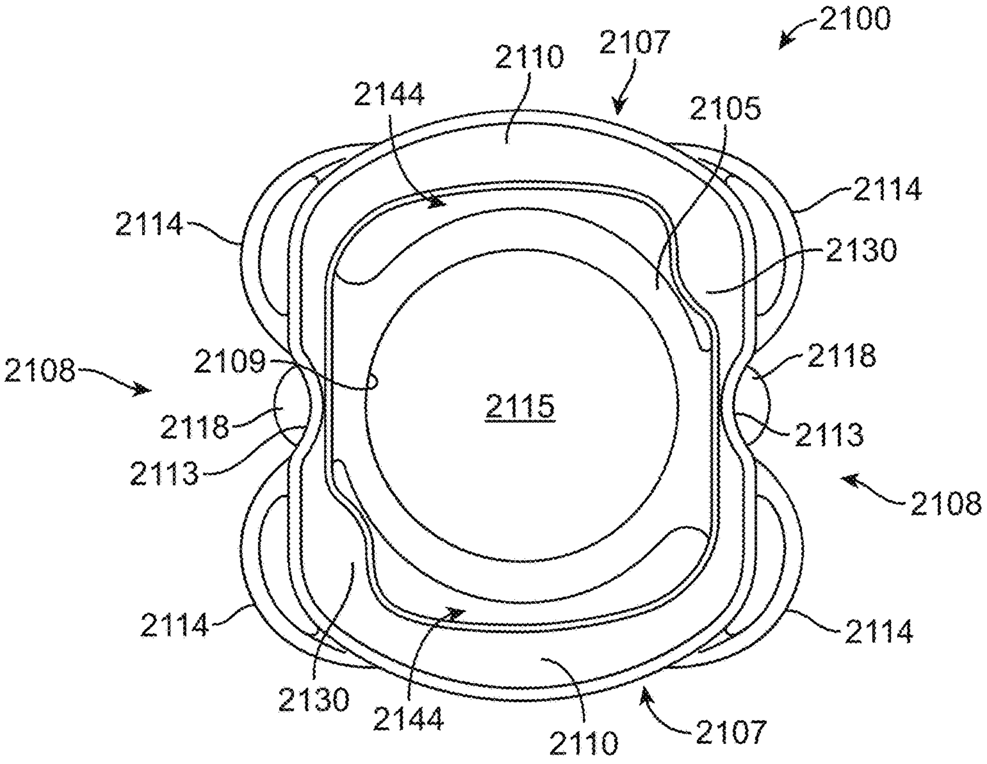
FIGS. 19A-19B show top plan views of interrelated implementations of a device.
Figure 19B:
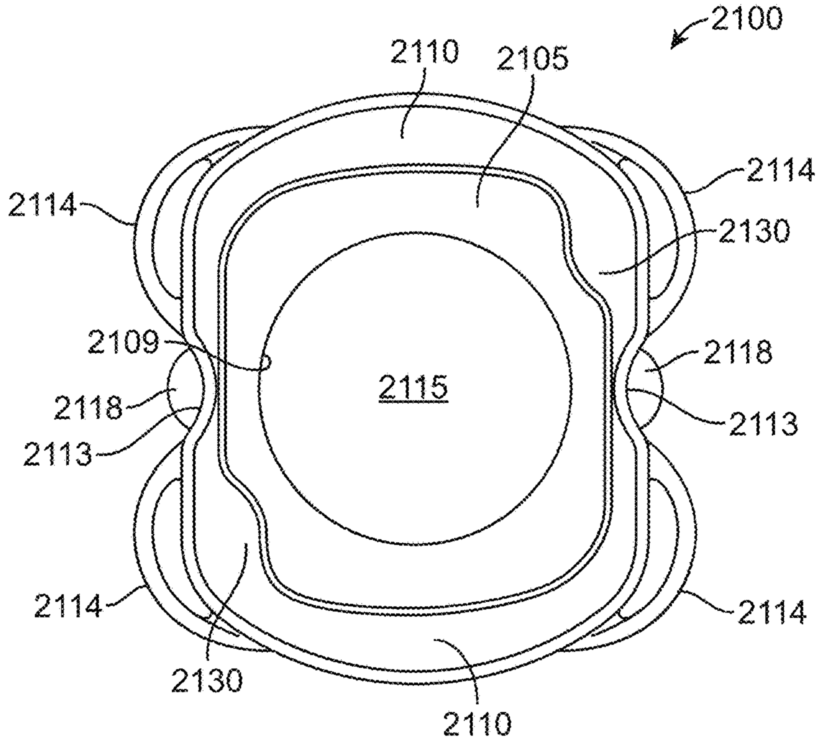

The elongate sides 2108 can be relatively straight or curved. In some implementations, the elongate sides 2108 can incorporate an indentation 2113 that curves inward near a middle of the elongate sides 2108 (see FIGS. 19A-19B). The indentation 2113 can be positioned between the location of the bumpers 2114. The indentation 2113 can have a radius of curvature inward that mirrors the bumpers' radius of curvature outward providing an overall S-shaped curvature to each elongate side 2108 when viewed from above. The indentations 2113 of the side walls 2112 on the elongate sides 2108 provide an hour-glass shape to the chassis.

In some implementations, the distance the awnings 2110 project away from the posterior platform 2105 is asymmetric. For example, a first awning 2110 or a first portion of the awning 2110 can project away from its respective side wall 2112 a first distance. A second awning 2110 or a second portion of the awning 2110 can project away from its side wall 2112 a second distance that is different from the first distance. This asymmetry can allow for easier insertion of a leading haptic 114 or trailing haptic 114 of the IOL 110. The leading haptic 114 can be first inserted under the larger awning 2110 and the trailing haptic 114 can be inserted second under the smaller awning 2110. The anterior opening 2127 defined by the awnings 2110 (and optionally the side walls 2112) can be asymmetric allowing for specific coverage of certain parts of the IOL relative to others, which will be described in more detail below. The awnings 2110 can also have interruptions or discontinuities such as slits or brush-like structures to improve flexibility for each of lens insertion.

The recesses 2104 sized to receive at least a portion of the IOL 110 can be defined by the anterior-facing surface of the posterior platform 2105, the internal surface of the side walls 2112, and the internal surface of the awnings 2110. The height or volume of each recess 2104 can be sufficient to receive a respective one of the haptics 114 or at least a portion of one haptic 114 in both anterior-to-posterior thickness as well as depth or distance away from the central axis CA of the central aperture 2115. The internal surface of the side walls 2112 can additionally serve as a bearing surface for the haptics 114 and provide counter pressure to the haptics to aid in centering the IOL 110 on the device 2100. The awnings 2110 can limit anterior Z-axis movement of the haptics 114 and help to secure the IOL 110 to the device 2100. The reliable fixation of the IOL, including one-piece IOLs, allow for the use of IOLs that require tight centration tolerances (e.g., torics, multi-focal lenses, extended depth of focus (EDOF) IOLs, and accommodating IOLs). The side walls 2112 and awnings 2110 have sufficient arc length to house various haptic designs.

The size of the recess 2104 (e.g., height) between the awnings 2110 and the posterior platform 2105 can vary along the awnings 2110 and in some implementations can be narrower or shorter in at least some regions than an anterior-to-posterior thickness of the IOL haptics 114. As discussed above, the recess height between the anterior-facing surface of the posterior platform 2105 to the inner-facing surface of the awnings 2110 can be between about 0.65 mm to about 0.75 mm. This height need not be constant. A first region of an awning 2110 can project more anteriorly than another region of the same awning 2110 (e.g., a region that covers a terminal end of the haptic 114). The first region of the awning 2110 that is higher can create a wider space sufficient to accommodate the IOL junction (e.g. junction cover 2130). The second region of the awning 2110 that is lower can create a narrower space. The narrower space created by the awnings 2110 can compress the IOL haptics 114 within the space and urge a terminal end of the haptic 114 towards a more posterior position than the haptic 114 is otherwise biased to achieve. As described in more detail below, the posterior platform 2105 can include peripheral cut-outs 2144 arranged to align with the haptics 114 of the IOL 110 when the IOL optic 112 is supported by the posterior platform 2105 (see FIGS. 8A-8E). The cut-outs 2144 are sized and shaped to accommodate the IOL haptic 114 allowing them to sink into the cut-outs 2144 below the level of the anterior-facing surface of the posterior platform 2105. FIG. 8F shows a side elevation view of an implementation of a device 2100.

The wall thickness of the one or more awnings 2110 and/or side walls 2112 can be uniform or non-uniform. In some implementations, the awnings 2110 and/or side walls 2112 can each have a uniform thickness of about 0.35 mm. The material forming the awnings 2110 and/or side walls 2112 can be continuous or discontinuous. Discontinuous material can form a scaffold that minimizes the overall bulk of the device 2100 while still providing protective and/or bearing surfaces for the IOL 110.

As discussed above, the outer region 2111 of the platform 2105 can be substantially non-circular (e.g., rectangular, elliptical, oval, hour-glass, free-form) in shape having a major axis defining the elongate sides 2108 and a minor axis defining the short sides 2107. In contrast, the inner perimeter or inner wall 2109 may define a circular central aperture 2115. In this implementation, the recesses 2104 formed by the awnings 2110 may be positioned opposite one another relative to the major axis so that the span of the IOL 110 haptics 114 may be accommodated within the recesses 2104. The non-circular shape of the outer region 2111 may be a rounded triangle shape having a plurality of lobes projecting outward from a plurality of sides as described elsewhere herein. The awnings 2110 may project out over the anterior-facing surface of the posterior platform 2105 such that they are positioned generally opposite one another. Regardless the orientation, the span of the recesses 2104 defined by the awnings 2110, the side walls 2112, and the posterior platform 2105 is sufficient to accommodate a span of the IOL haptics 114 therebetween. The IOL may be inserted within the recesses 2104 under the awnings 2110 and between the side walls 2112. The diameter between the first and second opposing side walls 2112 is sufficient for IOL insertion. IOLs are typically foldable and therefore the diameter between the first and second awnings 2110 can vary widely. In other implementations, which will be described in more detail below, the platform 2105 can have cutouts 2144 that are so wide that the outer region 2111 of the posterior platform 2105 lies radially inward to the side walls 2112 of the device 2100. This can result in the side walls 2112 of the device 2100 providing a first shape to the device 2100 that is different from a shape of the posterior platform 2105. For example, the side walls 2112 can create a polygonal shape to the device 2100 and the posterior platform 2105 can be generally annular (see FIG. 8C).

Figure 1F:
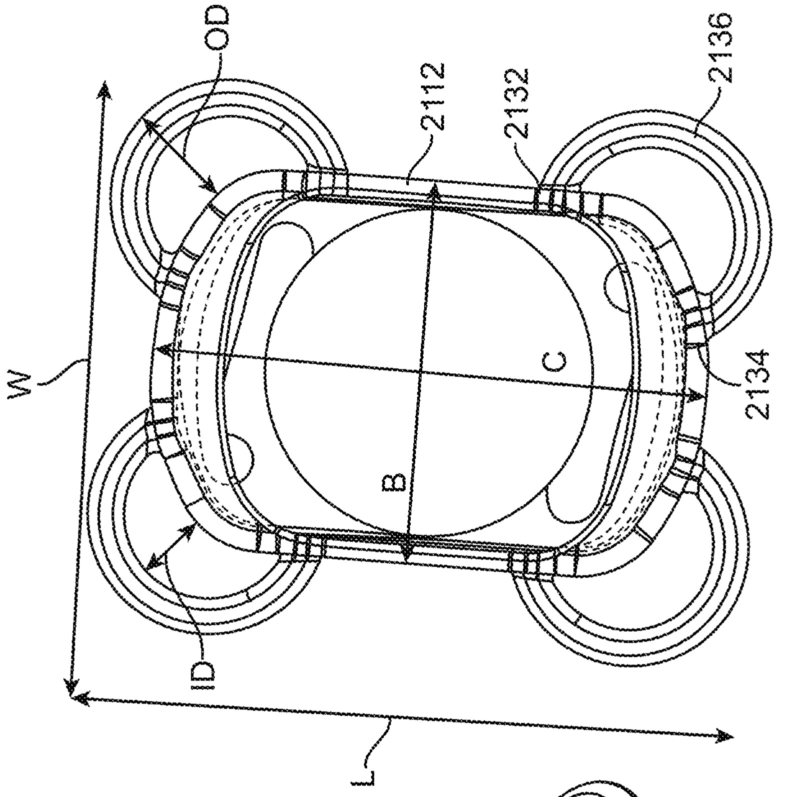
FIGS. 1E-1F are additional views of the device of FIG. 1A-1B.
Figure 1E:
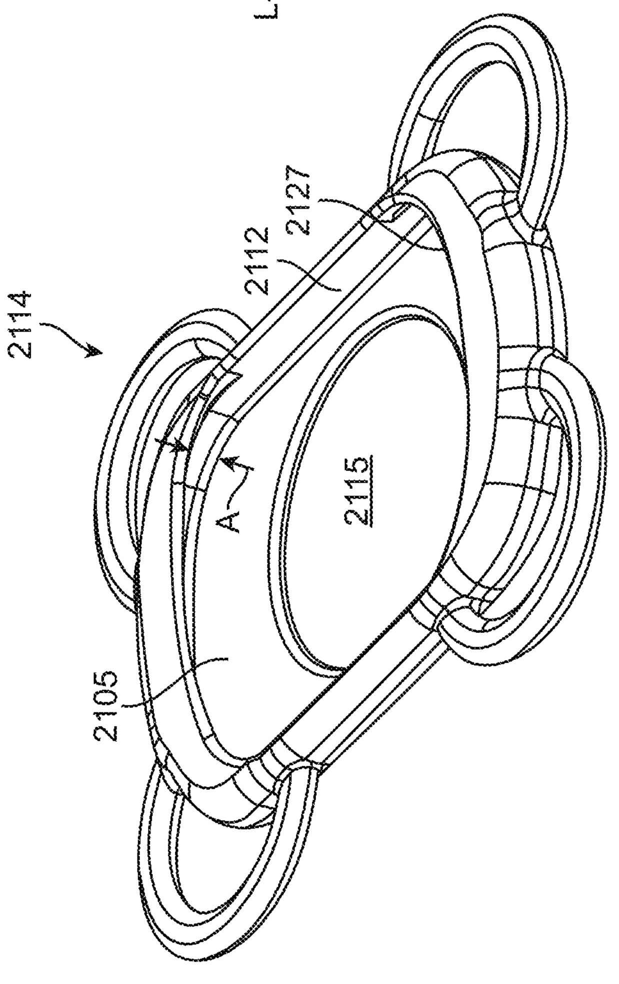

Although the span of the recesses 2104 can accommodate the span of the IOL haptics 114, the span of the recesses may be slightly undersized compared to the span of the IOL haptics 114 so that the haptics 114 are placed under slight compression by the inner bearing surfaces of the side walls 2112. The IOL 110 can rest in a position relative to the device 2100 such that the haptics 114 are at least partially flexed. If the haptics 114 are flexed to severely due to the fit being too tight, the optic 112 of the IOL 110 can become distorted. If the haptics 114 are not in contact with the side walls 2112 due to the fit being too loose, the optic 112 of the IOL 110 may not be stable relative to the device such that it shifts and/or falls out of the device 2100. FIGS. 1E and 1F show the dimensions of the device 2100 to accommodate an IOL 110. The one or more recesses 2105 can be sized to accommodate at least a portion of the IOL 110, for example, along as a thickness aspect within the Z-axis), as an arc length to provide wiggle room for IOL rotation relative to the device 2100 during implantation, or as a width providing a degree of coverage to hide the haptic edge from contacting the iris. The depth of the recesses 2104 between an inner surface of the awnings 2110 and the anterior-facing surface of the platform 2105 (Arrow A in FIG. 1E) can be between about 0.15 mm and about 1.50 mm. The width across the platform 2105 between side walls 2112 along the minor axis (Arrow B of FIG. 1F) can be between about 6.0 and about 11.0. The span between opposing recesses 2104 (Arrow C of FIG. 1F) can be between about 8.0 mm and about 12.5 mm. In another implementation, the length of the platform is about 10.2 mm, the width is about 7.0 mm, and the depth is about 0.60 mm. In further implementations, the platform along the long axis of the device can have an external length of about 9.2 mm and an internal length along the same axis that is about 8.5 mm such that a thickness of the side wall is about 0.7 mm. In still further implementations, the platform along the long axis can be increased to about 11 mm and an internal length along the same axis that is about 9.8 mm. As a result, the side wall is thicker at about 1.2 mm. The increased cavity length can provide more space within which the IOL can be manipulated that, combined with the increased side wall thickness, provides an overall length of the device that is increased. The device can be fixated through the pars plana and thus, posterior to the apex of the ciliary body, such that even if the device on the plane of the ciliary apex is too wide, there can still be space for implanting the larger IOL housing (see FIG. 18H).

The devices described herein are also configured for optic capture techniques. An IOL 110 can be positioned relative to the device 2100 such that the optic 112 of the IOL 110 is urged posterior to a posterior-most surface of the device 2100 while the haptics 114 of the IOL 110 remain anterior to the posterior-most surface of the device 2100. The haptics 114 of the IOL 110 can be positioned within the recesses 2104 of the device 2100 while at least a portion of the optic 112 of the IOL 110 can be urged through the aperture 2115 in the platform 2105 to a posterior side of the device 2100. The edge of the IOL optic can be positioned posterior to the posterior-most surface of the device 2100 while the haptics 114 extend anteriorly through the aperture 2115 such that they remain anterior to the posterior-most surface of the device 2100.

Figure 3:
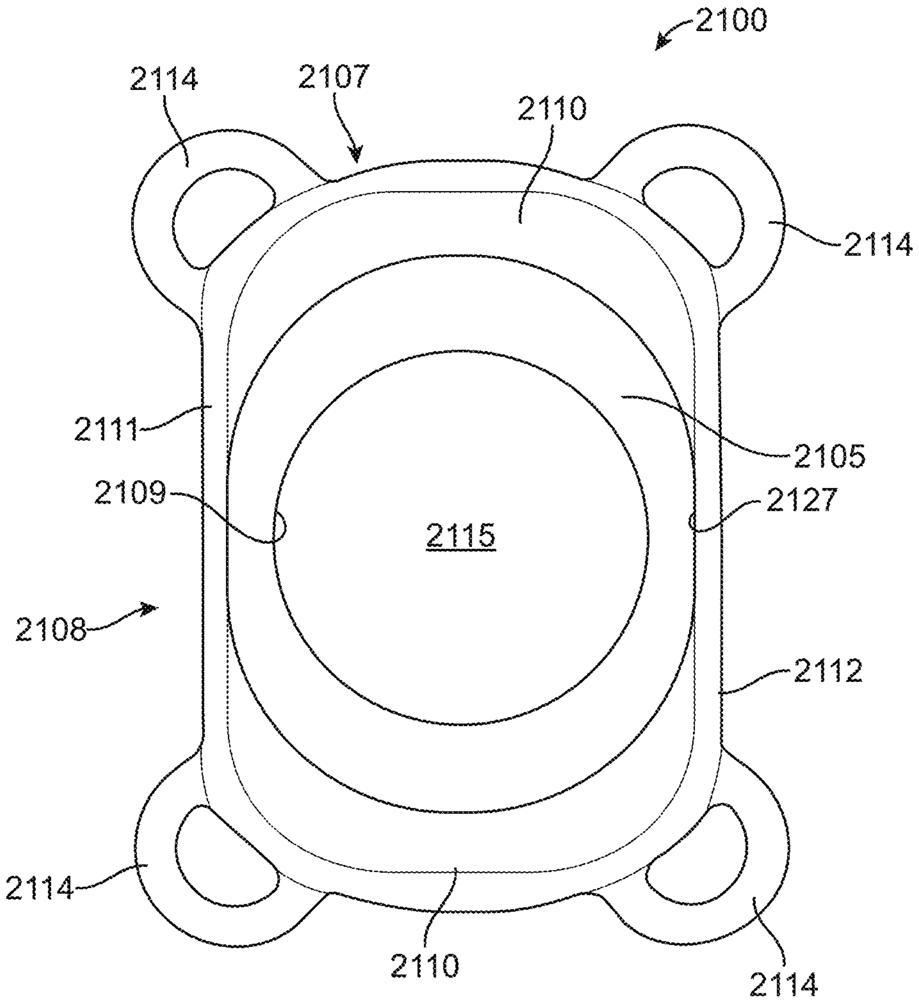
FIG. 3 shows another implementation of a device.

As mentioned above, the anterior opening 2127 can have a diameter that is larger than a diameter of the central aperture 2115 of the posterior platform 2105. FIG. 1A and also FIG. 3 illustrate the central aperture 2115 extending through the posterior platform 2105 visible through the larger anterior opening 2127. The central aperture 2115 is preferably circular, but the anterior opening 2127 need not be circular. FIG. 3 shows a central aperture 2115 that is circular and an anterior opening 2127 that is substantially oval. FIG. 1C shows a circular central aperture 2115 and an anterior opening 2127 that is substantially rectangular. The anterior opening 2127 can have any of a variety of geometric or free-form shapes. In some implementations, the anterior opening 2127 can incorporate one or more out-croppings configured to extend over and cover selected areas of the IOL 110, as will be described in more detail below. The anterior opening 2127 can also incorporate one or more centrally-extending features to directly visualize the device 2100 through the pupil during implantation even if the pupil narrows in size mid-surgery. The centrally-extending features can project to define at least one narrower diameter around the circumference of the anterior opening 2127 that is less than about 7 mm down to about 5 mm, preferably about 6 mm. The centrally-extending features will be discussed in more detail below with respect to FIGS. 18E-18J.

The anterior opening 2127 can be greater than about 6 mm so that the IOL can be manipulated into place and fully unfurl into position with the recesses 2104. The diameter of the anterior opening 2127 can be greater than 6 mm up to about 8 mm. FIG. 1C illustrates a substantially rectangular anterior opening 2127 having a width between the side walls 2112 along Arrow A and a length between the awnings 2110 along Arrow C. The width and the length can be between about 5 mm and about 10 mm. For the generally rectangular-shaped opening 2127, the length is greater than the width. The dimension along Arrow B in FIG. 1C can also be between 5 mm and 10 mm. For the scenario where the dimension is 5 mm all around, the side walls 2112 and awnings 2110 mimic the anterior capsular and the anterior opening 2127 mimics a capsulorhexis and only the central optic 112 of the IOL 110 is exposed through the anterior opening 2127. Preferably, the anterior opening 2127 is larger than this such that the width along Arrow A in FIG. 1C is about 6.25 mm, the length along Arrow C in FIG. 1C is about 7.5 mm, and the dimension across Arrow B in FIG. 1C is about 8.0 mm.

Figure 5A:
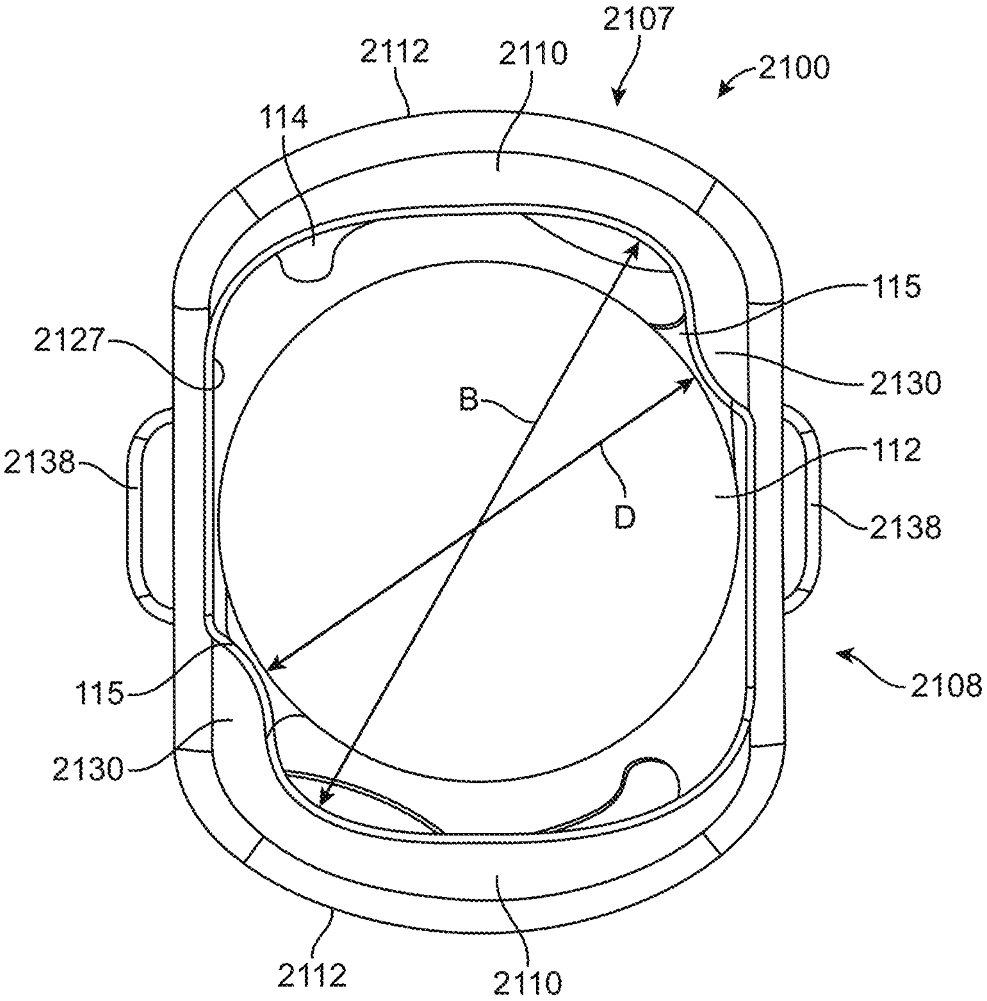
FIG. 5A is a top down view of another implementation of a device.

As discussed above, the anterior opening 2127 can be relatively large all around and the awnings 2110 sized to receive the outer perimeter region of the haptics 114 of the IOL 110. This large size of the anterior opening 2127 ensures the device 2100 can accept nearly universally any of a variety of IOLs. This large size that makes insertion of the IOL 110 easier can also leave certain parts of the IOL 110 exposed through the anterior opening 2127 that one might prefer to cover when implanted anterior to the capsular bag. FIG. 5A shows an implementation of a device 2100 having an anterior opening 2127 defined by a pair of awnings 2110 and a pair of junction covers 2130. In this implementation, the device 2100 has a substantially rectangular or hour-glass shape and the awnings 2110 project over the posterior platform 2105 from the side walls 2112 at each of the short sides 2107 of the rectangle. A first junction cover 2130 can be located near a first corner of the device projecting out from the side wall 2112 near where a first elongate side 2108 meets a first short side 2107. A second junction cover 2130 can be located near an opposite corner of the device projecting out from the opposite side wall 2112 near where the opposite elongate side 2108 meets the opposite short side 2107. This arrangement ensures the junction covers 2130 extend out from the side walls 2112 over a location of a primary hinge point of the haptic 114 and/or the junction 115 where the haptic 114 connects to the optic 112 of the IOL 110. The presence of the junction covers 2130 provides a free-form shape to the anterior opening 2127. The anterior opening 2127 can have a larger opening dimension along Arrow B in FIG. 5A and a smaller opening dimension along Arrow D in FIG. 5A. The IOL 110 can be inserted through the anterior opening 2127 along a first orientation to take advantage of the larger opening dimension along Arrow B. The IOL 110 can be rotated around the central axis CA a distance towards Arrow D once positioned through the anterior opening 2127 to ensure the haptic junction 115 is covered by junction covers 2130 and to ensure fixation of the IOL 110 against the platform 2105. The size of the awnings 2110 can be minimized and the size of the anterior opening 2127 maximized by the presence of the junction covers 2130.

As mentioned above, the device 2100 can include a stabilization feature provided by a plurality of radially extending structures coupled to the body portion. The radially extending structures or bumpers 2114 provide a radially outermost portion of the device to assist in centration of the device 2100 within the eye and providing sutureless positioning of the device within the eye, such as the posterior chamber. In some implementations, the device 2100 is configured to be implanted so that the posterior-facing surface of the posterior platform 2105 abuts against the anterior segment 34 of the capsular bag so that the capsular bag can provide Z-axis support for the device 2100 (see FIG. 2A). The bumpers 2114 can extend outward from the device to provide X-axis and Y-axis support for the device 2100 and aid in preventing rotation of the device 2100 within the Z plane. The ciliary body 15 has a substantially circular or elliptical shape, with the vertical axis being 0.5 mm longer than the horizontal axis on average. A substantially round or elliptical device 2100 can provide centration with the similarly round or elliptical ciliary body. However, matching of the shapes to obtain 360 degree contact between the device 2100 and the ciliary body 15 can lead to inflammation or damage, which could negatively impact aqueous production. The bumpers 2114 can project beyond the perimeter of the platform 2105 to provide centration of the device 2100 within the eye without 360 degree contact with the ciliary body 15 or ciliary sulcus 25. In a preferred implementation, the device 2100 has an outer perimeter surface having a substantially non-circular geometry. The platform 2105 can have an outer region 2111 that is substantially rectangular or hour-glass in shape. The bumpers 2114 can extend outward beyond the outer perimeter of the platform 2105 further enhancing this non-circular geometry. For example, the bumpers 2114 in the implementation of the device 2100 shown in FIGS. 1A-1F are positioned at each corner of the rectangular-shaped body portion and are configured to engage the ciliary body 15 and/or ciliary sulcus 25 along less than 360 degrees. The non-circular outer geometry of the device 2100 can provide centration of the device 2100 without 360 degree contact with the eye tissue along the substantially non-circular shaped outer perimeter surface. The shape of the device 2100 can provide sufficient contact between the bumpers 2114 and the eye tissue (e.g., ciliary body or capsular bag) to aid in centration and support of an IOL 110 without causing inflammation and damage.

The bumpers 2114 can be symmetrically arranged relative to the body portion. The device 2100 can be substantially rectangular in shape and include four bumpers 2114 projecting outward from each corner. The device 2100 can also include just two bumpers 2114 projecting outward from each of the short sides 2107 or from each of the long sides 2108. In still further implementations, the device 2100 can incorporate a single bumper 2114 projecting outward from the device or another number of bumpers 2114 symmetrically arranged around the perimeter of the device 2100. The device 2100 can incorporate any number of bumpers 2114 including 1, 2, 3, 4, or more.

In some implementations, the shape of the bumpers 2114 allows for contact with the eye tissue that is about 120 degrees or less, preferably between 20 and 40 degrees. The contact between each bumper 2114 and neighboring eye tissue can vary depending on bumper configuration and patient anatomy. In some implementations, each bumper 2114 can make contact with eye tissue that is about 5 degrees to about 10 degrees or preferably less than about 30 degrees. A device having more bumpers 2114 may have greater degree of eye tissue contact than a device having fewer bumpers 2114. Minimizing contact between the bumpers 2114 and eye tissues significantly reduces the risk of inflammation or impairment of aqueous production. A substantially non-circular shape of the device, provided in part by the bumpers 2114, allows allow for gentle contact between the device 2100 and the ciliary body that provides centration without requiring an exact match with the patient's specific dimensions. The radius of curvature of the bumpers 2114 can be less than that of the ciliary processes. Thus, the bumpers 2114 can contact the ciliary processes at 1 or 2 or 3 or 4 distinct points rather than across a calculable range. For example, when in use, the substantially non-circular shaped outer perimeter surface of the device 2100 can contact the ciliary processes at these distinct points.

In other implementations, the bumpers 2114 of the device 2100 can be positioned near, but avoid contacting eye tissues (e.g., the ciliary body) once implanted. This arrangement allows for the bumpers 2114 to help in centration of the device. If the device 2100 is positioned too far in one direction, the neighboring bumpers 2114 may abut against the ciliary body during implantation urging the device 2100 away from the ciliary body and promoting the device 2100 into a more central alignment. Once implanted, the bumpers 2114 of the device can be positioned near eye tissue (e.g., the ciliary body) with or without touching the eye tissue. The bumpers 2114 can substantially align a central axis CA of the device 2100 extending through the central aperture 2115 with the visual axis of the eye and allow for the planar surface of the posterior platform 2105 to be stabilized substantially parallel to the Z-plane (vertical plane) of the eye. The central axis CA of the device 2100 need not be perfectly aligned (coincident) with the visual axis of the eye.

The bumpers 2114 can be discontinuous or interrupted structures having one or more openings extending therethrough. For example, the bumper 2114 can be shaped as a portion of a torus or a ring having an inner diameter and an outer diameter. The bumpers 2114 can be coupled to the posterior platform 2105 or the side walls 2112 of the device 2100 such that they project outward a distance away from these regions. Both ends of each bumper 2114 can be coupled to the device 2100 or only one end of each bumper 2114 can be coupled to the device 2100 providing a C-shape to each bumper 2114. Thus, the bumpers 2114 can be closed loop, open loop, plate, Kelman, and any of a variety of haptic types with or without one or more apertures extending through them.

In some implementations, the bumpers 2114 create a maximum outer diameter to the device 2100 that is sufficient to provide centration due to contact with the ciliary body and/or ciliary sulcus. In some implementations, the bumpers 2114 are torus-shaped features projecting outward from each corner of the rectangular-shaped posterior platform 2105. The bumper 2114 can have first and second ends 2132, 2134 that project from a region of the body portion, for example, from a side wall 2112, from an outer region 2111 of the posterior platform 2105, or from another external surface of the device, and a middle region 2136 positioned between the ends 2132, 2134 (see FIG. 1F). Each bumper 2114 can have a radial cross-section that is between about 1.10 mm to about 1.0 mm and an axial cross-section that is between about 0.1 mm to about 1.0 mm, or between about 0.2 mm to about 0.4 mm. In some implementations, the axial cross-section is sized to allow the bumper 2114 to insert within the ciliary sulcus. The distance each bumper 2114 projects beyond its side wall 2112 of the body portion can vary. Each bumper 2114 can have an inside diameter ID measured from the external surface of the side wall 2112 to an inner surface of the middle region 2136 of the bumper 2114. The inside diameter can be between about 0.25 mm and about 3.0 mm. Each bumper 2114 can have an outside diameter OD measured from the external surface of the side wall 2112 to an outer surface of the middle region 2136 of the bumper 2114. The outside diameter can define the maximum outer diameter of the device 21000 created by the bumpers 2114. This maximum outside diameter can be between about 12.5 mm to about 16.0 mm or between 9.0 mm and about 13.0 mm. The device 2100 is configured to be positioned in the posterior chamber. The bumpers 2114 can, but need not, be positioned within the ciliary sulcus during use. In some implementations, the bumpers 2114 can define a maximum outside diameter sized to insert within the ciliary sulcus when the device is centered around the visual axis. In other implementations, the bumpers 2114 can define a maximum outside diameter sized to remain outside of the ciliary sulcus when centered around the visual axis. The bumpers 2114 projecting from a perimeter of the device can be sized so that they abut or lightly touch the ciliary tissue to limit rotation. The bumpers 2114 may also potentially help with centration of the device. For example, the bumpers 2114 may be thin and positioned relatively more posterior so that they aid in centration, but without projecting into the ciliary sulcus while the device 2100 is implanted in the eye.

In an implementation, a length (arrow L of FIG. 1F) of the device 2100 between an outer surface of the bumpers 2114 on a short side 2107 to an outer surface of the bumpers 2114 on the opposite short side 2107 can be between about 6 mm to about 12 mm. A width (arrow W of FIG. 1F) of the device 2100 between an outer surface of the bumpers 2114 on an elongate side 2108 to an outer surface of the bumpers 2114 on the opposite elongate side 2108 can be between about 7 mm to about 14 mm. The bumpers 2114 can project outward a distance that allows the bumpers 2114 rather than the side walls 2112 or the posterior platform 2105 of the device 2100 to make contact with ciliary tissues to provide centration and prevent rotation. FIGS. 2A-2B illustrate the projection of the bumpers 2114 into the ciliary sulcus 25 while the body portion formed by the posterior platform 2105, the side walls 2112, and the awnings 2110 remain substantially within the space defined by the ciliary body 15, preferably without abutting against the ciliary body 15.

The bumpers 2114 can urge the device 2100 away from the adjacent eye tissue upon contact. The discontinuity of the bumper (i.e., the inner volume defined by the inner diameter of the torus) provides the bumper 2114 with a higher degree of flexibility and spring when the outer diameter abuts against eye tissue compared to a solid piece of material. In some implementations, the bumper 2114 can deform slightly or collapse slightly inward upon coming into contact with a ciliary structure. The deformation of the bumper 2114 can be temporary so that the bumpers 2114 return to their original shape thereby urging the device 2100 away from the eye tissue and back towards a centralized position within the eye. Compression of the bumpers does not negatively affect performance of the device 2100. Meaning, one or more of the bumpers 2114 can be compressed while the remainder of the device 2100 provides proper IOL capture, centration, tilt, etc.

The bumpers 2114 can project sufficiently away from the outer region of the device such that they are positioned near, but preferably avoid remaining in contact with the ciliary structures once the device 2100 is implanted. The bumpers 2114 can act as a guide during positioning of the device 2100 within the eye and prevent displacement within the Z-plane to maintain proper alignment between the central aperture 2115 and the eye's visual axis during implantation. The smooth, convex outer surfaces of the bumpers 2114 due to the torus or rounded ring shape having no square edges also ensures the contact between the eye tissue and the bumper 2114 is atraumatic. The bumpers 2114 have a minimal thickness anterior-to-posterior (i.e., axial cross-section) to limit interaction with the iris to avoid synechia and angle closure.

Figure 4A:
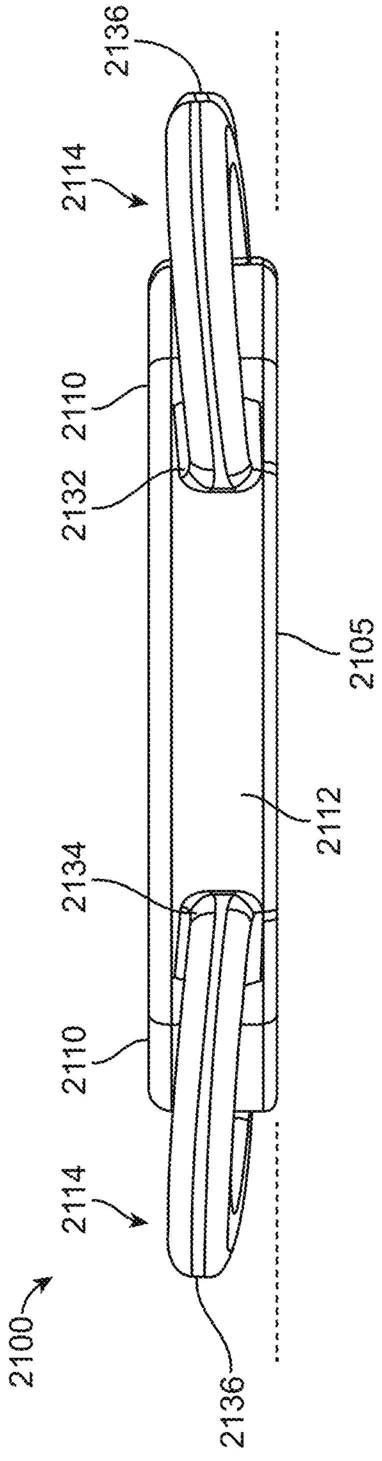
FIGS. 4A and 4B are side and perspective views, respectively, of an implementation of a device.
Figure 4B:
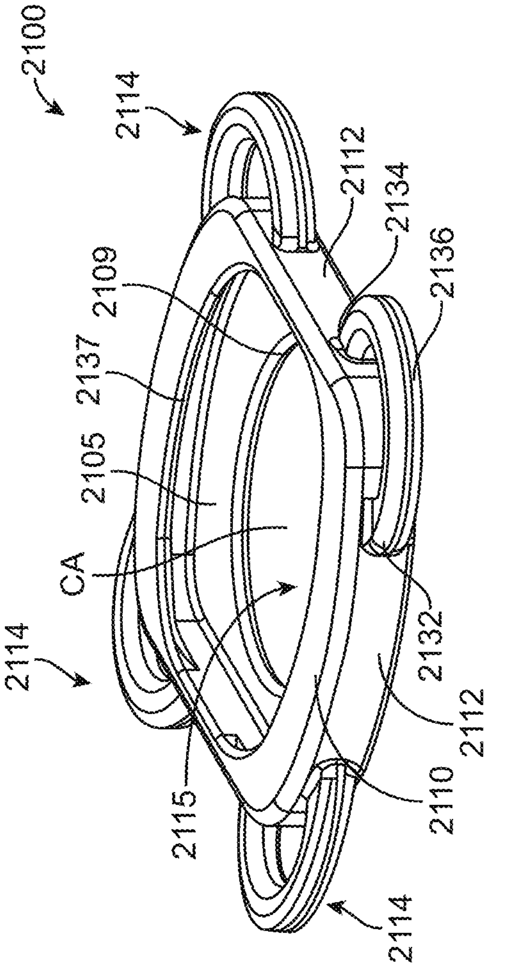

FIGS. 4A-4B illustrate an implementation of the bumpers 2114 that are angled with anterior bias to keep the device 2100 and the IOL 110 posterior of the iris. As mentioned, each bumper 2114 can be a torus-shaped feature projecting outward from the device 2100. The first and second ends 2132, 2134 of the bumper 2114 can be positioned more posteriorly than the middle portion 2136 of each bumper 2114, which extends slightly anteriorly. The middle portion 2136 of each bumper 2114 can make contact with eye tissue and due to this slight anterior bias cause the remainder of the device 2100 to be urged in a more posterior direction and helping to avoid iris touch and chafing. In some implementations, the bumpers 2114 can project from an anterior surface of the device 2100 or can be angled so that the middle portion of each bumper 2114 projects anterior to the anterior surface of the device 2100 formed by the awnings 2110. The device 2100 can be driven posteriorly when one or more of the bumpers 2114 is compressed due to the angle of the bumpers 2114. Additionally, one or more surfaces of the bumpers 2114 can be textured or incorporate features to increase friction with the ciliary process or ciliary sulcus to limit rotation of the device 2100 relative to the eye.

The device 2100 can alternatively or additionally include one or more stabilization features 2138 that can be positioned posteriorly or anteriorly relative to the one or more recesses 2104 of the body portion, the body portion formed by the posterior platform 2105, the side walls 2112, and the awnings 2110. FIGS. 5A-5C, 6A-6E, FIGS. 8A-8F, 9A-9B, 18B-18D and 19A-19B show implementations of devices having a posterior stabilization feature 2138 positioned posterior to the recess 2104. FIGS. 10A-10D show implementations of devices having an anterior stabilization feature 2138 positioned anterior to the recess 2104. The various implementations of devices will be described in more detail below.

The stabilization feature 2138 can project posteriorly from the posterior-facing surface 2140 of the posterior platform 2105 and can project laterally outward along the posterior-facing surface 2140 defining a space 2142 within which the anterior segment 35 of the capsular bag around the capsulorhexis 40 may be positioned. The stabilization feature 2138 is configured to be positioned posterior to the anterior capsule 35 while the remainder of the device 2100 lies anterior to the capsular bag, which provides Z-axis support. The stabilization feature 2138 can engage the capsulorhexis 40 in the anterior capsule 35 to prevent inadvertent movements of the device 2100 once the device is implanted. The stabilization feature 2138 can align the central axis CA of the device 2100 relative to the capsular bag 35 to ensure proper positioning of the optic 112 of the IOL 110 engaged with the device 2100 relative to the visual axis of the eye.

The configuration of the stabilization feature 2138 can vary. The stabilization feature 2138 can include open loops, closed loops, plates, wings, continuous oval feature, flexible finger-like projections, or other configuration. Generally, the stabilization feature 2138 includes one or more projections configured to insert through the capsulorhexis 40 and engage with an inner surface of the anterior segment of the capsular bag 35 so that the posterior-facing surface 2140 of the posterior platform 2105 is affixed against the anterior external surface of the capsular bag 35. Any of a variety of structures are considered herein for the stabilization feature 2138 that can provide both a posterior projecting surface configured to engage the capsulorhexis 40 and a peripherally projecting surface that prevents the device 2100 from sliding anteriorly relative to the capsular bag 35.

In an implementation, the stabilization feature 2138 can have a first portion 2116 and a second portion 2118 coupled to and extending laterally outward from the first portion 2116. The first portion 2116 can be positioned near the inner wall 2109 of the posterior platform 2105 defining the central aperture 2115. The first portion 2116 can project a distance posteriorly from the posterior-facing surface 2140 of the platform 2105 thereby defining the size of the space 2142 between the posterior-facing surface 2140 and the second portion 2118. The distance the first portion 2116 projects is sufficient to allow the anterior capsule 35 of the capsular bag to insert between the posterior-facing surface 2140 of the platform 2105 and the second portion 2118 so that the capsulorhexis 40 engages against the first portion 2116. The first portion 2116 can be a ring-shaped structure defining an outer diameter sized to pass through and engage with the anterior capsulorhexis 40. However, the first portion 2116 need not be fully ring-shaped. For example, the first portion 2116 can be formed by a plurality of projections that are arranged on opposite sides of or around the central aperture 2115 (see FIGS. 5B-5C, 6A-6C, and 8A-8F).

The second portion 2118 of the stabilization feature 2138 projecting laterally outward from the first portion 2116 can define an outer diameter that is larger than the outer diameter defined by the first portion 2116. As mentioned, the first portion 2116 is sized to extend within and be received by the capsulorhexis 40. The second portion 2118 is sized to extend a distance inside the capsular bag (or posterior to the anterior segment of the capsular bag in the scenario where there is not complete capsule) and along an inner surface of the anterior capsule 35. Thus, the anterior capsule 35 of the capsular bag can be positioned between the second portion 2118 positioned posterior to the capsular bag and the posterior-facing surface 2140 of the platform 2105 positioned anterior to the capsular bag. The second portions 2118 can be a pair of wings that extend outward in opposite directions away from one another. The second portions 2118 of the stabilization feature 2138 together can project outward a distance beyond the posterior platform 2105 on opposite sides. For example, each of the second portions 2118 can have a length that is greater than a distance between the inner wall 2109 to the outer region 2111 such that each of the second portions 2118 extends a distance beyond the outer region 2111 on opposite sides (see FIG. 5A). The stabilization feature 2138 can have a span along the short axis of the device 2100 that is greater than a span of the posterior platform 2105 along the short axis of the device 2100. Typically, the second portion 2118 projects outward from the perimeter of the posterior platform 2105 in at least two regions, but the second portion 2118 can project outward from one, two, three, or more regions as well as outward from an entire perimeter of the platform 2105. The posterior platform 2105 (and the device 2100) can have any of a variety of shapes, including rounded rectangle, oval, elliptical, triangular, etc. If the posterior platform 2105 has a rectangular or elliptical, or hour-glass shape with elongate sides 2108 and short sides 2107, the second portion 2118 can form two wings projecting outward from each of the elongate sides 2108. The second portions 2118 projecting outward may be at a location that is below the indentation 2113 on the elongate sides 2108. The hour-glass contour provided by the indentations 2113 allows for the stabilization feature 2138 to contact the posterior surface of the device at a certain minimal diameter and extend a certain minimal radial distance, yet still remain visible from a top-down view (see FIGS. 19A-19B). The distance the second portions 2118 extend radially outward can be minimized, which eases the insertion process of the device, but also provides sufficient stability relative to the bag. If the posterior platform 2105 has a triangular shape with three lobes or angles and three sides, the second portion 2118 can form three wings projecting outward from each side of the rounded rectangle between the lobes. If the posterior platform 2105 has a circular shape, the second portion 2118 can project outward along an entire circumference of the circle forming a fully elliptical or circular flange projecting outward and providing 360 degree support and stabilization relative to the anterior capsule. These are some examples of combinations of perimeter shapes and winged projections. Others are considered herein.

The relative position of the stabilization feature 2138 can vary such that the span of the second portions 2118 is along the short axis of the device 2100 or along the long axis of the device. The stabilization feature 2138 shown in FIG. 5A is positioned to project outward from the two elongate sides 2108 of the body portion and are configured to engage with the capsular bag. The stabilization feature 2138 can be arranged so that the wings formed by the second portions 2118 are perpendicular or orthogonal to the opposing recesses 2104 within which the haptics 114 of the IOL 110 insert. In other words, if the opposing recesses 2104 are located on the short sides 2107 of the device 2100, the opposing wings of the stabilization feature 2138 can be located on the elongate sides 2108 of the device 2100. However, the wings of the stabilization feature 2138 can be arranged around the device 2100 in any of a variety of orientations to provide engagement and stability with the anterior capsule 35.

The outer dimension of the second portion 2118 that projects out from the perimeter of the posterior platform 2105 can have any of a variety of shapes including oval, elliptical, rectangular, square, triangular, or other free-form shape. The outer dimension can also curve or projecting along another dimension. For example, the second portion 2118 can lie in a plane parallel to the posterior platform 2105 spaced away a distance equal to the anterior-to-posterior length of the first portion 2116 (see FIG. 5B). Alternatively, the second portion 2118 of the stabilization feature 2138 may also have an angle or curvature or outer elevation configured to engage with an internal surface of the anterior capsule providing posterior bias to the device 2100. The stabilization feature 2138 can have interruptions within these wings projecting outward from the perimeter of the platform 2105. For example, the second portions 2118 positioned inside the capsular bag can include one or more apertures extending through a region of the wing. The apertures or interruptions can also include one or more indentations or grooves or other surface feature near an outer perimeter of the second portions 2118. These can provide for flexibility during handling and also allow fluid such as viscoelastic to escape from inside the bag.

The stabilization feature 2138 can engage with the capsulorhexis 40 to center the device 2100. The capsulorhexis 40 can be between about 4 mm and about 7 mm in diameter, or between about 5 mm and about 6 mm. The first portions 2116 can be spaced away from one another a distance that is at least as large as the diameter of the central aperture 2115 and slightly oversized relative to the capsulorhexis 40. The oversized dimension can place the capsulorhexis 40 under a slight amount of tension for improved fixation of the device 2100 relative to the bag. In an implementation, the capsulorhexis is about 5.5 mm and the outer diameter defined by the first portion 2116, whether fully annular or formed by a pair of projections, can be about 6.0 mm. Other sizes are considered herein.

The posterior-facing surface 2140 of the platform 2105 can abut against the external surface of the anterior capsule 35 of the capsular bag, the first portion 2116 of the stabilization feature 2138 can engage the capsulorhexis 40, and the second portion 2118 of the stabilization feature 2138 can insert within the bag and abut against the internal surface of the anterior capsule 35 of the capsular bag. Z-axis support can be provided by the anterior capsule 35 of the capsular bag and centration of the device 2100 can be provided by engagement between the stabilization feature 2138 and the capsulorhexis 40. The device 2100 need not engage with or contact the ciliary process or ciliary sulcus for centration. The IOL 110 can strengthen the device 2100 and enhance stability of these capsulorhexis-engaging features.

Figure 6A:
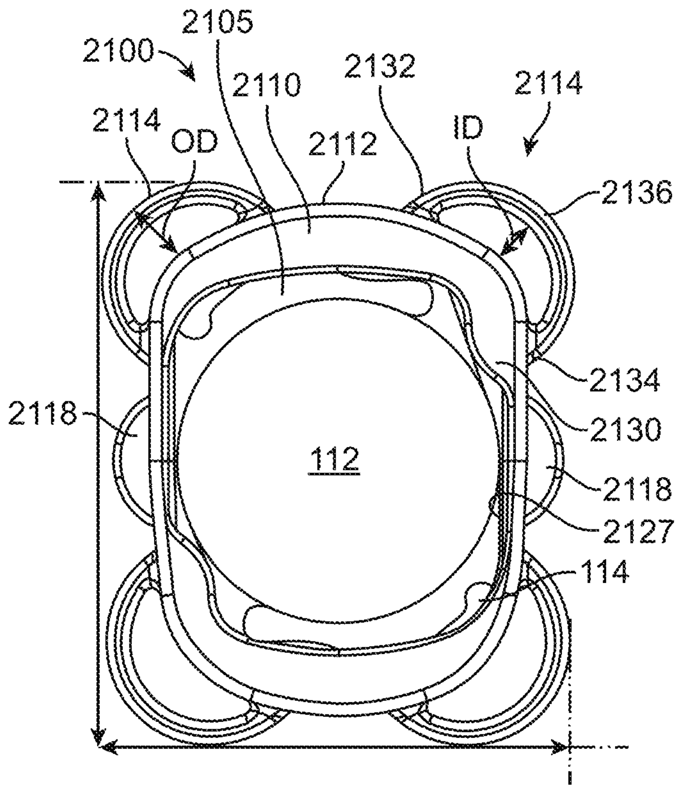
FIGS. 6A-6C show top down, perspective, and cross-sectional views, respectively, of an implementation of the device incorporating a plurality of radially extending bumpers and a posterior stabilization feature.
Figure 6B:
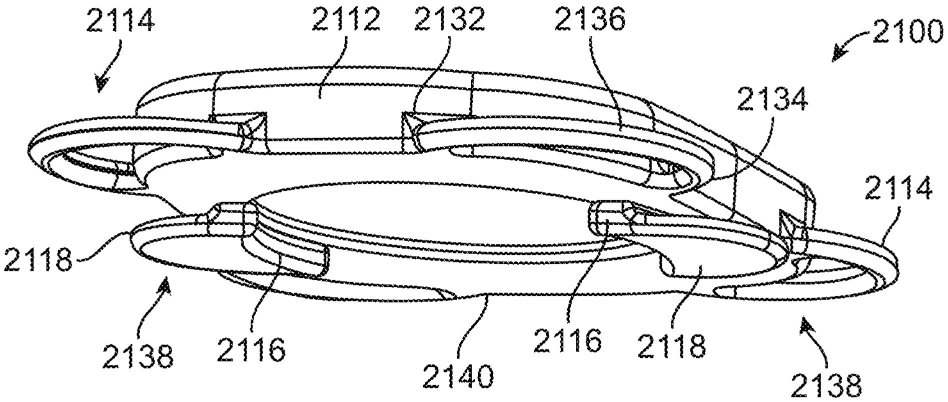

FIGS. 6A-6E show an implementation of the device 2100 having a plurality of bumpers 2114 and a stabilization feature 2138. The posterior platform 2105 has a rounded rectangle shape with four bumpers 2114, each projecting outward from a perimeter of the platform 2105 near a corner of the rectangle. The wings of the second portion 2118 of the stabilization feature 2138 extend outward from the elongate sides 2108 between the bumpers 2114. In this implementation, the wings of the second portion 2118 have a shape that is circular or oval, but it should be appreciated that any of a variety of shapes are considered. FIG. 6B shows a perspective view of the posterior side of the device 2100. The bumpers 2114 project radially outward so that the entire bumper 2114 is generally within a single plane that is parallel to the posterior-facing surface of the platform 2105. The bumpers 2114 can be angled relative to the posterior-facing surface of the platform 2105 as described above so that the middle portion 2136 is positioned more anteriorly than the ends 2132, 2134. The bumper 2114 ends 2132, 2134 are also coupled to a more posterior region of the side walls 2112. The bumper 2114 ends 2132, 2134 may also be coupled to a more anterior region of the side walls 2112. The implementation shown in FIG. 6A also has four bumpers 2114 with each bumper 2114 projecting outward from a corner of the rectangular shaped body portion. It should be appreciated that the device can include two bumpers 2114 projecting outward over the short ends 2107 of the rectangle so that a first end 2132 is coupled to a side wall 2112 near a first elongate side 2108 and a second end 2134 is coupled to a side wall 2112 near the opposite elongate side 2108 so that the middle portion 2136 extends around an entire short side 2107.

Figure 6C:
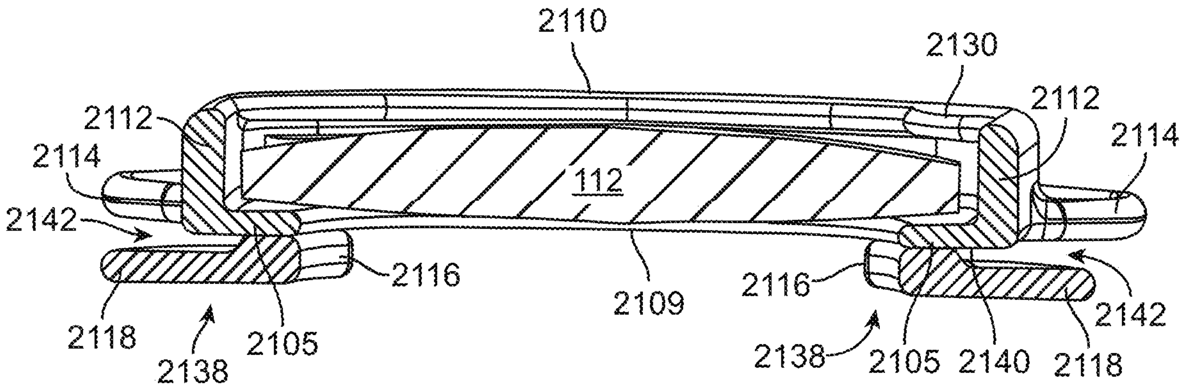
Figure 6D:
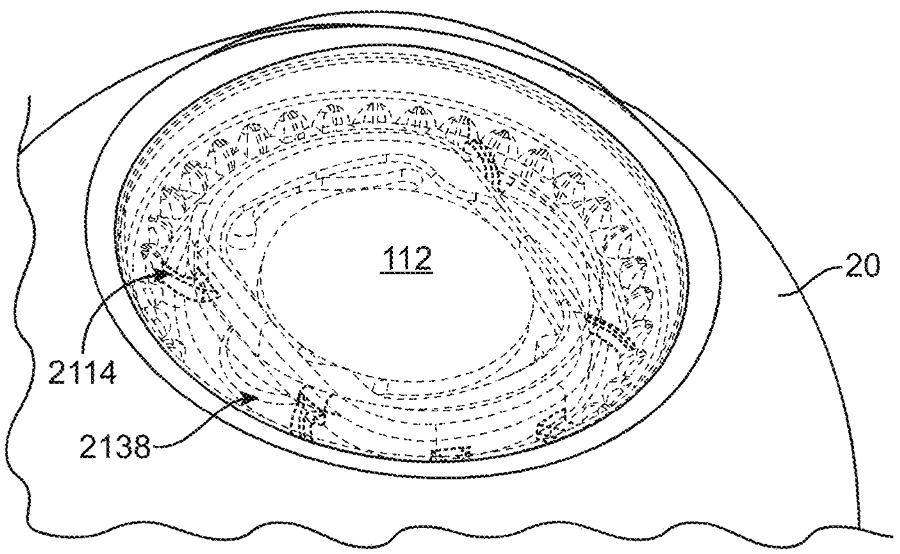
FIG. 6D is a perspective view of the device of FIG. 6A positioned within an eye and visualized through the pupil.
Figure 6E:
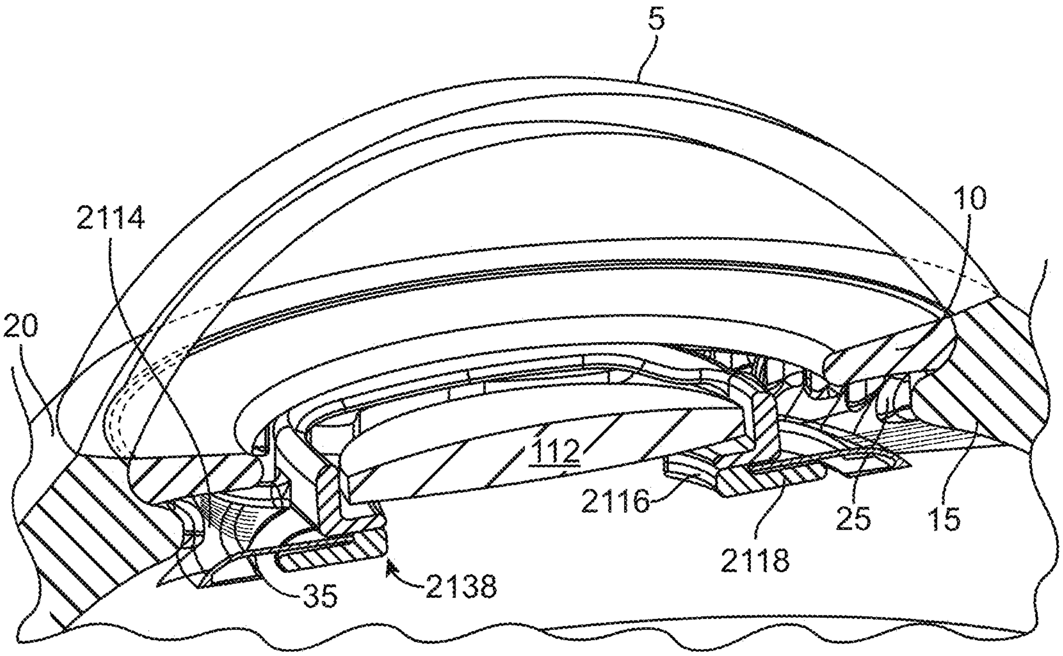
FIG. 6E is a cross-sectional view of the device of FIG. 6A implanted in an eye.

FIGS. 6B-6C illustrate the stabilization feature 2138 projects posteriorly from the posterior-facing surface 2140 of the posterior platform 2105 so that a plane of the wings 2118 is posterior to a plane of the bumpers 2114. This allows for the wings 2118 of the stabilization feature 2138 to be positioned posterior to the anterior segment 35 of the capsular bag while the bumpers 2114 are capable of inserting within the ciliary sulcus 25 (see FIG. 6E). The space 2142 between the wings 2118 and the posterior facing surface 2140 of the posterior platform 2105 can receive the anterior segment 35 within it so that the capsulorhexis 40 surrounds the first portions 2116 of the stabilization feature 2138. FIG. 6E shows the posterior segment of the capsular bag to be missing. The IOL 110 is shown positioned within the body portion, which forms a partial lens housing for the IOL. The optic 112 of the IOL 110 is shown positioned between side walls 2112 and against the anterior-facing surface of the posterior platform 2105 so the optic 112 of the IOL 110 covers the central aperture 2115. The posterior surface 2140 of the posterior platform 2105, the stabilization feature 2138, and the IOL 110 covering the central aperture 2115 can create a barrier between the posterior chamber and the vitreous. The anterior-facing surface of the awning 2110 is positioned posterior to the iris 10. Preferably, the awning 2110 does not contact the iris 10, however, the smooth external surfaces of the awnings 2110 are designed so that in case of contact the iris 10 does not experience damage or irritation. The junction cover 2130 provides additional coverage of the haptic 114 where it forms a junction 115 with the optic 112 of the IOL 110 preventing this region from coming into contact with the iris 10.

The devices 2100 described herein can incorporate any combination of stabilization features. In some implementations, the device 2100 includes a plurality of bumpers 2114 configured to extend towards the ciliary structures and a stabilization feature 2138 arranged more posteriorly to engage with at least a portion of the capsular bag (see FIGS. 6A-6E, 8A-8F, and 9A-9B). In other implementations, the device 2100 includes only a plurality of bumpers 2114 without any stabilization feature 2138 (see FIGS. 1A-1F, 2A-2B, 3, and 4A-4B). In some implementations, the device 2100 includes no bumpers 2114 and stabilization features 2138 arranged more posteriorly relative to the body of the device that are configured to engage with at least a portion of the capsular bag while the body of the device sits anterior to the capsulorhexis (see FIGS. 5A-5C). In still further implementations, the device 2100 includes no bumpers 2114 and stabilization features 2138 arranged more anteriorly relative to the body of the device that are configured to engage with at least a portion of the capsular bag while the body of the device sits posterior to the capsulorhexis (see FIGS. 10A-10D). Some of the devices described herein are configured to be positioned with a majority of the device located anterior to the capsular bag and supported by the anterior segment of the bag. Other devices described herein are configured to be positioned with a majority of the device located within the capsular bag while still supported by the anterior segment (e.g., the capsulorhexis) of the bag. This will be described in more detail below.

Figure 7:
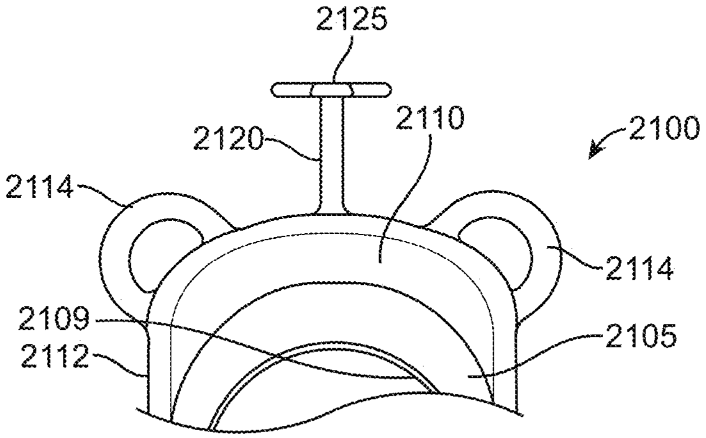
FIG. 7 shows a partial top-down view of an implementation of the device having an anti-rotation fixation arm or tether.

The stabilization features can provide secure positioning relative to the bag and/or the ciliary sulcus to ensure the device 2100 remains fixed against or relative to the anterior segment of the bag. In some implementations, the device 2100 may additionally incorporate a tether 2120 (also referred to herein as a fixation arm) that prevents rotation of the device 2100 around the visual axis within the Z-plane (vertical plane) of the eye. FIG. 7 illustrates an implementation of a device 2100 incorporating a tether 2120 projecting from a side wall 2112. The tether 2120 may project from any of a variety of locations on the device 2100 including alone a short side 2107, an elongate side 2108, or at or near a corner of the device 2100. The tether 2120 may be designed to have a rigidity and length allowing it to behave as a rigid spacing element. A tether 2120 that is rigid or capable of applying a spring force can rely on penetration of adjacent tissue or being wedged into place. Preferably, the tether 2120 is very flexible so that the tether 2120 does not drive centration of the device 2100 and so that the IOL position is not dictated by the patient's scleral diameter. In an implementation, the device 2100 can include a posterior stabilization feature 2138 and a tether 2120 to limit rotation without applying too much counter force. The device can include a single tether 2120 as shown in FIG. 7 or can incorporate one, two, three tethers or fixation arms that are affixed trans-sclerally using an externalized anchor 2125 as described in U.S. application Ser. No. 16/988,519, filed Aug. 7, 2020, which is incorporated herein by reference in its entirety. In other implementations the tether 2120 can be affixed to the iris or another portion of the eye. The anti-rotation tether 2120 can be particularly useful when the device is intended to be used with a toric IOL where the slightest amount of rotation around the visual axis results in severe distortions. The tethers 2120 can provide artificial zonular fixation stabilizing the device.

The device can include at least three fixation arms 2120 that are configured to be placed under tension to locate and stabilize the device within the eye. Each of the three fixation arms 2120 can extend outward from a respective one of the plurality of sides. One or more of the fixation arms 2120 can be substantially straight between their origin 2103 with the support structure and their terminal ends 2102. The straight fixation arm or leading fixation arm 2120 can extend along a single longitudinal axis L between the origin and the terminal end without any bends or curves away from the single longitudinal axis L (see FIG. 7). The straight fixation arm can extend orthogonal to the outer perimeter surface of the support structure outer wall. The longitudinal axis L of the straight fixation arm(s) can be positioned orthogonal to the outer perimeter surface of the outer wall. The plane of the anterior-facing surface of the support structure and the longitudinal axis L of the straight fixation arm(s) can be parallel to one another as can the plane of the posterior-facing surface of the support structure and the longitudinal axis L. Interrelated implementations of the device 2100 having a plurality of fixation arms 2120 are described in more detail below with respect to FIGS. 11A-11F, 12A-12C, 13A-13E, 14, 15, 16A-16C, 17, 18A-18D, 18E-18H, and 18I-18J.

Figure 8A:
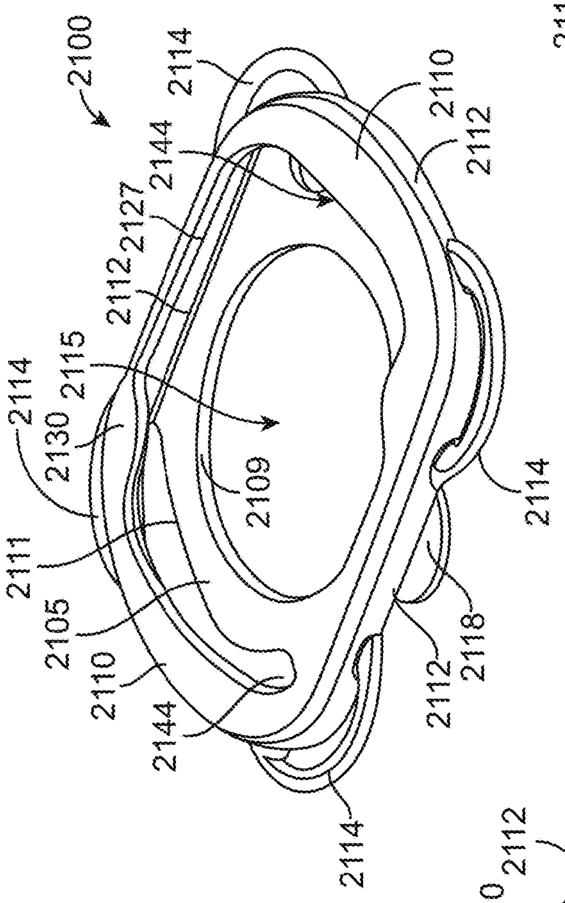
FIGS. 8A-8C are perspective views of an interrelated implementation of a device.
Figure 8C:
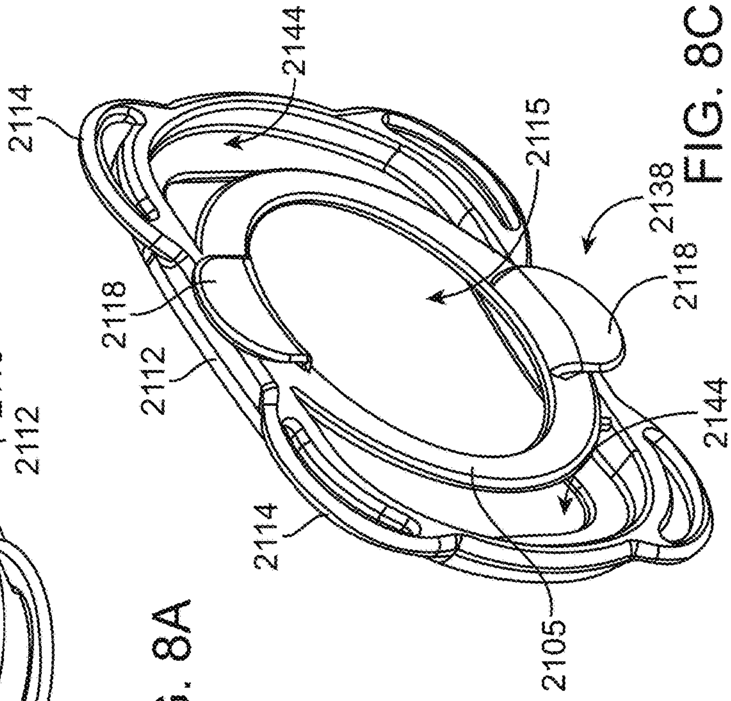
Figure 8B:
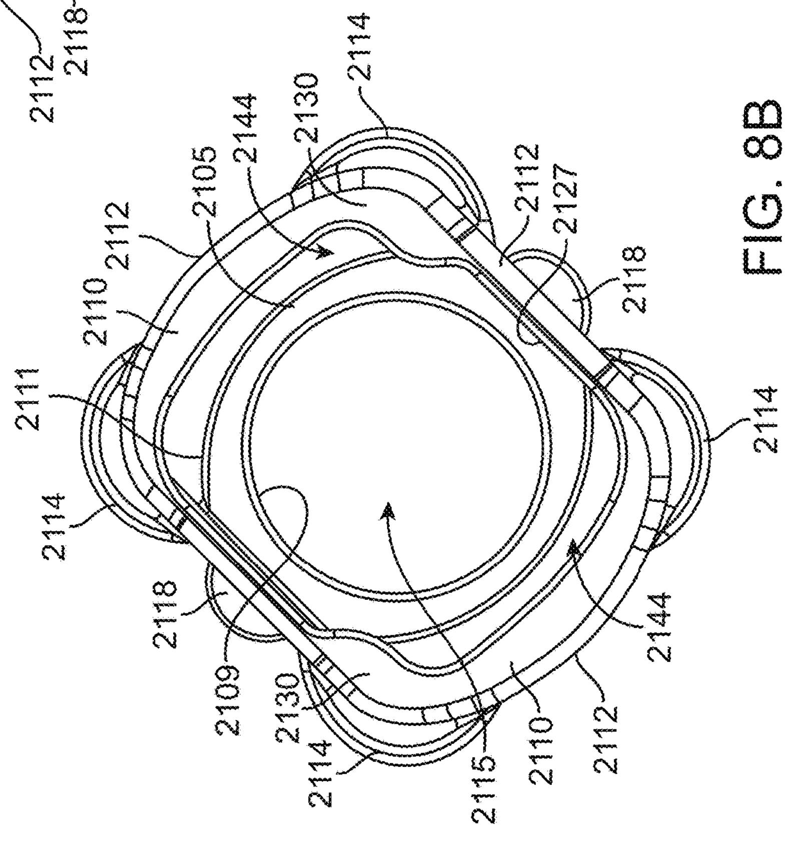
Figure 8E:
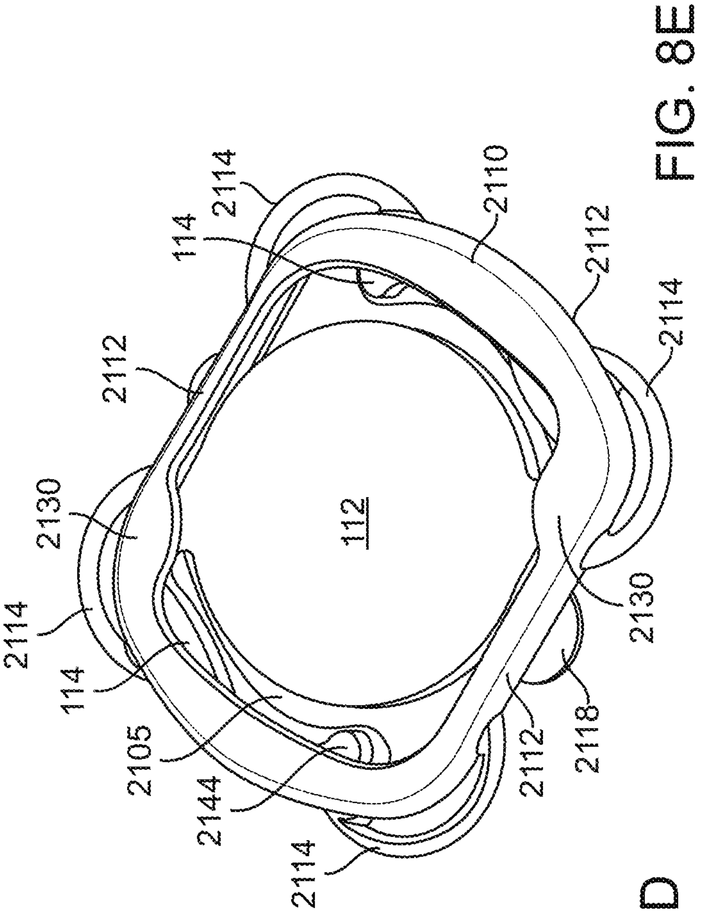
FIGS. 8D-8E are bottom and top views, respectively, of the device of FIG. 8A supporting an intraocular lens.
Figure 8D:
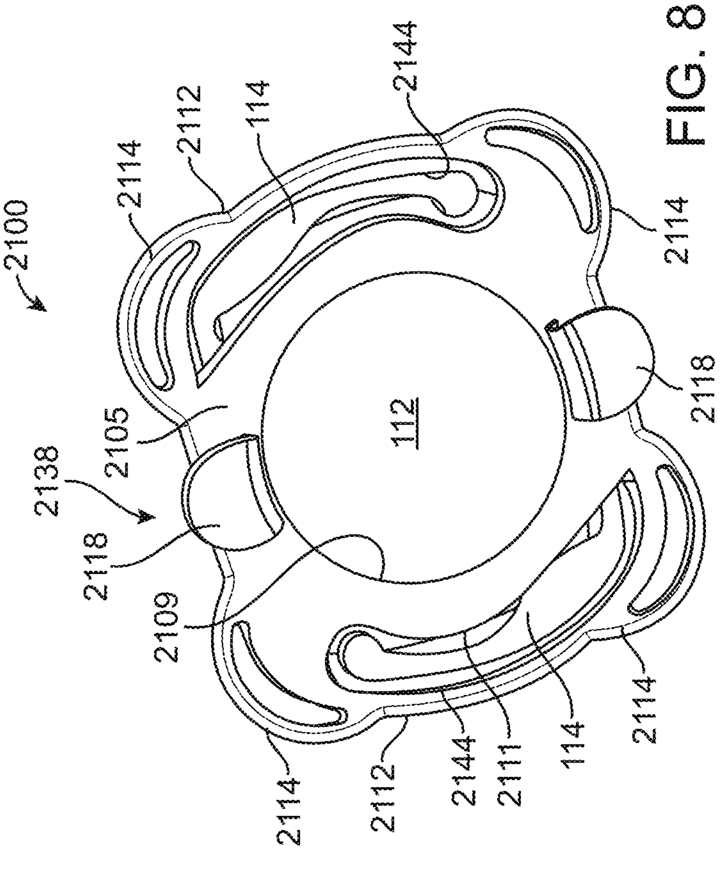
Figure 8F:
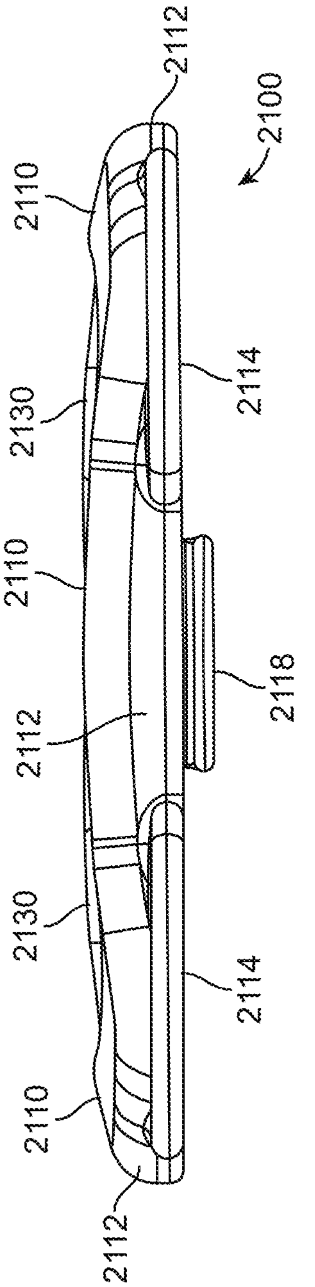
FIG. 8F is a side view of an interrelated implementation of a device.

FIG. 8A shows an implementation of a device 2100 having a posterior platform 2105 with a central aperture 2115 and peripheral cut-outs 2144. FIG. 8E shows the device 2100 of FIG. 8A with an IOL 110 positioned within in the body and FIG. 8D shows a posterior side of the device 2100 and the relative arrangement of the peripheral cut-outs 2144 and the haptics 114 of the IOL 110. The peripheral cut-outs 2144 minimize the bulk of the device as well as allowing for overall reduced thickness anterior-to-posterior. The device 2100 can be positioned within the posterior chamber of an eye anterior to the capsular bag. The anterior-to-posterior thickness of the device 2100 is important in whether the device 2100 interacts with a posterior surface of the iris. Minimizing the anterior-to-posterior thickness of the device 2100 limits the interaction between the device 2100 and the iris. The posterior platform 2105 can have two peripheral cut-outs 2144, one cut-out 2144 can be positioned along a first short side 2107 of the device 2100 and a second cut-out 2144 can be positioned along the second opposite short side 2107. This arrangement positions each cut-out 2144 below a location of the IOL haptics 114 when the IOL 110 is positioned within the device 2100. Each cut-out 2144 can be relatively elongate such that a length of the cut-out 2144 extends a length that is about the length of the short side 2107. For example, the cut-out 2144 can extend from a corner of the device where the short side 2107 and a first long side 2108 meet toward the other corner where that short side 2107 meets the opposite long side 2108. The width of the cut-out 2144 can vary along its length so that the width of the cut-out 2144 is wider at a first corner and narrower at the opposite corner. The cut-out 2144 can be wider on the corner of the device where the IOL junction lies and narrower on the corner of the device where the ends of the haptics lie. The shape of the cut-outs 2144 is defined by the outer wall 2111 of the posterior platform 2105 and the posterior facing surface of the side walls 2112. The outer wall 211 can define a first side of the cut-out 2144 and the posterior-facing surface of the side walls 2112 of the device can define an opposing side of the cut-out 2144. The overall shape of the cut-out 2144 can be similar to a shape of the IOL haptic 114. The narrower end of the cut-out 2144 can be sized and shaped to receive the terminal end regions of the haptics 114 while the wider end of the cut-out 2144 can be near where the haptic 114 joins the optic 112 (see FIG. 8D). The cut-outs 2144 allow for the terminal end regions of the flexible IOL haptics 114 to be urged in a posterior direction towards the region of the cut-outs 2144 by, for example, the awnings 2110. The presence of the cut-outs 2144 can create a curved outer wall 2111 to the posterior platform 2105 that together with the circular inner wall 2109 forming the central aperture 2115 creates an annular shape to the posterior platform 2105. In some implementations, the cut-outs 2144 can be so wide that the outer region 2111 of the posterior platform 2105 lies radially inward to the side walls 2112 of the device. This can result in the side walls 2112 of the device 2100 having a first shape and the posterior platform 2105 of the device 2100 having a second, different shape. For example, the side walls 2112 can create a rectangular or polygonal shape to the device 2100 and the posterior platform 2105 is generally annular in shape. FIG. 8D shows the side walls 2112 of the device 2100 create a substantially rectangular or square shape whereas the shape of the posterior platform 2105 created by the cut-outs 2144 is more annular. FIGS. 8B-8C illustrate another implementation of the device 2100. The cut-outs 2144 are larger in size relative to the cut-outs 2144 in FIG. 8D creating a more annular shaped posterior platform 2105. Regardless the overall size of the cut-out 2144 to accommodate the haptics 114, the posterior platform 2105 is sized to support the central optic 112.

Figure 9B:
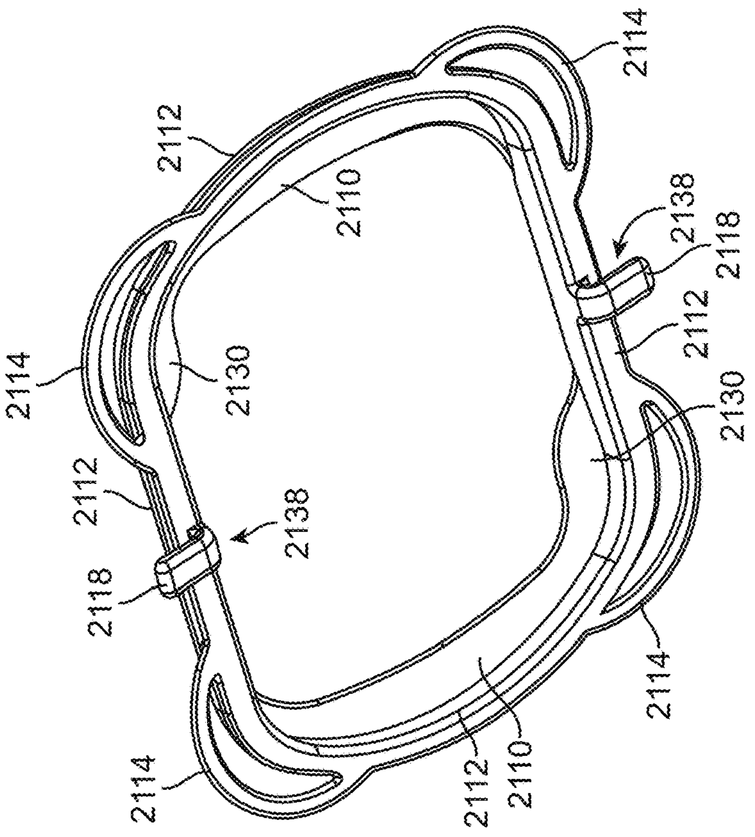
FIGS. 9A-9B are top and bottom views, respectively, of an interrelated implementation of a device.
Figure 9A:
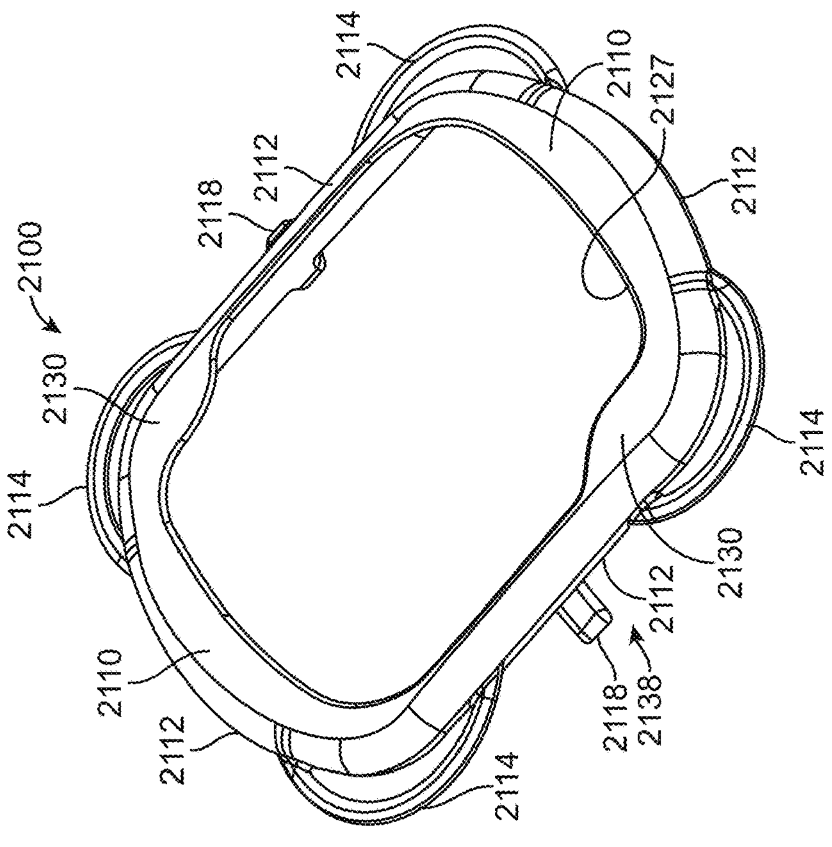

In some implementations, the device 2100 has no posterior support 2105 and instead uses the anterior capsular bag to support the central optic 112. FIGS. 9A-9B shows a device 2100 having side walls 2112 that curve inward to form awnings 2110 forming anterior-facing surface of the device 2100. The awnings 2110 in combination with the side walls 2112 create a body portion defining an internal recessed region within which an IOL 110 can be positioned. The body portion helps to position and fix the IOL 110 within the device 2100 while protecting the surrounding eye tissue. The device 2100 is configured to be positioned against the anterior segment of the capsular bag between the anterior capsular segment and the iris within the posterior chamber and over a capsulorhexis. The anterior capsular segment in this implementation is preferably intact. The anterior segment of the capsular bag can provide Z-axis support for the IOL positioned behind the awnings 2110. The one or more bumpers 2114 project outward from the side walls 2112 so as to atraumatically contact ciliary eye tissues such as the ciliary body or the ciliary sulcus to provide centration of the device 2100 and anti-rotation.

In the embodiment of the device shown in FIGS. 9A-9B, posterior-facing surfaces of the side walls 2112 form a posterior surface of the device 2100 forming a partial shell for the IOL. As with other implementations described herein, the device 2100 can be implanted so that the body of the device 2100 remains anterior to the capsulorhexis and the stabilization feature 2138 extends posterior to the capsulorhexis. The bumpers 2114 can extend outward from the side walls 2112 toward the ciliary sulcus. Because the device lacks a posterior platform 2105, posterior-facing surfaces of the IOL remain exposed on a posterior end of the device 2100. Thus, the IOL can make contact, for example, with at least a portion of the anterior segment of the capsular bag when positioned within the device 2100 implanted in the eye. Anterior-facing surfaces of the IOL are at least partially covered by the awnings 2110 and junction covers 2130 of the device 2100 thereby protecting the iris from any square edges of the IOL 110. The stabilization feature 2138 can project posteriorly from the device and include laterally-extending portions 2118 as described elsewhere herein. When the device 2100 is positioned in the edge, edges of the capsulorhexis can extend over portions 2118 so that they are positioned posterior to the capsulorhexis. The remainder of the body of the device 2100 can remain anterior to the capsulorhexis. An IOL positioned within the recess defined by the side walls 2112 and the awnings 2110 can be supported on the Z-plane by the anterior segment of the capsular bag even while the lateral projections 2118 of the stabilization feature 2138 extend posterior to the capsulorhexis. The size and shape of the body prevents the device 2100 from falling through the capsulorhexis into the bag. Additionally, the distance between the side walls 2112 accommodates the span of the haptics 114. The haptics 114 can also be placed under slight compression by the inner bearing surfaces of the side walls 2112 to assist in retaining the IOL in position as described elsewhere herein.

FIGS. 10A-10D show implementations of the device 2100 that is configured to be fixated within the eye posterior to the capsulorhexis while at least a portion of the device remains anterior to the capsulorhexis. The device 2100 like other implementations described elsewhere herein can engage the capsulorhexis for fixation and stabilization, but the majority of the device (and thus, the IOL positioned within the recess of the device) is located within the capsular bag posterior to the capsulorhexis 40. This method of implantation eliminates the risk of iris interaction.

The device 2100 can be designed so that engagement with the capsulorhexis avoids significantly deforming the shape and orientation of the device 2100. The device 2100 can incorporate one or more reinforcements to prevent distortion. The reinforcement allows the device to engage with the eye, for example the capsulorhexis, in a way that provides secure fixation while avoiding distortion. The devices described herein can be reinforced to match or exceed the compressive force applied by the capsular bag. The compressive forces applied by the capsular bag is dependent upon the diameter of the capsulorhexis and thus, the diameter of the portions of the device that engage the capsulorhexis. The compressive forces applied by the capsular bag is also dependent upon the diameter, shape, and mechanical properties of the capsulorhexis. The diameter, shape, and mechanical properties of the capsulorhexis can be estimated, but not precisely predicted. Therefore, a device capable of adapting to a range of scenarios is preferred. The anterior and/or posterior surfaces of the device 2100 can be thickened and/or reinforced with materials to prevent distortion due to forces of the bag against the device 2100. The side walls 2112 and/or the corners of the device 2100 can be thickened and/or reinforced to limit flexure. A reinforcing ring can be incorporating near where the device interfaces with the capsulorhexis. The reinforcing ring can be an integrated or embedded material such as nitinol or a plastic that is more rigid than materials used to form other regions of the device such as the awnings 2110, side walls 2112, or posterior platform 2105. The materials, while providing some reinforcement, are also flexible enough to insert through a small incision as described elsewhere herein.

Figure 20A:
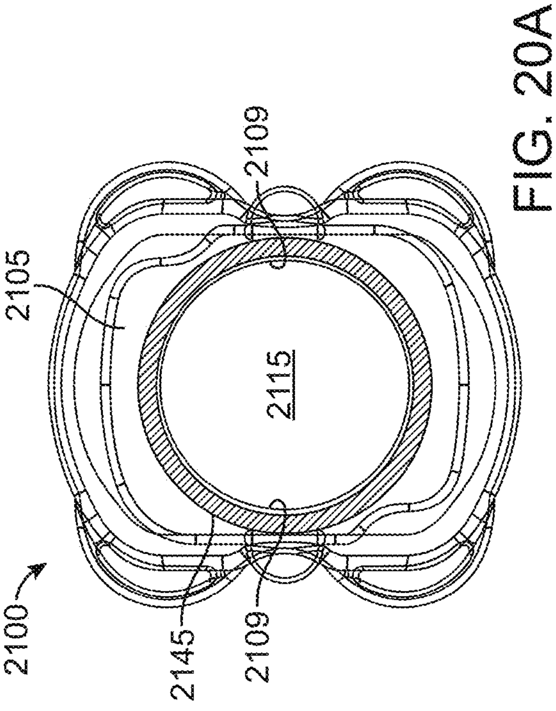
FIGS. 20A-20D show top plan views of interrelated devices incorporating reinforcement.
Figure 20B:
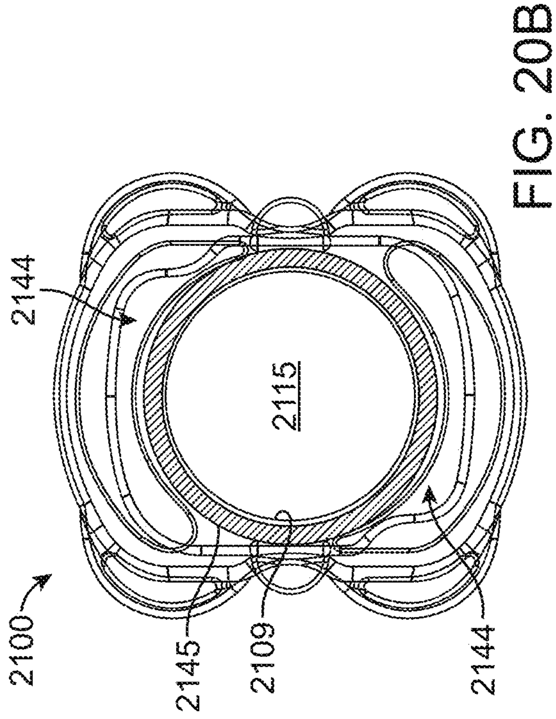
Figure 20C:
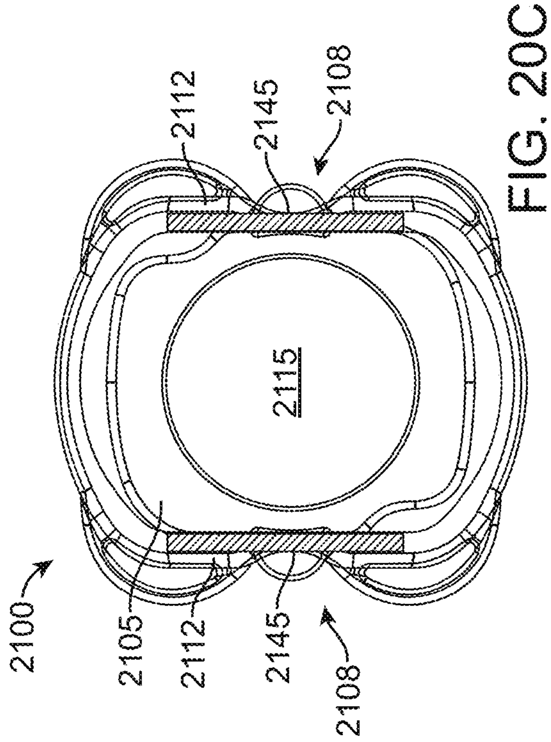
Figure 20D:
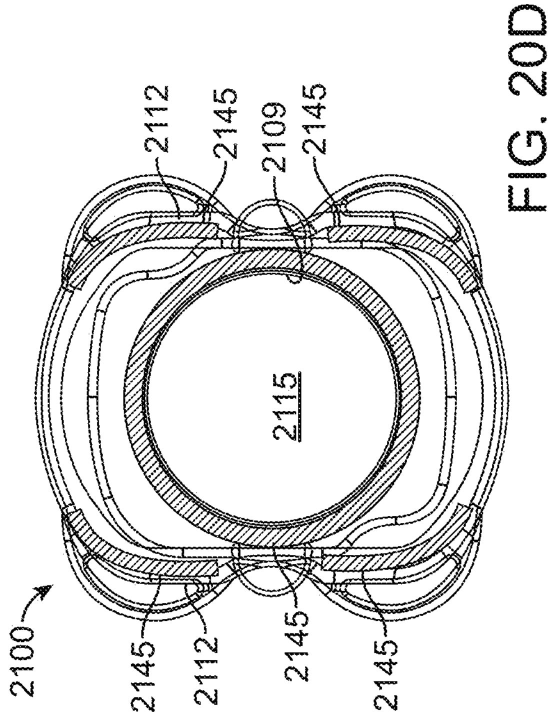

FIGS. 20A-20D show devices incorporating various types of reinforcement 145. FIG. 20A illustrates the reinforcement incorporated in the posterior platform 2105 of the device that is in the shape of a ring 2145. The ring of reinforcement 2145 can encircle the aperture 2115 and can be formed either by increasing the material thickness of the platform 2105 in this region or embedding secondary materials such as a plastic or metal providing greater hoop strength. FIG. 20B illustrates a ring 2145 of reinforcement in a posterior platform 2105 having a discontinuous surface due to the presence of one or more cut-outs 2144. As discussed elsewhere herein, the cut-outs 2144 minimize the bulk and thickness of the device thereby enabling easier insertion of the device into the eye. However, the cut-outs 2144 can diminish the hoop strength of the device making it more prone to distortion due to forces of the capsular bag. A ring of reinforcement 2145 within the discontinuous posterior platform 2105 (e.g., embedding a polymer or material having a greater rigidity than the material of the platform 2105) or by changing a material property of the discontinuous posterior platform 2105 (e.g., anterior-to-posterior thickness of the platform) can provide additional hoop strength of the device against the capsular bag while the cut-outs 2144 ensure sufficient flexibility for insertion of the device into the eye. FIG. 20C illustrates another configuration of the reinforcement in the form of one or more elongate beams 2145 along the side walls 2112 reinforcing the elongate sides 2108. FIG. 20D illustrates another implementation in which a ring 2145 of reinforcement encircles the aperture 2115 in combination with beams 2145 of reinforcement along the corners near the bumpers 2114. Any of a variety of reinforcement shapes and arrangements are considered herein to reinforce the device while still allowing for insertion of the device through a small incision.

The device 2100 can incorporate a stabilization feature 2138 as described elsewhere herein. The stabilization feature 2138 can project anteriorly from an anterior-facing surface of the device 2100 and can project laterally outward defining a space 2142 within which the anterior segment 35 of the capsular bag around the capsulorhexis 40 may be positioned. The stabilization feature 2138 is configured to be positioned anterior to the anterior capsule 35 while the remainder of the device 2100 lies posterior to the capsulorhexis 40. The stabilization feature 2138 can align the central axis CA of the device 2100 relative to the capsular bag 35 to ensure proper positioning of the optic 112 of the IOL 110 engaged with the device 2100 relative to the visual axis of the eye.

Figure 10A:
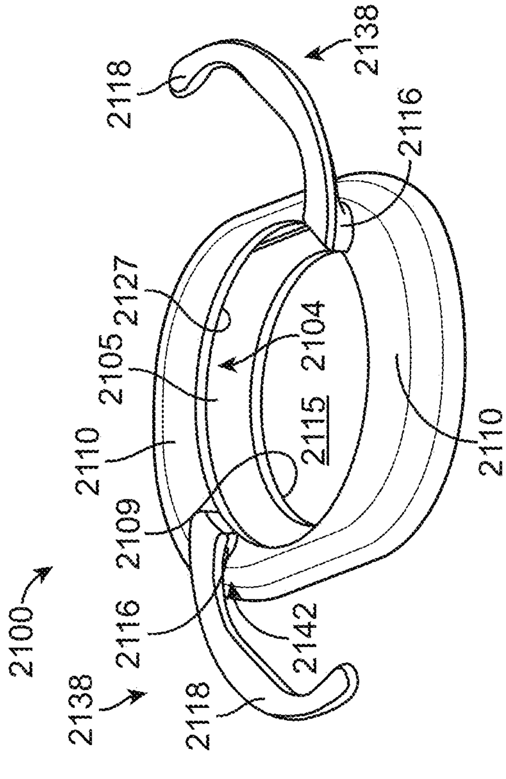
FIG. 10A is an interrelated implementation of a device having anterior stabilization features.
Figure 10B:
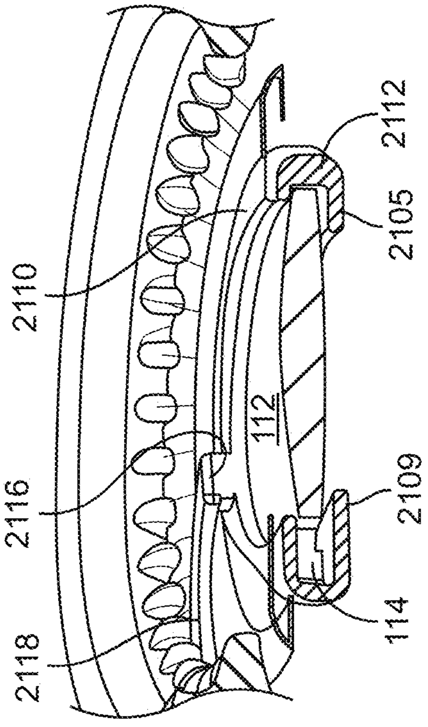
FIG. 10B shows a cross-sectional view of the device of FIG. 10A implanted in an eye.

The configuration of the stabilization feature 2138 can vary, but the stabilization feature 2138 for this implementation must not easily pass through the capsulorhexis once the device 2100 is positioned in the eye. The stabilization feature 2138 can include open loops, closed loops, wings, plates, continuous oval feature, flexible finger-like projections, or other configuration. The stabilization feature 2138 can form a haptic that extends into the ciliary sulcus similar to haptics of a 3-piece IOL. FIGS. 10A-10B illustrate an implementation of the stabilization feature 2138 that includes two open loops configured to extend laterally outward and anterior to the capsulorhexis 40 so as to engage with the ciliary sulcus while the anterior-facing surface of the device (i.e., the awnings 2110) abut against the posterior-facing internal surface of the capsular bag 35. In some implementations, the stabilization feature 2138 can be in the form of a haptic that is less than about 0.5 mm thick that extend into the ciliary sulcus or at least a distance along the top of the anterior capsule.

Figure 10C:
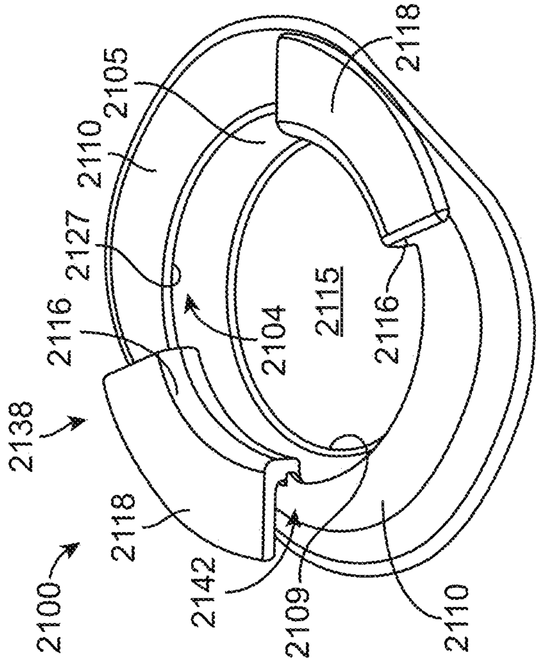
FIG. 10C is an interrelated implementation of a device having anterior stabilization features.
Figure 10D:
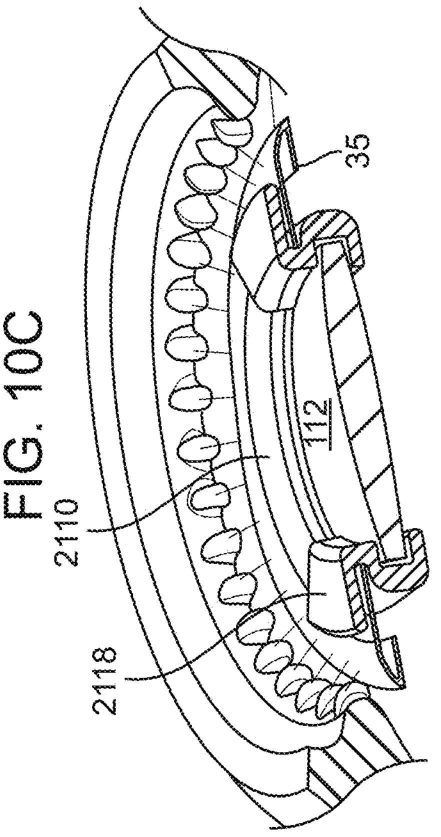
FIG. 10D shows a cross-sectional view of the device of FIG. 10C implanted in an eye.
Figure 11A:
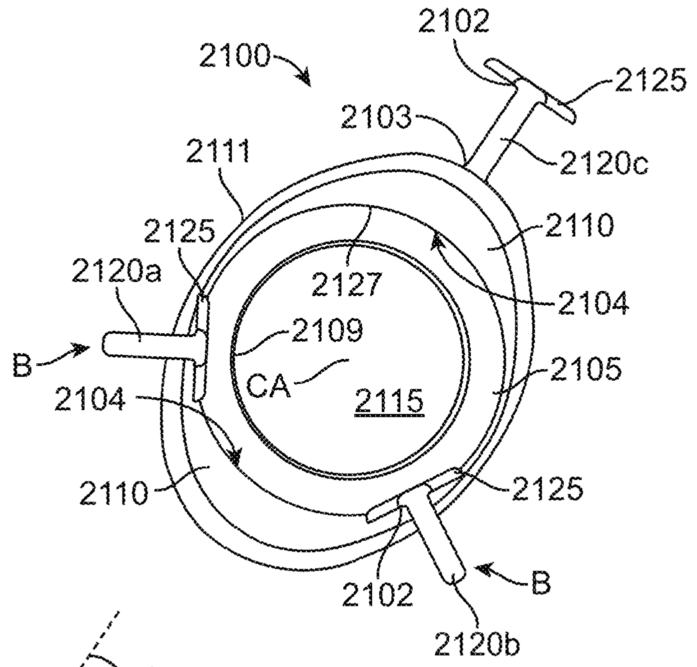
FIGS. 11A-11F show an interrelated implementation of a device having awnings configured to accommodate an IOL.
Figure 11B:
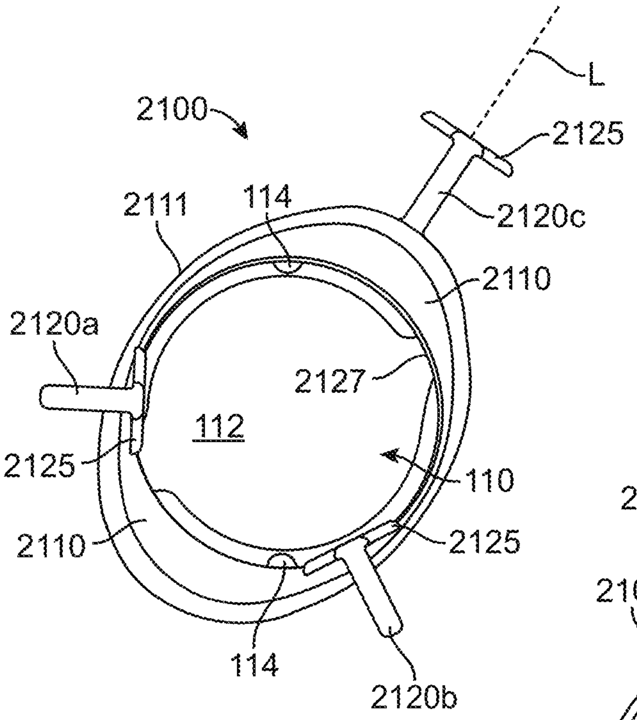
Figure 11C:
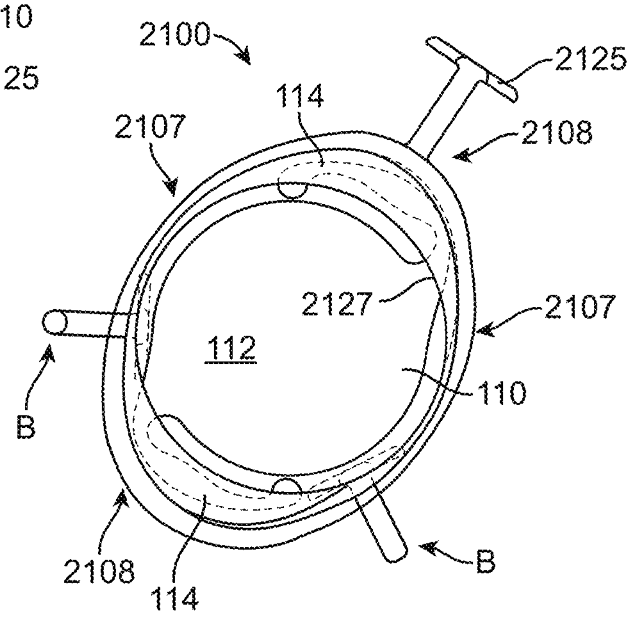
Figure 11D:
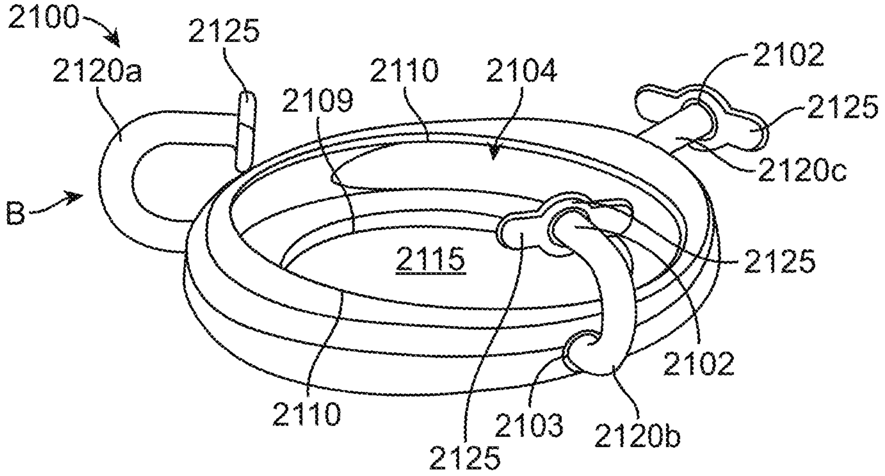
Figure 11E:
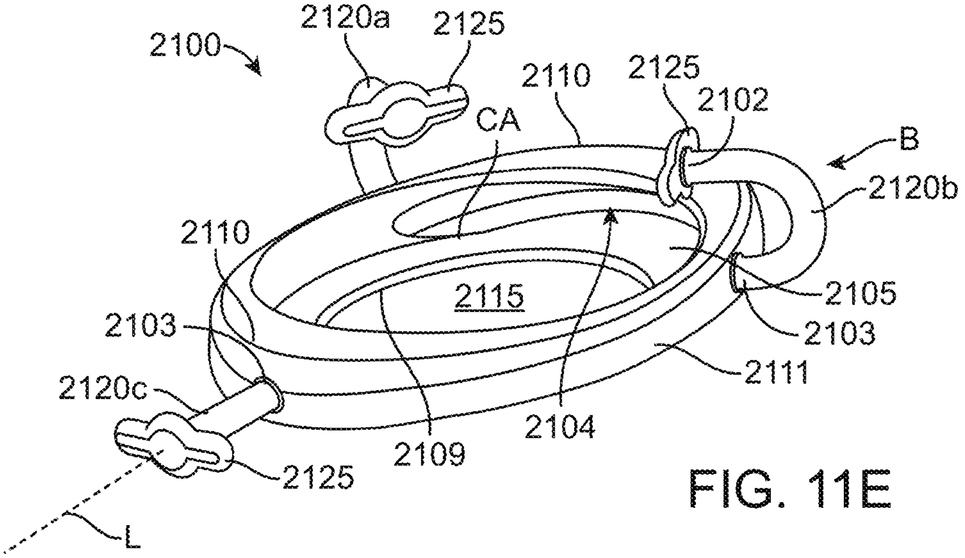
Figure 11F:
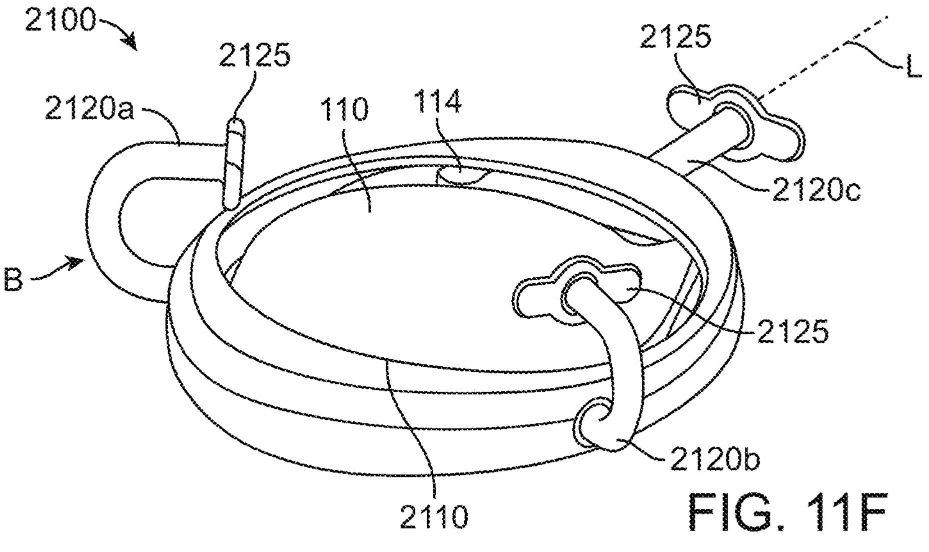

The stabilization feature 2138 can also rest atop the anterior capsule providing support for the device posterior to the anterior capsule. FIGS. 10C-10D illustrate an implementation of the stabilization feature 2138 that includes two lateral projections configured to extend laterally outward and anterior to the capsulorhexis 40 so as to engage with an anterior surface of the capsular bag 35 while the anterior-facing surface of the device (i.e., the awnings 2110) abuts against the posterior-facing internal surface of the capsular bag 35.

Each implementation of the stabilization feature 2138 shown in FIGS. 10A and 10C can have a first portion 2116 and a second portion 2118 coupled to and extending laterally outward from the first portion 2116. The first portion 2116 can be positioned near an edge of the awnings 2110 defining aperture 2127. The first portion 2116 can project a distance anteriorly from the anterior-facing surface of the awnings 2110 thereby defining the size of the space 2142 between the awnings 2110 and the second portion 2118. The distance the first portion 2116 projects is sufficient to allow the anterior capsule 35 of the capsular bag to insert between the awnings 2110 and the second portion 2118 so that the capsulorhexis 40 engages against the first portion 2116. The first portion 2116 can be a ring-shaped structure defining an outer diameter sized to pass through and engage with the anterior capsulorhexis 40. However, the first portion 2116 need not be fully ring-shaped. For example, the first portion 2116 can be formed by a plurality of projections that are arranged on opposite sides of or around the aperture 2127. The engagement can occur at just 2 points similar to traditional optical capture with a cat eye capsulorhexis. The engagement can spread across an arc, for example, about 2 mm up to about 6 mm per side. The stabilization feature 2138 can be sized to be compatible with various sized capsulorhexis between about 4 mm to about 7 mm, or about 5 mm to about 6 mm. The engagement between the stabilization feature 2138 and the capsulorhexis 40 can limit translation, axial, and rotational movement of the device 2100 in the eye and thus, the IOL engaged with the device 2100. The second portion 2118 does not pass easily through the capsulorhexis once the device is implanted.

Once the device 2100 is fixated and stabilized relative to the capsulorhexis, the IOL 110 can be passed through the capsulorhexis and the anterior opening 2127 to be arranged within the recess 2104 posterior to the awnings 2110. To reduce the risk of the IOL 110 passing posterior to the device 2100 during surgery, the depth of the recess 2104 between the awnings 2110 and the posterior platform 2105 can be greater than the depth of the recess described for implementations of the device positioned anterior to the capsulorhexis. Additionally, the central aperture 2115 can have a smaller diameter than other implementations of the device positioned anterior to the capsulorhexis. For example, the central aperture 2115 can have a diameter that is about 4.5 mm up to about 5.0 mm to reduce the risk of the IOL 110 from passing posteriorly to the central aperture 2115. At least a portion of the posterior platform 2105 can be reinforced or thickened to increase the hoop strength of this posterior surface and to reduce the likelihood than an IOL 110 would inadvertently pass through the central aperture 2115. The device 2100 is preferably designed to allow easy insertion of the IOL 110 through the anterior aperture 2127 and the capsulorhexis and prevent easy passing of the IOL 110 through the central aperture 2115 posterior to the device 2100.

It should be appreciated that any of the features described with respect to the devices shown in FIGS. 10A-10D that include a device body configured to be positioned posterior to a capsulorhexis can be incorporated in any of a variety of combinations in any of the other implementations of the devices described herein including device embodiments having a device body configured to be positioned anterior to a capsulorhexis and vice versa.

The one or more fixation arms 2120 can be trans-scleral fixation arms that are designed to be atraumatically externalized and held in place by its geometry and mechanical properties alone, i.e. not requiring sutures or glue. The externalized portion or anchor 2125 (also referred to herein as an anchoring footplate or footplate) at a peripheral end (also referred to herein as a terminal end or a terminal portion) of the fixation arm 2120 can sit sub-conjunctivally to anchor the arm 2120 in position. In some implementations, the conjunctiva may be taken down and re-formed following externalization. The instruments for implantation can allow for trans-conjunctival placement as well as sub-conjunctival placement. The anchor 2125 of the fixation arm 2120 can have a sturdy, but low profile geometry so as to remain stable and not re-enter the eye and minimally erode the conjunctiva. Additionally, the fixation arms 2120 of the device 2100 may be manufactured in a way so as to facilitate easy visualization and manipulation of the device prior to surgery. At least one of the fixation arms 2120 may be manufactured to have a geometry that is substantially non-planar at rest and then be manipulated into a planar configuration during the implantation procedure and, for example, when placed under tension.

The device 2100 can include one, two, three, or more fixation arms 2120. In a preferred implementation, the device 2100 includes three fixation arms 2120 that are arranged symmetrically or equidistant around the perimeter of the support structure 2105. The fixation arms 2120 can center the lens support structure 2105 and provide sufficient support for long-term stability. In some implementations, that may be accomplished by a single fixation arm 2120. In other implementations, the one or more fixation arms includes three fixation arms 2120 symmetrically arranged around a perimeter of the lens support structure. The fixation arm 2120 can be constructed from a semi-rigid material or may have a geometry that provides sufficient structural rigidity.

The device 2100 can also include just two fixation arms 2120. These fixation arms 2120 may be under equal and opposite tension when implanted and anchored trans-sclerally. Alternatively, the fixation arms 2120 may be asymmetric such that one fixation arm 2120 is under tension and the other fixation arm 2120 has a rigidity and length that it functions as a rigid spacing element. A fixation element that is rigid or capable of applying a spring force can rely on penetration of the adjacent tissue or being wedged into place. A tensioned fixation element can rely on a slight stretch or expansion of the material once placed. One or both of the fixation arms 2120 may be produced with an inward biased configuration in which the fixation arm is biased towards an anterior projecting curve or a folded configuration as described elsewhere herein. The fixation arms 2120 may have a paddle like geometry that resists rotation when engaged with ocular tissue.

The device 2100 can also include three or more fixation arms 2120. Three fixation arms 2120 can provide the device 2100 with a defined fixation plane that is substantially parallel to the Z-plane (vertical plane) of the eye. The fixation arms 2120 can be designed and deployed in a manner that puts each fixation arm 2120 in equal and opposite tension. Alternatively, one or more fixation arms 2120 may be designed to have a rigidity and length allowing to behave as a rigid spacing element. Zero, one, two, or all three or more of the fixation arms 2120 can be manufactured with an inward biased design or biased towards a center of the device or the central axis CA of the device (see FIGS. 11A-11F, 12A-12C, and 13A-13E). The inwardly biased fixation arms 2120 can extend from the support structure and have a folded configuration prior to implantation. At least one, but fewer than all, of the fixation arms may be biased or curved as described herein. At least two, but fewer than all may be biased or curved as described herein. In some implementations, all of the fixation arms 2120 may be biased or curve. The device can include three fixation arms, wherein two of the three fixation arms are flexible and biased towards a folded configuration, and a third fixation arm is less flexible than the other two and is biased towards an unfolded configuration. The folded configuration of each of the fixation arms can bias the terminal end portion of the fixation arms towards a central axis CA of the device. The lens support structure can be biased towards a substantially flat or planar configuration while the fixation arm(s) is biased towards the folded configuration that is not substantially flat or planar.

Once implanted and fixed trans-sclerally, the inwardly biased arms can be unbent or unfolded (unfurled) away from their folded, inwardly biased configuration. In a preferred implementation, two fixation arms 2120 have an inward bias geometry and the third fixation arm 2120 has increased cross-sectional area—increasing its rigidity. The inwardly biased fixation arms 2120 can incorporate a bend between an origin of the arm with the lens support structure 2105 and their terminal end. The two bent fixation arms 2120 can be biased towards the central axis CA of the device towards a folded configuration.

In an implementation, the device 2100 can include at least three fixation arms 2120. At rest and prior to implantation, one of the at least three fixation arms can extend in an unfolded configuration from the support structure and at least two of the at least three fixation arms extend in a folded configuration from the support structure. And, at rest prior to implantation, one of the at least three fixation arms can be biased towards the unfolded configuration and at least two of the at least three fixation arms can be biased toward the folded configuration. After implantation, each of the arms biased toward the folded configuration can be unfolded.

Each of the fixation arms 2120 can include an origin portion 2103 at the support structure 2105 and a terminal end portion 2102 coupled to an atraumatic anchor 2125 for sutureless, trans-scleral fixation. Prior to trans-scleral fixation of the anchors 2125, one of the plurality of fixation arms 2120 (up to all of the fixation arms 2120) can include a curved fixation arm 2120 that is curved between its origin portion 2103 and its terminal end 2102 forming a bend B (see FIGS. 11A-11F, 12A-12C, and 13A-13E) enabling direct visualization of at least a portion of the curved fixation arm 2120 through the pupil 30 of the eye (see FIG. 14). After trans-scleral fixation of the anchors 2125, each of the plurality of fixation arms 2120 can be tensioned between the origin portion and the terminal end to align the support structure relative to the Z-plane of the eye. The support structure 2105 is adapted to provide support for an intraocular lens. The central aperture 2115 extending through the full thickness of the support structure 2105 is adapted to permit passage of light through both the central aperture 2115 and the IOL supported by the support structure 2105. The curved fixation arm 2120 can curve anteriorly such that a portion of the arm 2120 such as the terminal end 2102 and/or its atraumatic anchor 2125 is positioned over at least a portion of the support structure 2105 (e.g., the upper surface of the support structure 2105 and/or over a region of the central aperture 2115). Alternatively, the curved fixation arm(s) 2120 can curve posteriorly such that a portion of the arm 2120 such as the terminal end 2102 and/or its atraumatic anchor 2125 is positioned under at least a portion of the support structure 2105 (e.g., the lower surface of the support structure 2105 and/or under a region of the central aperture 2115).

FIGS. 11A-11F, 12A-12C, 13A-13E illustrate implementations of a device 2100 having fixation arms 2120 at rest and prior to implantation. Two of the three fixation arms 2120 curve inward such that they are biased towards a folded configuration at rest. The arms 2120 extend outward substantially orthogonally from the support structure 2105, such as from their origin 2103 at the support structure 2105 and make a turn (anteriorly or posteriorly) forming a curve between the origin 2103 and the terminal ends 2102 of the arms 2120. The curve of the arm 2120 can result in the terminal end 2102 of the arm 2120 being positioned nearer to its own origin portion 2103. In some implementations, the arm 2120 curves in an anterior direction such that the terminal end 2102 of the arm 2120 is positioned anterior to the arm's origin portion 2103 or over at least a portion of the anterior-facing surface of the support structure 2105 near the arm's origin portion 2103. In other implementations, the arms 2120 can curve in a posterior direction such that the terminal end 2102 of the arm 2120 is positioned posterior to the arm's origin portion 2103 or under at least a portion of the posterior-facing surface of the support structure 2105 near the arm's origin portion 2103. In an implementation, the anchors 2125 of the curved fixation arms 2120 can curve away from a first plane of the support structure (e.g., Z-plane of the eye) into a second plane that is parallel to the first plane. The second plane can be anterior or posterior to the first plane depending on whether the arms 2120 curve anteriorly or posteriorly. The curve can be in a direction that is substantially transverse (e.g., X-plane) to the plane of the lens support structure 2105 (e.g., Z-plane). The dilated pupil (depending on whether adult or pediatric patient) can have a diameter up to about 8 mm. The curve positions the anchors 2125 of the curved fixation arms 2120 to be positioned within a diameter of a circle in that second plane that is visible within the diameter of a dilated pupil so as to not impede direct visualization by the opaque iris, for example, between about 3 mm up to about 7.5 mm, more preferably about 7 mm. The anchor 2125 of each of the curved fixation arms 2120 can be positioned a distance from the center of the device, for example, about 1.5 mm, 2.0 mm, 2.5 mm, 3.0 mm, up to an no greater than about 3.5 mm, or no greater than about 4.0 mm from the center of the device. The curved arms 2120 provide for positioning the terminal end portions 2102 and/or the anchors 2125 within this diameter or this distance from the center of the device allowing for ease of visualization. The third of the three fixation arms 2120 is biased into a straight or unfolded configuration at rest. The third arm 2120 extends outward orthogonally from its origin 2103 at the support structure 2105 and makes no turn or bend. Rather, the entire third arm 2120 is entirely straight and extends substantially along a single axis. The two fixation arms that, at rest, were biased towards a folded configuration are now in an unfolded configuration, for example, by tensioning the arms 2120 via the trans-scleral anchors being externalized.

It should be appreciated that the device 2100 can be viewed directly through the pupil even if there are no fixation arms 2120 or the fixation arms 2120 are not biased into a folded configuration at rest. For example, the device 2100 can incorporate one or more centrally projecting features 2117 such as on the awnings 2110 (see FIGS. 18E-18H or FIGS. 18I-18J) that can be visualized by a user during implantation. The features 2117 project sufficiently towards a center of the central aperture 2115, for example, at least about 2.5 mm to about 3 mm from center so that they are visible through the pupil during an implantation procedure.

The fixation arms 2120 may be uniformly distributed around the device 2100 to provide uniform tension. Alternatively, the fixation arms 2120 may be oriented in a non-uniform distribution, for example, with three fixation arms 2120 that are 90 degrees from one another. In this circumstance two of the fixation arms 2120 would be 180 degrees from each other, providing opposing tension; while the third fixation arm 2120 serves primarily to prevent the device 2100 from rotating.

Each fixation arm 2120 can have a spring force that is a function of elongation of the material when under a load. In contrast, an open loop haptic or coil spring may have a spring force provided due to bending of a material that has a substantially fixed length. The fixation arms 2120 once anchored in the eye can be under tensile stress and material elongation. For example, each fixation arm 2120 can provide for extension over a radius of between about 7.5 mm to 8.0 mm to accommodate diameters between about 15 mm to about 16 mm. The device has an operable range of tension for function. As an example, the device can be under a first amount of tension once implanted (X tension). The first amount of tension is the amount of tension in the minimum acceptable diameter. In other words, the device is under a minimum amount of tension in order to function, but is capable of being placed under greater tension to accommodate larger diameters. In the example of fixation arms 2120 capable of accommodating both 15 mm and 16 mm extension, each force transfer arm can operate while under the first tension X and while under at least a second tension. The second tension can be the sum of the first tension X plus a distance of tension (e.g., 0.5 mm of tension). The fixation arms can withstand the differential tension available in each extension ratio. To further illustrate the example, if each fixation arm 2120 in this implementation is about 4 mm long, then the second tension (X tension+0.5 mm of tension) can undergo a 12.5% increase in elongation to function at the 15 mm diameter and also function up to the 16 mm diameter. If the fixation arms 2120 in this example are 2 mm long, then the second tension (X tension+0.5 mm of tension) can undergo a 25% increase in elongation to function at the 15 mm diameter and also function up to the 16 mm diameter. If the fixation arms in this implementation that are about 6 mm long, then the second tension (X tension+0.5 mm of tension) can undergo a 6.25% increase in elongation to function at the 15 mm diameter and also function up to the 16 mm diameter. The decreased spring force of the fixation arms 2120 can enhance the safety and function of the device because the tension of the anchor on the ocular tissue is less dependent on variables that are difficult for the surgeon to assess—the eye's inherent dimensions and the specific location of the incisions. Additionally, the length of the fixation arm (e.g., between about 2 mm to 6 mm) as well as the inward curve (anteriorly or posteriorly) of at least one or more fixation arm 2120 improves access and visualization for the surgeon to find and fix the arm during the operation. The device can have a relaxed fixation diameter Dd that is between about 15 mm up to about 20 mm, preferably between about 16.50 mm up to about 18.00 mm, where the radius of the circle is measured from the center of the central aperture 2115 to an inner facing surface of the anchor 2125 of the straight fixation arm 2120 (see FIG. 18E).

The terminal footplates or anchors 2125 of the fixation arms 2120 can be coupled to or positioned at an outer terminus of the fixation arms 2120. The anchor 2125 can have various geometries designed to be easily externalized by the surgeon and to stabilize tension on the device throughout its useful life. The anchors 2125 can have a generally low profile and can have a geometry (e.g., rounded) designed to limit conjunctival erosion and eyelid irritation. The terminal end of the fixation arm 2120 can have an anchor 2125 configured to be positioned external to the sclera 20 to secure the lens support structure 2105 and prevent centripetal slippage. The geometry of the anchor 2125 allows for the surgeon to pass the anchor 2125 through a puncture or incision in the sclera 20 using forceps, trocars, snares, or other surgical tool, including a snare device for anchor extraction as described in U.S. Pat. No. 10,973,624, which is incorporated herein by reference. The anchor 2125 can have a geometry that resembles a nail head, a T-bar, a multi-pronged shaped, or any other geometry that can preferentially be passed through the sclera 20 in a first direction and resist pulling out the direction of insertion to maintain its external position when the arm 2120 is placed under the tension anticipated through the lifetime of the device. The anchor 2125 is designed to have a profile and geometry that does not cause irritation to the eyelid or conjunctiva throughout the useful life of the device 2100. As such, preferred geometries will have minimal thickness profiles with smooth, rounded and/or tapering edges. The anchor 2125 can have a substantially constant thickness or can have a thickness that various over its length, as discussed in more detail below.

Figure 16A:
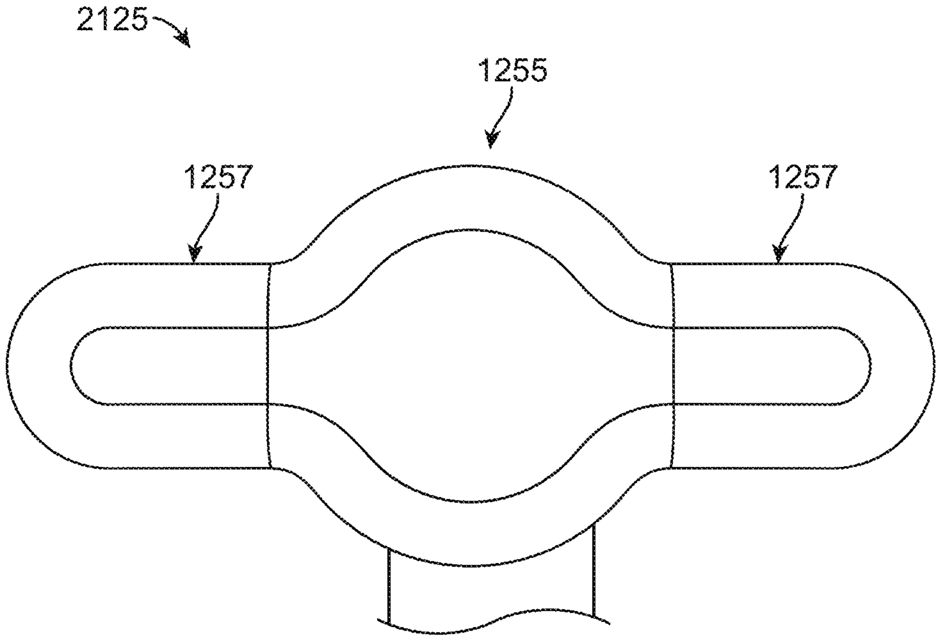
FIG. 16A is an end-view of an anchoring footplate coupled to a terminal end of a fixation arm.
Figure 16B:
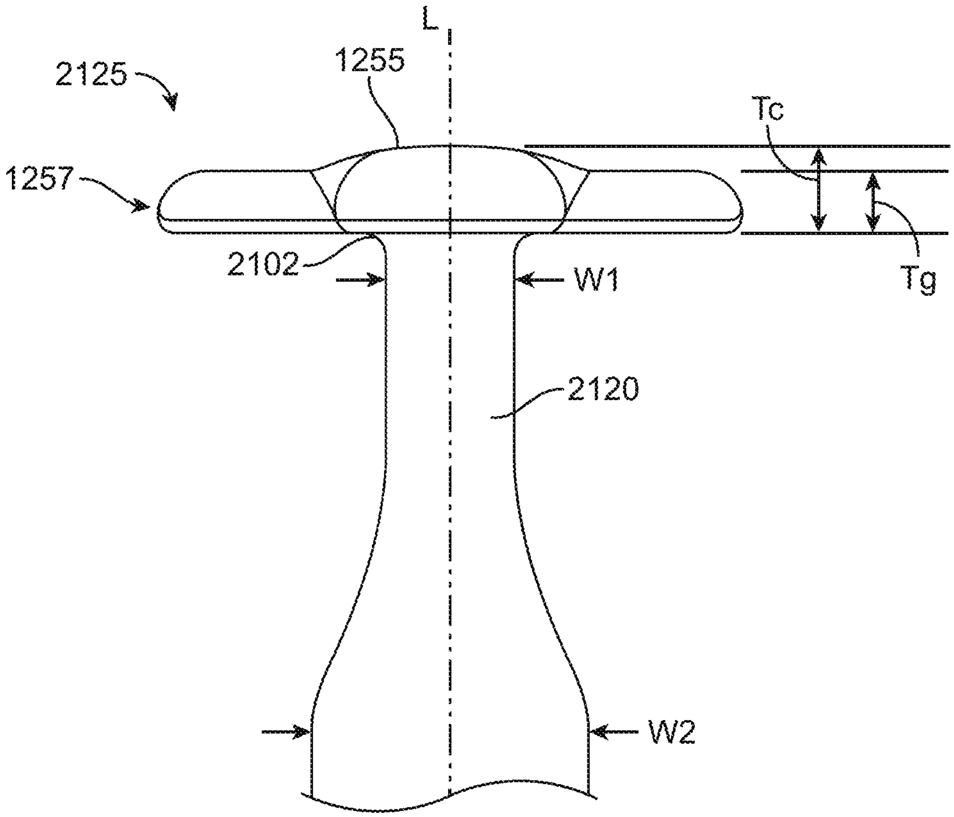
FIG. 16B is a side-view of the fixation arm of FIG. 16A.
Figure 16C:
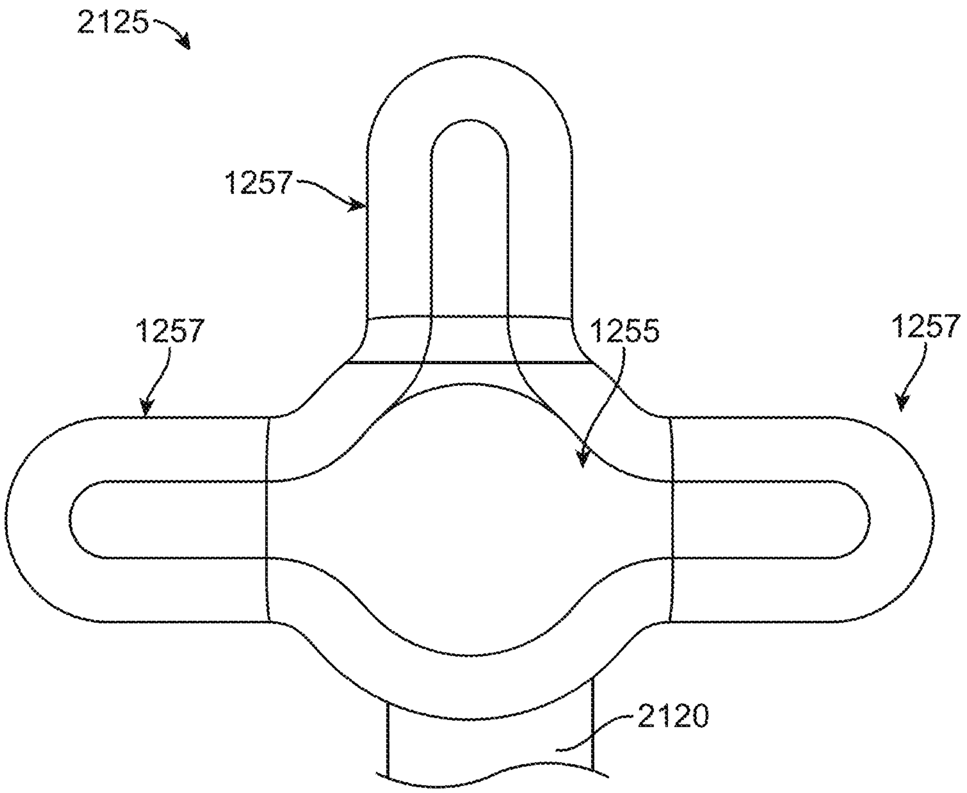
FIG. 16C is an end-view of an anchoring footplate coupled to a terminal end of a fixation arm.

The anchors 2125 described herein are configured to be both easily externalized and resistant to re-internalization following externalization. The anchors can be designed such that they are graspable using an ophthalmic tool (e.g., 23, 25, or 27 gauge). A geometry that is ideal for grasping with an ophthalmic tool may not necessarily be ideal for firm fixation. FIGS. 16A-16C illustrate additional geometries of the anchors 2125 that have variations in thickness, width, and/or height. The anchors 2125 can include a central portion 1255 and one or more graspable portions 1257 at a periphery of the central portion. The central portion 1255 can be arranged to lie over the wound (sclerotomy) through which the anchor 2125 was inserted and the graspable portions 1257 arranged immediately adjacent the wound. The central portion 1255 can have increased thickness, height, and/or width compared to the graspable portions 1257 at the periphery. The increased thickness, height, and/or width of the central portion 1255 can add bulk to the area over the wound and thereby reduce the likelihood that tension on the fixation arm pulls the anchor 2125 back through the wound. The central portion 1255 of the anchor 2125 may have a thickness Tc along a longitudinal axis L of the arm 2120 that is greater than a thickness Tg of the graspable portion 1257. For example, the thickness Tc can be between about 1.2 to 5.0 times as thick as a thickness Tg of the graspable portion 1257. In other implementations, the central portion 1255 may have a width or height that is between about 1.2 to 5.0 times as wide or as high as the graspable portions 1257. The geometry of the bulkier area is designed to resist deformation when under the tensile forces associated with normal use of the device. The bulkier central portion 1255 can collapse inward to fold over onto the terminal end of the arm 2120 to which it is attached during externalization. Once the arms 2120 are placed under tension, the bulkier central portion 1255 is incapable of being folded over away from the terminal end of the arm 2120 onto itself, which prevents the externalized anchor 2125 from being pulled back through the wound. Thus, the central portion 1255 can be pulled through the wound in the first direction (outward from the eye) despite its greater bulk, but is prevented from being pulled through the wound in the second opposite direction (inward towards the eye) because of its greater bulk.

The graspable portions 1257 can include any of a variety of shapes, including ovoid, rectangular, star-like pattern, or other shape or geometry that improves grasping of the graspable portions 1257 compared to, for example, the central portion 1255. The graspable portion 1257 may have a thinned and narrow tab that extends from the central portion 1255. Each anchor 2125 may include 1, 2, 3, 4, 5, 6, or more graspable portions 1257 to allow the user to grasp the anchor regardless of the conformation of the device.

In some implementations, each fixation arm 2120 can have more than a single anchor 2125. The device 2100 can have three fixation arms 2120, each having a first anchor 2125 on a terminal end and a second anchor 2125 positioned internal to the first anchor 2125. The second anchor 2125 can further secure the lens support structure 2105 by preventing centrifugal slippage. Alternatively, the second anchor 2125 can be externalized through the sclera 20 such that the second anchor 2125 also holds the device 2100 in place. Each fixation arm 2120 can include a plurality of anchors 2125 that can be positioned along a length of the fixation arm 2120. The plurality of anchors 2125 can include 2, 3, 4, 5, or more anchors 2125 evenly spaced along its length. The surgeon may externalize as many anchors 2125 as necessary to center the device 2100. The excess material of the fixation arm 2120 and anchors 2125 peripheral to the external anchor 2125 nearest the sclera 20 can be removed such as by trimming. Trimming material off the device, such as one or more of the fixation arms 2120, an anchor 2125 of the arm, etc., allows for on-the-fly customization to a patient's eye. In some circumstances, such as when the fixation arm 2120 has a plurality of anchors 2125 that are externalized through the sclera, the extra anchors 2125 (and also a section of the arm 2120) peripheral to the anchor 2125 performing the anchoring function can be removed from the arm 2120. The plurality of anchors 2125 per each fixation arm 2120 can therefore allow for the surgeon to size the device 2100 to the patient's eye intraoperatively. Trimming of the anchors 2125 and/or outer portion of the fixation arm(s) 2120 externalized through the sclera allows for the length of the fixation arm 2120 to be customized or adjusted on the fly. A surgeon may also determine that only one of a plurality of fixation arms 2120 are needed for a particular implantation procedure. The surgeon may trim off the unneeded arms 2120 prior to implanting the device in the eye. For example, the surgeon may decide to trim off the bent arms prior to implantation leaving only a straight arm for tethering relative to the sclera. In an implementation, the device 2100 has a plurality of fixation arms 2120. Once the device 2100 is implanted in the eye and at least some of the fixation arms 2120 selected to provide stabilization of the device within the eye, one or more of the remaining fixation arms 2120 that were not needed for stabilization can be trimmed off from the device 2100 and removed from the eye. The device 2100 is therefore customizable in length of the fixation arms 2120 as well as number of fixation arms in real-time during an implantation procedure.

The two anchors 2125 on the single fixation arm(s) 2120 can have different outer dimension with the inner anchor 2125 being narrower than the outer-most anchor 2125. It should be appreciated that the plurality of anchors 2125 on the single fixation arm 2120 can also have the same dimension and need not vary in their size. The anchors 2125 can also have a geometry that improves their passage through the sclera in a first direction, but impairs their passage through the sclera in a second, opposite direction. For example, the anchors 2125 can incorporate square edges. However, the anchors 2125 can have a square edge on an inner-facing surface and a smooth tapered edge on an outer-facing surface that aids in their passage through the sclera in an outward direction.

Fixation arms 2120 extending to the eye wall can be difficult to manipulate as they can be blocked from view by the peripheral iris 10, limbus and sclera 20. As discussed above, one or more of the fixation arms 2120 can be inwardly biased toward a folded configuration so that they may be directly visualized through the pupil (see FIG. 14). Each of the fixation arms 2120 may extend initially from the support structure 2105 outward in an orthogonal direction and then curve or fold anteriorly (or posteriorly) such that the terminal ends 2102 of the fixation arms 2120 (or at least a portion of the anchor 2125) are positioned over at least a portion of the fixation arm 2120, the support structure 2105, or the central aperture 2115 extending through the support structure 2105. At least a portion of the bent fixation arms (i.e., the terminal ends and/or the anchors 2125) can be more easily visualized through a dilated pupil and visualization is not impeded by the opaque iris 10 (see FIG. 14). This inward (centripetal) bias also allows the bent fixation arms 2120 to be safely grasped and manipulated during device implantation. Each of the fixation arms 2120 of the device 2100 can have inward bias toward a folded configuration or just a selection of the fixation arms 2120 can have inward bias (e.g., one, two, up to less than all fixation arms 2120).

The fixation arm 2120 can also be molded to incorporate a bend or curve between its origin with the lens support structure 2105 and the terminal anchor 2125 (see FIGS. 11A-11F, 12A-12C, 13A-13E, and FIG. 15). The bent fixation arm(s) 2120 can be biased towards a folded configuration. For example, one or more of the fixation arms 2120 can bend between 90 degrees and 270 degrees from its origin with the lens support structure 2105 in a radial and centripetal direction. The terminal end 2102 of the bent fixation arms 2120 thus, lie in a different plane from a plane of the lens support structure 2105. When in a resting state prior to being positioned in the eye, the terminal end 2120 of at least a first fixation arm 2120 of the plurality of fixation arms 2120 can incorporate a bend B between its origin 2103 with the lens support structure and its terminal end 2102 forming a bent arm. The bent arm can extend at least a first distance from its origin orthogonal to the lens support structure 2105.

The bent arm can then curve upward (anteriorly) away from the plane of the lens support structure 2105 at least another distance. The bent arm 2120 can then curve back towards its origin or towards the central axis CA of the device. This can result in the terminal end of the bent arm 2120 lying in a different plane than the plane of the lens support structure 2105. The curve or bend in the arm 2120 can be projecting outward away from the central axis CA and away from both the arm's origin 2103 and terminal end 2102. The trans-scleral anchor 2125 and/or a terminal portion of the fixation arm 2120 can be positioned over or anterior to at least a portion of the lens support structure 2105 or positioned over at least a portion of the central aperture 2115. Alternatively, the bent arm(s) 2120 can curve downward (posteriorly) away from the plane of the lens support structure 2105 at least a distance and the trans-scleral anchor 2125 or a terminal portion of the fixation arm 2120 can be positioned under or posterior to at least a portion of the lens support structure 2105 and/or under or posterior to at least a portion of the central aperture 2115. The folded configuration (whether the arms 2120 curve anteriorly or posteriorly) allows for at least a portion of the bent fixation arms 2120 such as the terminal ends of the bent fixation arms 2120 and/or their anchors 2125 to be visualized through the pupil and not impeded by the opaque iris. Only one arm 2120 of the fixation arms 2120, two arms 2120 of the fixation arms 2120, or all of the fixation arms 2120 can incorporate a curve. Alternatively, none of the fixation arms 2120 can incorporate a curve (see FIGS. 18I-18J).

Once the device is positioned and anchored in the eye, the fixation arms 2120 are placed under tension such that the bent arm is unfurled away from this folded configuration and is no longer bent. The terminal end of the arm 2120 is urged away from this resting state in which the arm 2120 is in a folded configuration to urge the bent fixation arm into a straight or unfolded configuration.

The bend B of the folded configuration can be a gradual, smooth bend having a radius of curvature or can bend so as to form one or more distinct angles along a length of the arm 2120. The bend can be tight enough to avoid projecting too far anterior while still capable of being unfurled or placed into an unfolded configuration with relative ease without imparting undue stress on the lens support structure 2105. The inward biased geometry can have a curve that is between about 0.10 mm to about 2.5 mm radius of curvature on the inner curve (anterior-facing side) and between about 0.6 mm to about 3.0 mm radius of curvature on the outer curve (posterior-facing side). In an implementation, the terminal end of the inwardly biased fixation arm can be spaced from the lens support structure 2105 forming a gap G (see FIGS. 13D-13E). The gap G can be between about 0.2 mm up to about 2.5 mm. In an implementation, the biased fixation arm 2120 curves a full radius of 180 degrees and has an inward biased geometry that is about 0.63 mm radius of curvature on the inner curve and about 1.13 mm on the outer curve such that the lens support structure 2105 and the biased fixation arm are spaced by about 1.25 mm. The start point of the curve (near the origin 2103 with the lens support structure 2105) and the end point of the curve (near the terminus 2102 at the trans-scleral anchor 2125) can have a plurality of radiuses such that the curve changes over the length of the fixation arm 2120. The curve of the biased fixation arms 2120 can have an average curvature between about 0.15 mm to about 2 mm on the inner curve.

Figure 14:
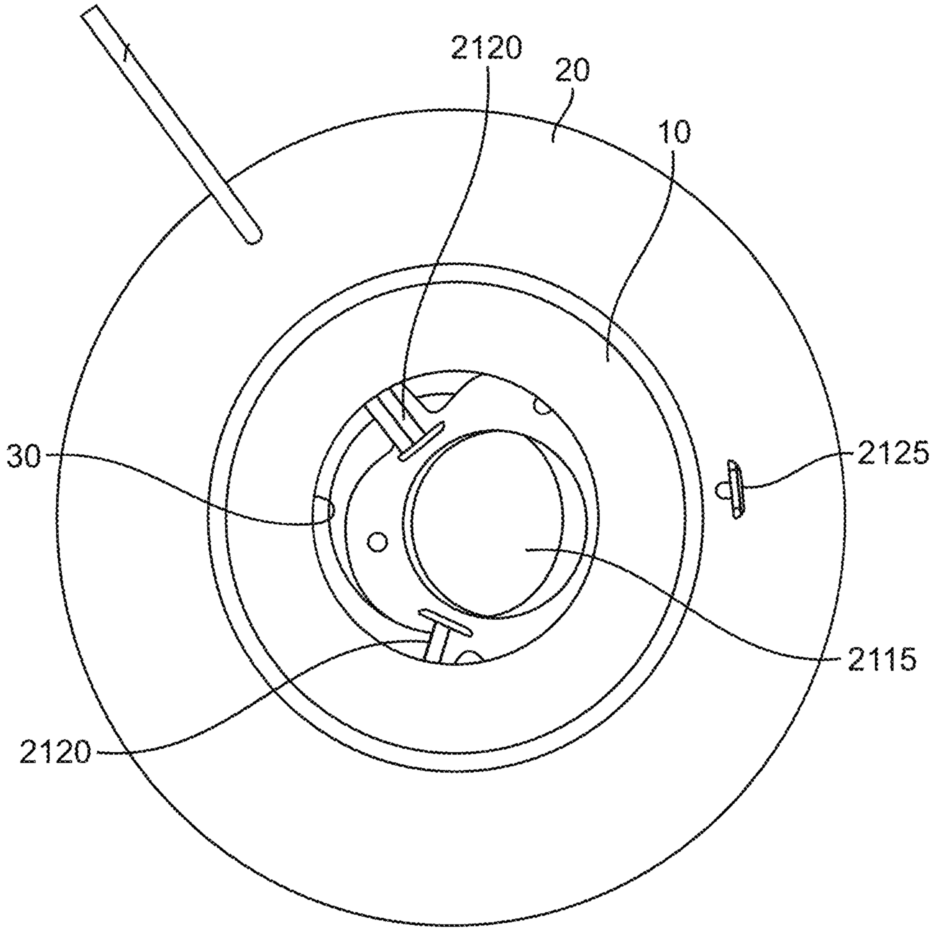
FIG. 14 shows a top down view of an eye implanted with a device having biased arms visible through the pupil.

The bent fixation arms 2120, after implantation and prior to fixation with the scleral wall, can be visible through the pupil when in an unstressed (resting) state (see FIG. 14). This visibility allows the surgeon to easily engage the anchor 2125. When the surgeon engages the fixation arms 2120 by grabbing the body of the fixation arm 2120 or anchor 2125, the surgeon can unfurl the fixation arm 2120 away from the resting, folded configuration in a way to bring it substantially on plane with the lens support structure 2105. These fixation arms 2120 can have a flexibility such that the stresses stored in the material in the deployed state will not impart torsional or tensile forces upon the lens support structure 2105 in a way that compromises device function. The fixation arm(s) 2120 can be molded to have a 90-270 degree turn from its lens support origin in a tangential and centripetal direction. The fixation arm(s) 2120 can incorporate elastic materials or deformable hinges to facilitate this manipulation without substantially altering the geometry of the lens support structure 2105. The fixation arm 2120 can have a length such that when the fixation arm 2120 bends 180 degrees back towards its origin with the lens support structure 2105, the terminal end 2102 of the fixation arm 2120 can be positioned over at least a portion of the lens support structure 2105. Each of the fixation arms 2120 of the device 2100 can have a bend or just a selection of the fixation arms 2120 can have a bend (e.g., one, two, up to less than all fixation arms 2120). FIGS. 11A-11F, 12A-12C, 13A-13E show two of the fixation arms 2120 have a bend B and one fixation arm is substantially co-planar with a plane of the lens support structure 2105.

One or more of the fixation arms 2120 of the devices described herein can be manufactured to have a non-planar geometry at rest and may be biased towards the folded configuration that allows for easy viewing of at least a portion of the fixation arm 2120 through a pupil once the device 2100 is implanted, but prior to externalization of the anchor 2125. The fixation arm 2120 having this configuration can be more easily grasped and manipulated by a user so that it can be urged into an unfolded configuration for sutureless fixation. A fixation arm 2120 manufactured to have a bias in a resting state or that is curved or bent in a resting state includes a fixation arm 2120 having that shape when the device 2100 is outside the eye and ready for implantation. In some implementations, the fixation arm 2120 can take on the curved, folded, or bent shape after implantation in the eye (e.g., the posterior chamber), but before fixation of the anchors. For example, one or more fixation arms 2120 can be formed of a material that has a first shape outside the eye, takes on a curved shape upon implantation in the eye that is different from the shape of the arm 2120 prior to implantation in the eye, and that can be unfolded into a substantially straight shape upon externalization of the anchor 2125.

A fixation arm 2120 that has the bias towards a folded or curved shape (e.g., having a bend along its length between its origin portion 2103 and its terminal end 2102) can be visualized through the pupil, grasped, and manually unfolded and/or stretched in order to fix the anchor 2125 of the arm 2120 trans-sclerally. The configuration and/or radius of curvature of the curve, bend, or fold as well as the directional orientation of the curve, bend, or fold can vary so long as at least a portion of the fixation arm 2120 (e.g., the anchor 2125 and/or the terminal end portion coupled to the anchor 2125) is visible to a user through the diameter of the pupil of the patient, preferably a dilated pupil of the patient. In some implementations, this means at least a portion of the fixation arm 2120 is positioned over at least a portion of the lens support structure 2105 and radially inward of its outer region 2111. The distance the portion of the arm 2120 extends radially inward of the outer region 2111 can vary.

The portion can extend to be over a location adjacent to the outer region 2111 that is not over the outer region 2111 in the orientation a central axis CA extending anterior-to-posterior through the central opening 2115. In this implementation, the distance between the central axis CA of the device to the portion extending over is greater than the distance between the central axis CA of the device and the outer region 2111. The portion can extend to be over the outer region 2111. In this implementation, the distance between the central axis CA of the device to the portion is the same as the distance between the central axis CA of the device and the outer region 2111. The portion can extend to be over a location radially inward to the outer region 2111. In this implementation, the distance between the central axis CA of the device to the portion is less than the distance between the central axis CA of the device and the outer region 2111. The portion can extend to be over the central opening 2115. In this implementation, the distance between the central axis CA of the device to the portion is less than the distance between the central axis CA of the device and the inner wall 2109 defining the central opening 2115. The central axis CA of the device can be coaxial with the center of the central aperture 2115.

A portion of the fixation arm (e.g., the terminal end 2102 and/or the anchor 2125) can be positioned over a portion of the lens support structure 2105 and at the same time also over a portion of the central opening 2115. For example, the anchor 2125 can have a dimension such that at least a portion of the anchor 2125 is positioned over at least a portion of the lens support structure 2105 and another portion of the anchor 2125 is positioned over at least a portion of the central opening 2115.

The fixation arms 2120 biased towards a curved configuration can curve towards an inner or a central portion of the device, including, but not limited to, the actual center of the device or the central axis CA or the center of the central aperture 2115. The center of the device 2100 is the center of the circle formed by the central aperture 2115 (in the instance where the central aperture 2115 is circular). The central axis CA of the device extends through the center of that circle in an anterior-to-posterior direction (i.e., a top-to-bottom direction). If the central aperture 2115 is substantially non-circular, the center of the device is a symmetrical center of the central aperture 2115 along the central axis CA extending anterior-to-posterior direction. A fixation arm that is biased into a folded or curved configuration such that its anchor extends towards a center of the device or towards the central axis CA of the device need not require an axis through the anchor of the arm to intersect the actual center or intersect the central axis CA of the device. "Toward the center" or "toward the central axis" with regard to the inwardly biased fixation arms includes an arm having a curve so that the terminal end of the fixation arm extends back toward a portion of the device in a generally inward direction as opposed to the terminal end of the straight fixation arm, which extends in a generally outward direction away from the lens support structure. The curved fixation arm can be biased toward any central portion of the device and need not point directly at the actual center of the device. The curved fixation arms can be angled relative to the actual center.

The device can include at least some of the fixation arms extending back towards a center of the device. The device 2100 can include a lens support structure 2105 and three fixation arms 2120. Two fixation arms 2120_a_, 2120_b_ can be biased into a folded configuration in which a bend B is present between the origin 2103 and the terminal end 2102 of the arms. The third fixation arm 2120_c_ can be substantially straight and has no bend B between its origin 2103 and its terminal end 2102 so that it extends substantially orthogonal relative to the lens support structure 2105 along a single axis L. The anchor 2125 of the respective fixation arms 2120_a_, 2120_b_ can project back towards a center of the device. The anchors 2125 of the fixation arms 2120_a_, 2120_b_ can have at least a first portion that overlaps at least a portion of the lens support structure 2105 and/or at least a second portion that overlaps at least a portion of the central opening 2115. An axis can be drawn through the anchor 2125 of each arm 2120_a_, 2120_b_ illustrating the direction the anchor 2125 is projecting away from the bend B between the arm's origin 2103 and the arm's terminal end 2102 and towards a center of the device. The axes of the arms can, but need not intersect the central axis CA. Thus, the arms can be biased towards a folded configuration in which the anchor projects back toward a center of the device, but need not extend along an axis that intersects the central axis CA or the actual center of the device.

Where the fixation arms are described as being "folded" or "bent" or "curved" or having a configuration that is "folded" or "bent" or "curved", the angle of the fixation arms relative to a longitudinal axis along its length can change gradually and uniformly, or can change more sharply or abruptly such that an angle is formed. The folded configuration can describe the inward bias of the fixation arm at rest or prior to implantation where the fixation arm extends outward from the support structure along a first axis and curves anteriorly or posteriorly relative to a plane of the support structure back towards a central portion of the device. The support structure of the device when implanted is configured to lie substantially parallel to the Z-plane (vertical plane) of the eye. The folded configuration can include a geometry in which the fixation arm curves away from this plane of the support structure (e.g., within a transverse plane) so that at least a portion of the fixation arm is positioned anterior to another portion of the device (e.g., over itself, the lens support structure, and/or the central opening). The folded configuration need not mean the fixation arm portions are over and also in contact with each other. Preferably, the portions of the fixation arm are spaced a distance away from each other, the distance being along the central axis CA of the device. The folded configuration also need not mean a creased or sharply angled folding. The folded configuration can mean a radius of curvature exists between the origin of the fixation arm at the support structure and the terminal end of the fixation arm.

The folded configuration can also include a fixation arm that curves within the plane of the lens support structure rather than away from the plane of the lens support structure. The anchors 2125 of the respective fixation arms 2120_a_, 2120_b_ can project inwardly from the bend B of the arm so that the anchors 2125 remain substantially within the same plane as the plane of the lens support structure. An axis can be drawn through the anchor 2125 of each bent arm 2120_a_, 2120_b_ illustrating the direction the anchor 2125 is projecting away from the bend B between the arm's origin 2103 and the arm's terminal end 2102 and towards a center of the device. The fixation arms 2120_a_, 2120_b_ biased towards the folded configuration can have anchors 2125 that project towards the center of the device. The axes of the arms 2120 could, but need not intersect the central axis CA A portion of the arm 2120 that is positioned over at least a portion of the support structure 2105 can include that portion being over as well as positioned radially inward of an outer region 2111 of the support structure 2105. The portion of the arm 2120 that is positioned over at least a portion of the support structure 2105 can include that portion being positioned radially inward of and over the central opening 2115. In these instances, "radially inward" need not also mean within the same plane. Preferably, the portion of the arm 2120 is positioned over the portion of the support structure within a different plane from the plane of the support structure. The portion of the fixation arm 2120 (e.g., anchor 2125 and/or terminal end 2102) can terminate anterior or posterior to the lens support structure 2105 at a diameter that is central to the outer perimeter of the lens support structure 2105. The portion can be located over the portion of the lens support structure relative to the central axis CA of the device that extends anterior-to-posterior through the central opening 2115. Where the portion of the fixation arm 2120 is described as being over the portion of the lens support structure, the portion of the fixation arm 2120 may also be over the central opening 2115 defined by the lens support structure 2105.

Where a portion of the arm 2120 is described herein as being "over" another portion of the device 2100 (e.g., itself, the lens support structure 2105, and/or the central opening 2115), the portion of the arm 2120 can generally overlap that portion of the device in space and need not require a particular direction relative to the retina. Thus, "over" may be used generically herein to refer to an overlap in the space surrounding the device and can, but need not require the spatial overlap to be in a generally anterior direction relative to the retina. A portion that is described as being "over" another portion can, during use, be positioned posterior to it relative to the retina. The arm 2120 that is biased into the folded configuration may only be referred to herein as "over" or "overlapping" another part of the device even though it may also, during use, be positioned "under" or "posterior" to another part of the device relative to the retina. For the sake of simplicity, each alternative may not be reiterated at each instance throughout the disclosure. The arms can be curved to position at least a portion of the arm over an anterior-facing portion of the device such that the portion is generally vaulted above the device along the central axis CA. The arms can be curved to position at least a portion of the arm over a posterior-facing portion of the device such that the portion is generally vaulted below the device along the central axis CA. The arms can be curved to position at least a portion of the arm within the same plane so that it is neither over the anterior-facing portion nor over the posterior-facing portion of the device. Any of a variety of configurations of the fixation arms are considered herein so that at least a portion of the arms are visible through a dilated pupil. The mechanisms can vary by which the bent fixation arms 2120 that are biased towards the folded configuration become unfolded to take on a straight configuration. The arms can be unfolded mechanically, electromagnetically, and/or thermally.

In some implementations, the fixation arm 2120 may be unfolded mechanically along a single axis of the arm. The fixation arm 2120, at rest, need not be biased into a folded configuration that has a bend or that curves. For example, the fixation arm 2120 may be biased into a folded configuration in which the arm 2120 is compressed longitudinally along a single axis. The arm 2120 be extend along the single axis orthogonally outward from the lens support structure between its origin portion 2103 and its terminal end portion 2102. The length of the arm 2120 in the folded configuration can be shorter between origin portion 2103 and terminal end portion 2102 such that the anchor 2125 of the arm 2120 is positioned more centrally within a smaller diameter than when in the unfolded configuration. Once the device is implanted in the eye, but before externalization of the anchor 2125, the arm 2120 may be telescoped outward to extend its length such that it can be externalized. The mechanical unfolding by telescoping can be due to nested components of the arm 2120 sliding over each other to provide greater length when unfolded or a shorter length when folded. The mechanical unfolding by telescoping can also be due to a single elastic component configured to fold into itself for a shorter length for visualizing through the pupil and unfold out of itself for a longer length during externalization.

In some implementations, the fixation arm 2120 may be unfolded or folded thermally. For example, the fixation arm 2120 can be in a first shape at room temperature (folded or straight) and change to a second shape at body temperature or thereabouts (heated to 35° C.). This can also be effected by chemical means (e.g., hydration) or mechanical means (cutting a restrictive feature).

The fixation arm 2120 can be produced from elastic or inelastic material. For example, the fixation arm 2120 can be formed of an inelastic material and have a 3-dimensional shape that provides for the elasticity. The 3-dimensional shape can vary as described elsewhere herein, including a C-shape, Z-shape, S-shape, or other 3-dimensional shape. The fixation arm 2120 provides sufficient support to maintain an IOL 110 or other device while not imparting excessive force on scleral tissue. An optimal design would have a wide operable range of tensions and stability in order to be able to meet both parameters in eyes of varying sizes and with incisions in varying locations. One means of modifying the fixation arm design is to incorporate spring-like structures. These can include traditional compression based haptic designs like J-Loop, C-Loop, Closed Loop, Kellman Haptics, plate haptics, or other haptic designs common to IOLs. Alternatively, the device 2100 can incorporate a tension-based haptic such as a simple linear elastic cord. Alternatively, the tension design can be modified with a V-shaped, Z-shaped or S-shaped feature to decrease the tensile resistance of the fixation arm 2120.

The fixation arm 2120 can have a texture or features that allows it to be pulled through sclera in one direction, but there is resistance in the opposite direction to minimize the chance of slippage the fixation arm 2120. The texture or feature can be provided by the material itself or designed into the fixation arm 2120. For example, the fixation arm 2120 can be barbed and formed from a material integrated into an outer structure. In this way, a barbed internal structure may be able to function as a barb while hiding the sharp edges commonly associated with a barb. An example would be a rigid plastic structure embedded in a soft elastomeric structure.

The fixation arms 2120 can be formed of a flexible material that has memory and is not malleable. The flexible material of the fixation arms 2120 can include any of a variety of elastomers including polyurethanes, hydrophobic acrylics, hydrophilic acrylics, Nylon, Polyimide, PVDF, natural polyisoprene, cis-1,4-polyisoprene natural rubber (NR), trans-1,4-polyisoprene gutta-percha, synthetic polyisoprene (IR for isoprene rubber), Polybutadiene (BR for butadiene rubber) Chloroprene rubber (CR), polychloroprene, Neoprene, Baypren etc., Butyl rubber (copolymer of isobutylene and isoprene, IIR), Halogenated butyl rubbers (chloro butyl rubber: CIIR, bromo butyl rubber: BIIR), Styrene-butadiene Rubber (copolymer of styrene and butadiene, SBR), Nitrile rubber (copolymer of butadiene and acrylonitrile, NBR), also called Buna N rubbers Hydrogenated Nitrile Rubbers (HNBR) Therban and Zetpol, EPM (ethylene propylene rubber, a copolymer of ethylene and propylene) and EPDM rubber (ethylene propylene diene rubber, a terpolymer of ethylene, propylene and a diene-component), Epichlorohydrin rubber (ECO), Polyacrylic rubber (ACM, ABR), Silicone rubber (SI, Q, VMQ), Fluorosilicone Rubber (FVMQ), Fluoroelastomers (FKM, and FEPM) Viton, Tecnoflon, Fluorel, Aflas and Dai-El, Perfluoroelastomers (FFKM) Tecnoflon PFR, Kalrez, Chemraz, Perlast, Polyether block amides (PEB A), Chlorosulfonated polyethylene (CSM), (Hypalon), Ethylene-vinyl acetate (EVA), Thermoplastic elastomers (TPE), resilin and elastin, Polysulfide rubber, and Elastolefin.

The arms 2120 made of a flexible material that is formed into a shape can be flexed away from the formed shape, but has memory to return to the formed shape. In other words, the flexible fixation arms 2120 can be flexed or unfolded away from their folded configuration, but cannot be urged into a different shape that is retained without some kind of anchoring fixation. For example, one or more of the flexible fixation arms 2120 can be formed into a bent shape. For example, the arm can include a 180 degree bend or curve from its origin 2103 with the support structure 2105 to the terminal end 2102 near the anchor 2125. The arm 2120 can maintain this bent shape when the device is at rest and no forces are applied to the arm 2120 such that the arm 2120 is biased towards a folded configuration. In other words, the arm 2120 in its unbiased state is bent. The bent fixation arm 2120 can be flexed away from this bent shape to take on a straight shape or an unfolded configuration such that the entire arm 2120 extends and is positioned straight relative to the longitudinal axis L. When flexed into a straight shape, the arm 2120 is biased to return to the bent shape or the folded configuration. If the flexing force on the fixation arm 2120 is released, the arm 2120 will return to its resting bent shape. However, when in use, the fixation arm 2120 is anchored trans-sclerally and the anchor 2125 at the terminal end 2102 of the arm 2120 positioned outside the sclera. The arm 2120 is tensioned to remain in the straight shape.

In other implementations, the fixation arms 2120 can be formed of or incorporate a material that is malleable such that the fixation arms 2120 can be bent or formed into a particular shape. The malleable fixation arms 2120 can be formed of a material such as implant-grade metals or plastics including gold, silver, platinum, stainless steel, Nitinol, nickel, titanium, polypropylene, polyethylene, nylon, PVDF, polyimide, Acetal, and PEEK. The material of the fixation arms 2120 is configured to be cut and removed from the device 2100 during an implantation procedure as discussed elsewhere herein.

The one or more fixation arms 2120 can have a Young's modulus that is less than about 1000 MPa, or less than about 500 MPa, or less than about 250 MPa, or less than about 100 MPa, or less than about 50 MPa, or less than about 25 MPa. The one or more fixation arms 2120 can have a Young's modulus that is less than about 20 MPa, for example, between about 0.01-about 1.0 MPa. The fixation arms 2120 can be very soft and apply very little force because they are designed to be under tension to anchor the support structure 2105 rather than having a compression spring force to anchor the support structure 2105 or a more rigid penetrating force that a barb or other fixation haptic can provide.

In some implementations, the fixation arms 2120 can each have a length between the origin 2103 and the terminal end 2102 that is about 2 mm to about 6 mm. The fixation arms 2120 each can have the same length. The length of the fixation arms 2120 that extends through the sclera can having a thickness or width that is minimized to reduce the overall size of the wound through which the arms 2120 extend. The maximum width of the trans-scleral portion of the fixation arms near the terminal end 2120 where the anchor 2125 is positioned can be no greater than about 2.0 mm, no greater than about 1.5 mm, no greater than about 1.0 mm, no greater than 0.75 mm, no greater than 0.50 mm.

FIGS. 11A-11F, 12A-12C, 13A-13E show implementations of devices 2100 having two fixation arms 2120*a*, 2120*b* that have inward bias and a third fixation arm 2120*c* that does not have inward bias and is straight. Additionally, the third fixation arm 2120*c* can have a geometry that makes it less flexible than the other fixation arms 2120*a*, 2120*b*. The third fixation arm 2120*c* can incorporate a region between the origin 2103 and terminal end 2102 that is wider than the other two fixation arms 2120*a*, 2120*b* and can have a higher cross-sectional area. FIGS. 16A-16C and 17 shows a region of a fixation arm 2120 that is wider. FIG. 16B illustrates a width W1 of the arm 2120 near the terminal end 2102 can be less than a width W2 of the arm 2120 away from the terminal end 2102 of the arm 2120. The width W2 of the arm 2120 away from the terminal end 2102 can provide a degree of bulk and stability while the width W1 near the terminal end 2102 can minimize the trans-scleral portion of the arm 2120.

Figure 17:
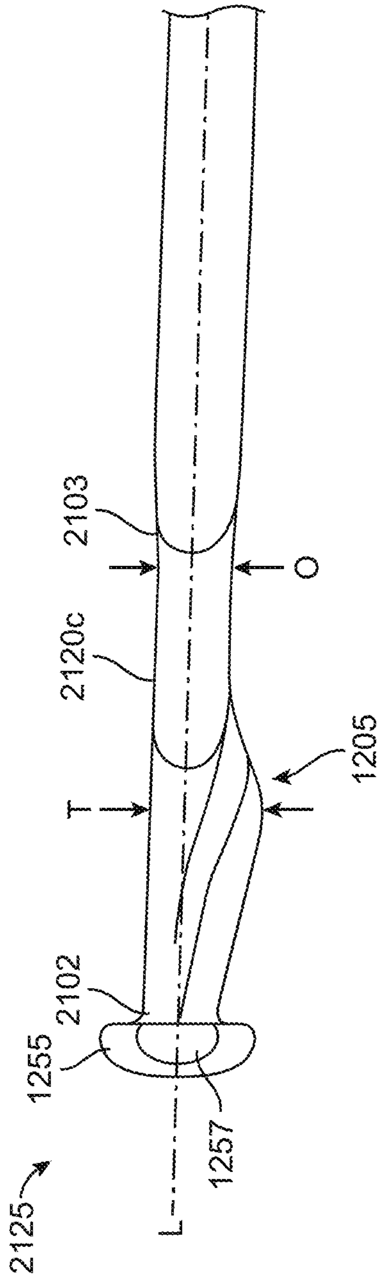
FIG. 17 is a side view showing a straight, leading fixation arm designed to bias the device anteriorly to prevent posterior drift during anchoring footplate externalization.

Each fixation arm 2120*a*, 2120*b*, 2120*c* can be positioned one at a time during the surgical procedure. As described elsewhere herein, the leading fixation arm 2120*c* can be a straight configuration and the trailing fixation arms 2120*a*, 2120*b* can be curved. The weight of the device can cause the first implanted or leading fixation arm 2120*c* to bend following externalization such that the device 2100 tilts posteriorly toward the retina. In this scenario, a surgeon can locate the device in a more posterior position. However, this can increase the risk of intraoperative tissue damage due to the manipulation of tools near the retina. In some implementations, the leading fixation arm 2120*c* can be mechanically and/or geometrically reinforced to reduce the likelihood of posterior drift. The leading fixation arm 2120*c* can be produced out of a material that is resistant to such deformation. The material can be any implant grade plastic or metal that can cantilever the device following externalization of the anchor 2125 of the leading fixation arm 2120*c*. Suitable materials include, but are not limited to, PMMA, rigid silicones, nylon, hydrophilic and hydrophobic acrylics, PEEK, polyimide, stainless steel, titanium, Nitinol, and others. The more rigid material can be used to form the entire leading fixation arm 2120*c* or just a portion of the leading fixation arm 2120*c*. The leading fixation arm 2120*c* may be formed of a softer material embedded with a more rigid material. In an implementation, the leading fixation arm 2120*c* can include a region 1205 of mechanical reinforcement between its origin 2103 at the support structure 2105 and its terminal end 2102 where it is coupled to an anchor 2125 (see FIG. 17). The region 1205 can achieved by increasing a thickness of the fixation arm 2120*c* or embedding a rigid section of plastic into a softer material. FIG. 17 shows an increased thickness (arrows T) at the mechanical reinforcement region 1205 compared to a Thickness (arrows O) of the arm near its origin 2103 with the support structure. The region 1205 can be spaced a distance away from the support 2105, for example, close to or adjacent the anchor 2125. The region 1205 can have an increased thickness designed to specifically reduce the likelihood that the device 2100 drifts posteriorly, while not impacting the ability externalizing the anchor 2125 of the fixation arm 2120. For example, the fixation arm 2120 can have a tapered thickness designed to limit deflection in the posterior direction. The tapered geometry can be thinnest near the footplate anchor 2125 and thicken centrally. The posterior surface of the fixation can serve to bias the device anteriorly relative to the eye. The angle of contact of the posterior surface of the fixation arm 2120 and the wound can bias the device 2100 in a way that reduces the practical risk of a posterior deflection of the fixation arm 2120. Additional bulk can further limit the deflection of the device and the proximity to the retina.

Figure 12A:
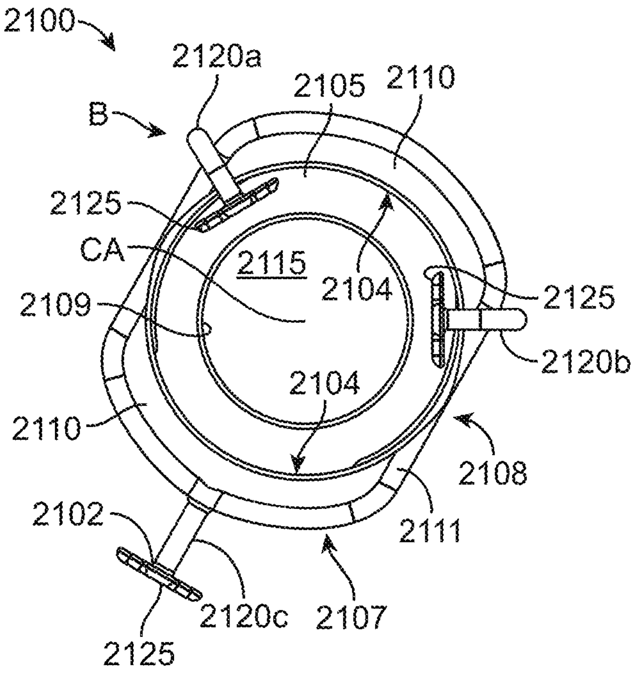
FIGS. 12A-12C show an interrelated implementation of a device having awnings configured to accommodate an IOL.
Figure 12B:
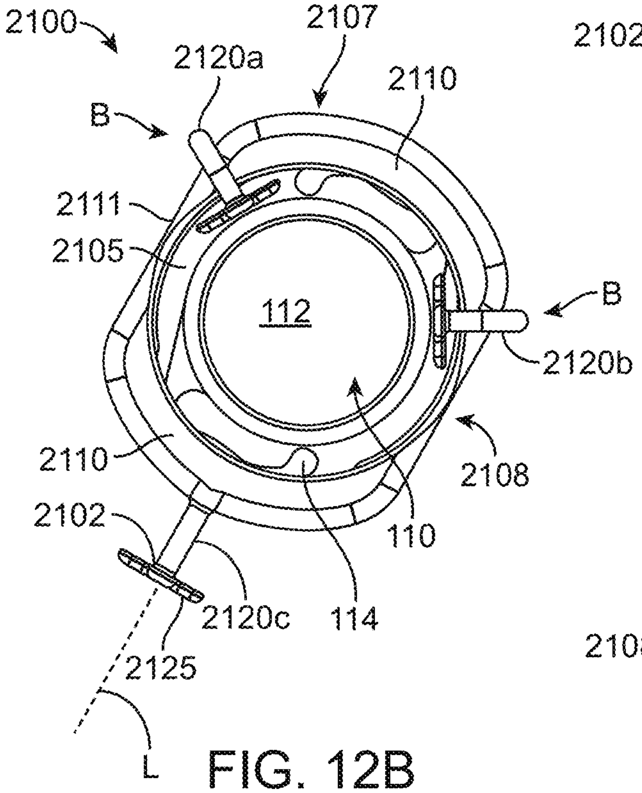
Figure 12C:
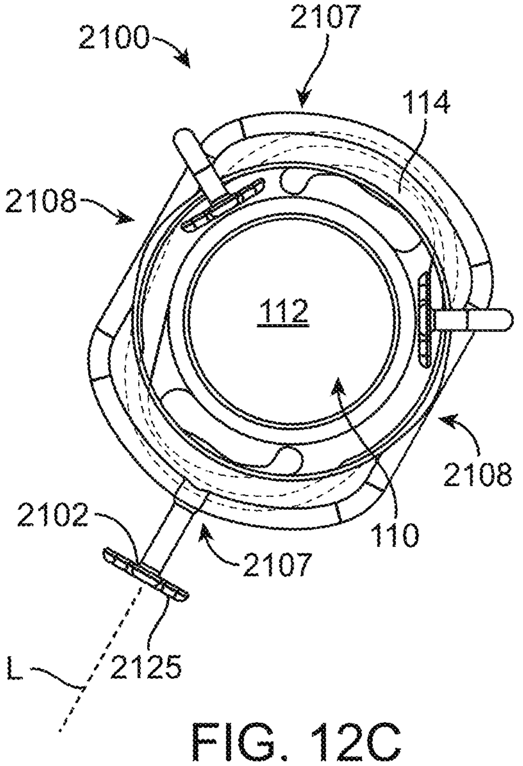
Figure 13A:
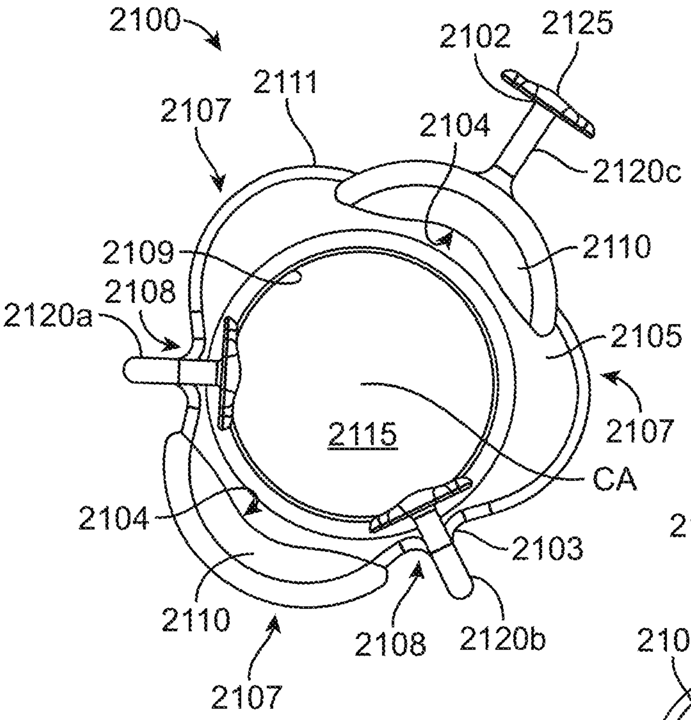
FIGS. 13A-13E show an interrelated implementation of a device having awnings configured to accommodate an IOL.
Figure 13B:
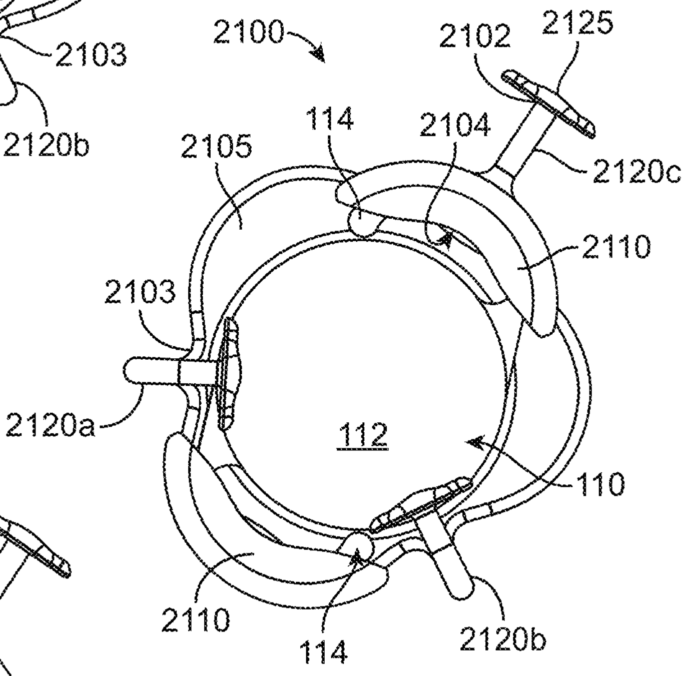
Figure 13C:
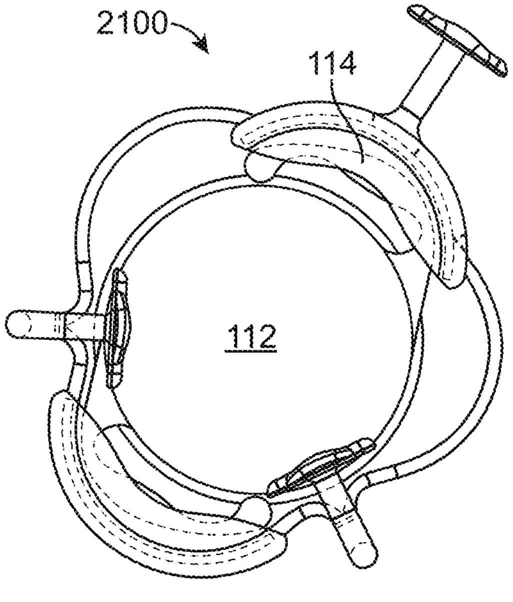
Figure 13D:
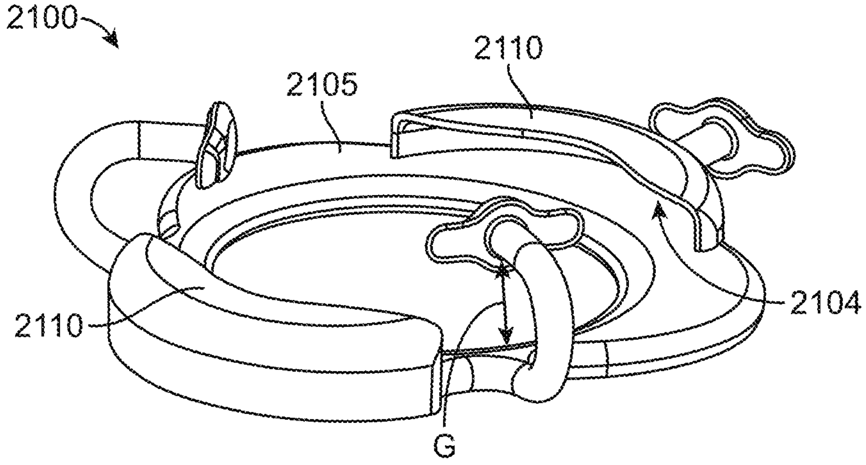
Figure 13E:
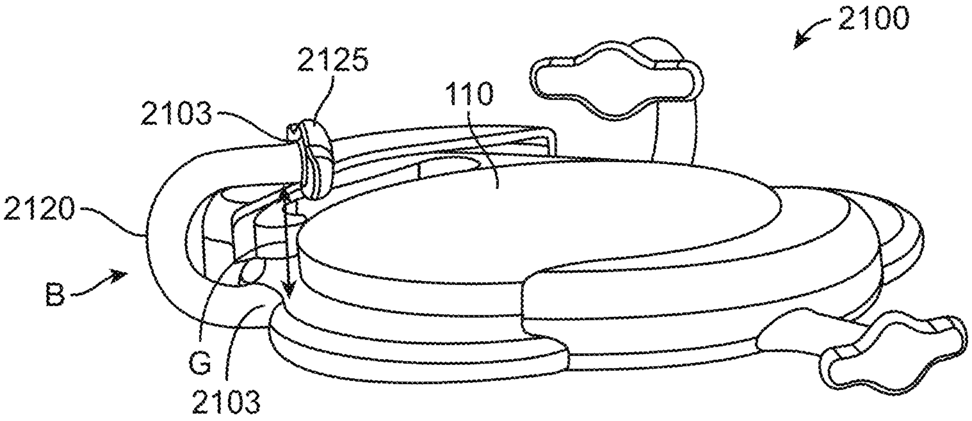

FIGS. 12A-12C illustrate another implementation of a device 2100 having a circular central aperture 2115 and a non-circular outer perimeter 2111. The non-circular outer perimeter 2111 in FIGS. 12A-12C is a rounded rectangle shape having two substantially flat, elongate sides 2108 and two substantially rounded, short sides or lobes 2107. The recesses 2104 formed by the awnings 2110 may project out over the anterior-facing surface of the lens support structure 2105 such that they are positioned generally opposite one another along a major axis of the rectangle and spaced to accommodate the span of the IOL 110 haptics 114. For example, the awnings 2110 may project out over the anterior-facing surface of the lens support structure 2105 on the short sides of the rounded rectangle (i.e., at the location of the lobes 2107) to accommodate the span of the IOL 110 therebetween within the recesses 2104 along the long sides 2108 (see FIG. 12C).

Three fixation arms 2120 can be coupled to the lens support structure 2105. At least one of the fixation arm 2120*a*, 2120*b* can be biased into the folded configuration as described elsewhere herein. One fixation arm 2120*c* can be a leading fixation arm that extends along a single axis orthogonally relative to the lens support structure 2105 so that its terminal end 2102 coupled to the anchor 2125 projects outward away from the center axis CA of the aperture 2115. The leading fixation arm 2120*c* can be coupled to the lens support structure 2105 at a location of a lobe 2107 and the other fixation arms 2120*a*, 2120*b* can be coupled away from the lobe 2107 of the leading fixation arm, for example, on opposite sides 2108 so that the opposite lobe 2107 projects outward between the arms 2120*a*, 2120*b* (see FIGS. 12A-12B).

Figure 15:
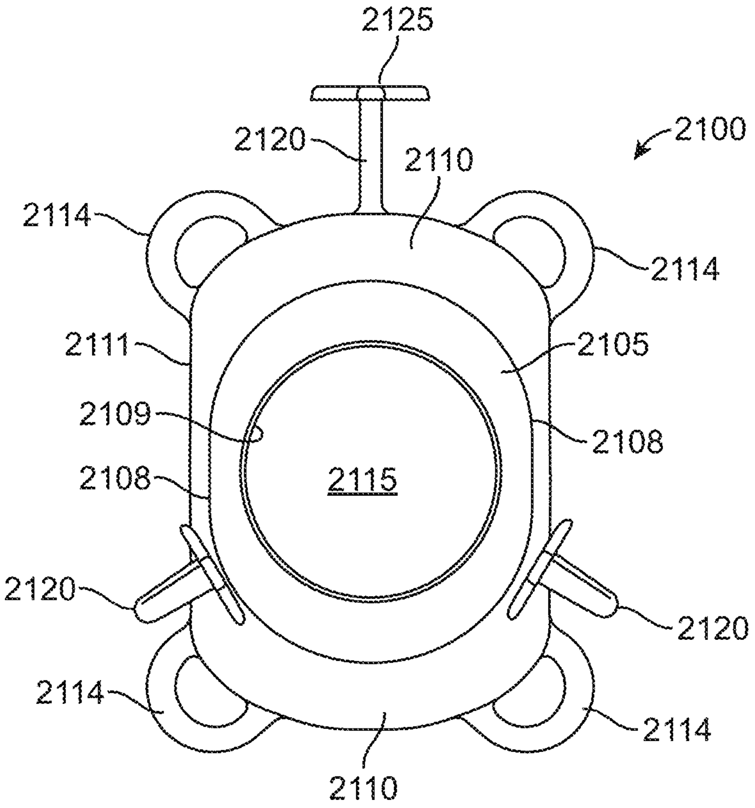
FIG. 15 shows a top down view of an interrelated implementation of a device having a plurality of radially extending bumpers and plurality of trans-scleral fixation arms.

FIG. 15 shows an interrelated implementation of a device 2100 having awnings 2110. The device 2100 additionally incorporates a plurality of bumpers 2114 to assist in the centration of the device 2100 within the eye. The device 2100 can include four bumpers 2114 projecting outward from each corner of the lens support structure 2105. The bumpers 2114 can be substantially ring-shaped or incomplete rings having a C-shape. The ring-shaped bumper 2114 can include a first end and a second end that are both coupled to the lens support structure 2105. The C-shaped bumper 2114 can have one end coupled to the lens support structure 2105 and the second end that remains separated from the lens support structure 2105. Regardless, the shape or configuration, the bumper 2114 can urge the device 2100 away from the adjacent eye tissue. In some implementations, the bumper 2114 can deform slightly upon coming into contact with a ciliary structure. The deformation can be temporary so that the bumpers return to their original shape urging the device 2100 back towards a centralized position within the eye. As with other implementations described herein, the device 2100 can include a plurality of fixation arms 2120 including at least one that is biased into a folded configuration. Preferably, the bumpers 2114 avoid remaining in contact with the ciliary structures once the device 2100 is implanted. The bumpers 2114 can act as a guide during externalization of the fixation arms 2120. The bumpers 2114 can project sufficiently away from the outer perimeter 2111 of the lens support structure 2105 such that the bumpers 2114 abut against the ciliary body 15 and/or within the ciliary sulcus to prevent displacement within the Z-plane to maintain proper alignment of the central aperture 2115 relative to the eye's visual axis during fixation.

Figure 5B:
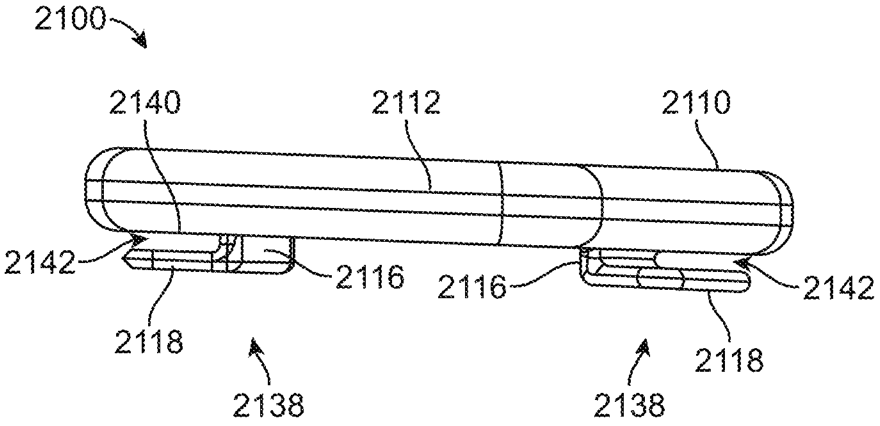
FIGS. 5B and 5C are other views of the device of FIG. 5A.
Figure 5C:
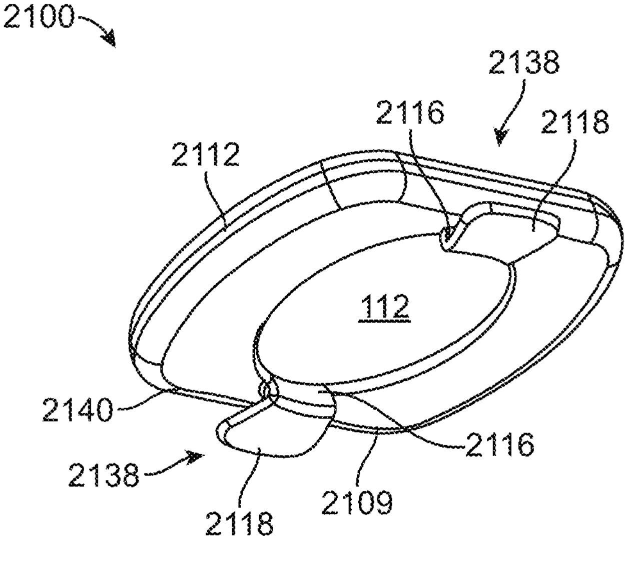

Illustrated herein are various implementations of devices configured to be implanted in an eye and support, stabilize, or otherwise engage with a separate IOL so that the IOL is maintained in optical alignment. The devices described herein can incorporate any of a variety of features in any reasonable combination. For example, where the devices of FIGS. 1A-1F, 2A-2B, 3, 4A-4B are described in the context of incorporating one or more bumpers 2114, the devices may additionally or alternatively incorporate one or more fixation arms 2120 and/or posterior stabilization features 2138. Where the devices of FIGS. 5A-5C are described in the context of having a posterior stabilization feature 2138, they may additionally or alternatively incorporate one or more fixation arms 2120 and/or bumpers 2114. The devices of FIGS. 6A-6E and also FIGS. 8A-8F and FIG. 9A-9B are described in the context of having both bumpers 2114 and posterior stabilization features 2138, they may additionally or alternatively incorporate one or more fixation arms 2120. The same is true of the devices shown in FIGS. 10A-10D as well as the devices shown in FIGS. 11A-11F, 12A-12C, 13A-13E, 15, and 17. Any of a combination of features described herein can be combined with the devices in any of a number of combinations to address various functional purposes.

Figure 18A:
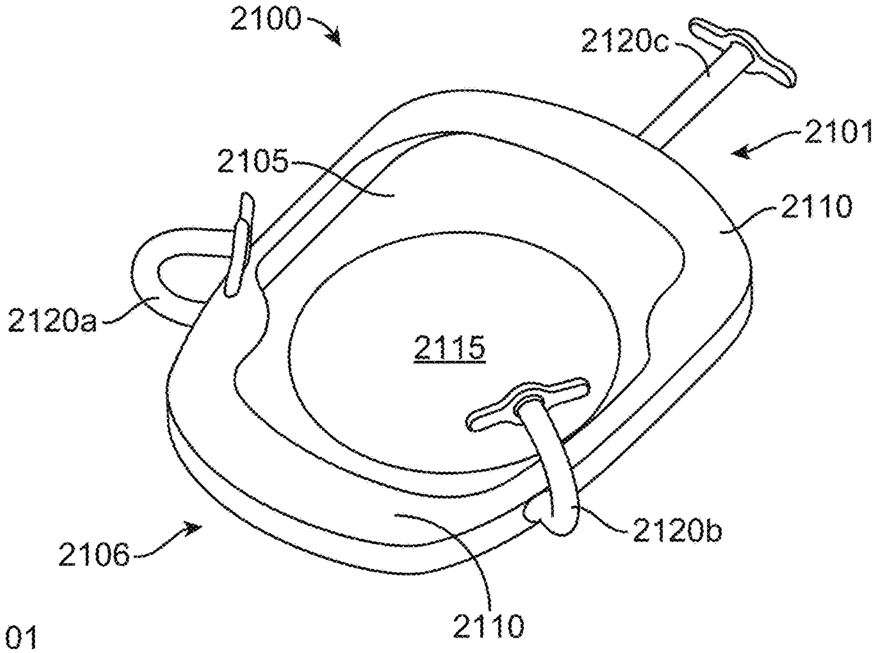
FIG. 18A shows an interrelated implementation of a device incorporating a plurality of trans-scleral fixation arms.

FIG. 18A shows an interrelated implementation of the device 2100 showing the posterior platform 2105 and awnings 2110 forming a chassis having a rectangular shape. The chassis has a leading end 2101 and a tapered trailing end 2106. The trailing end 2106 of the chassis between the trailing fixation arms 2120*a*, 2120*b* may be narrower than a width of the leading end 2101 of the chassis near the leading fixation arm 2120*c*. The trailing end 2106 of the chassis can be at least about 0.2 mm, about 0.3 mm, about 0.4 mm, about 0.5 mm, about 1.0 mm, about 1.5 mm, about 2.0 mm narrower than a width of the leading end 2101 of the chassis.

Figure 18B:
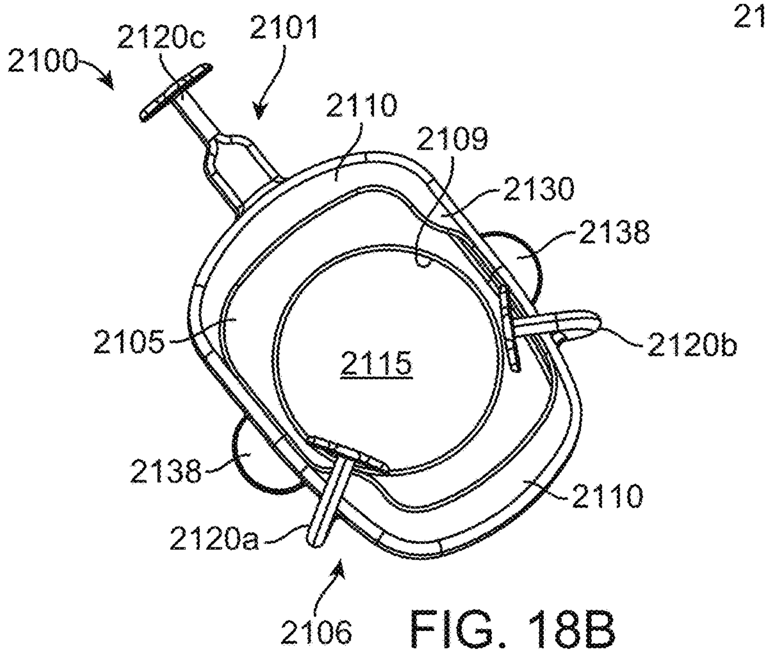
FIGS. 18B-18C shows a top down and perspective views, respectively, of an interrelated implementation of the device incorporating a plurality of trans-scleral fixation arms and a posterior stabilization feature.
Figure 18C:
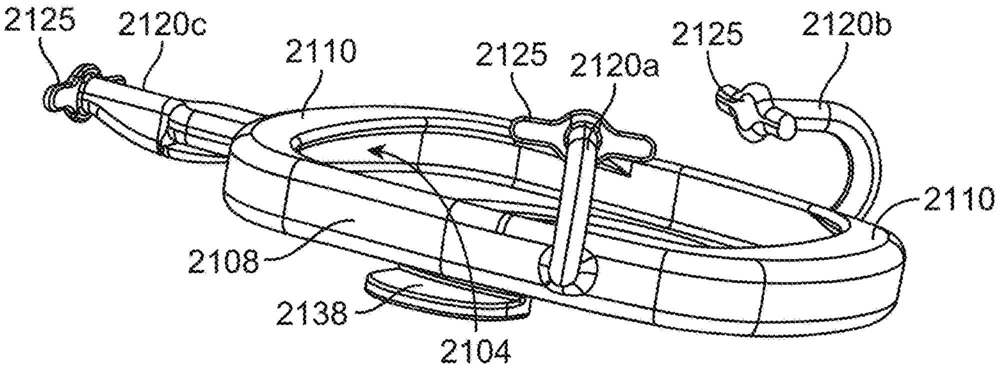
Figure 18D:
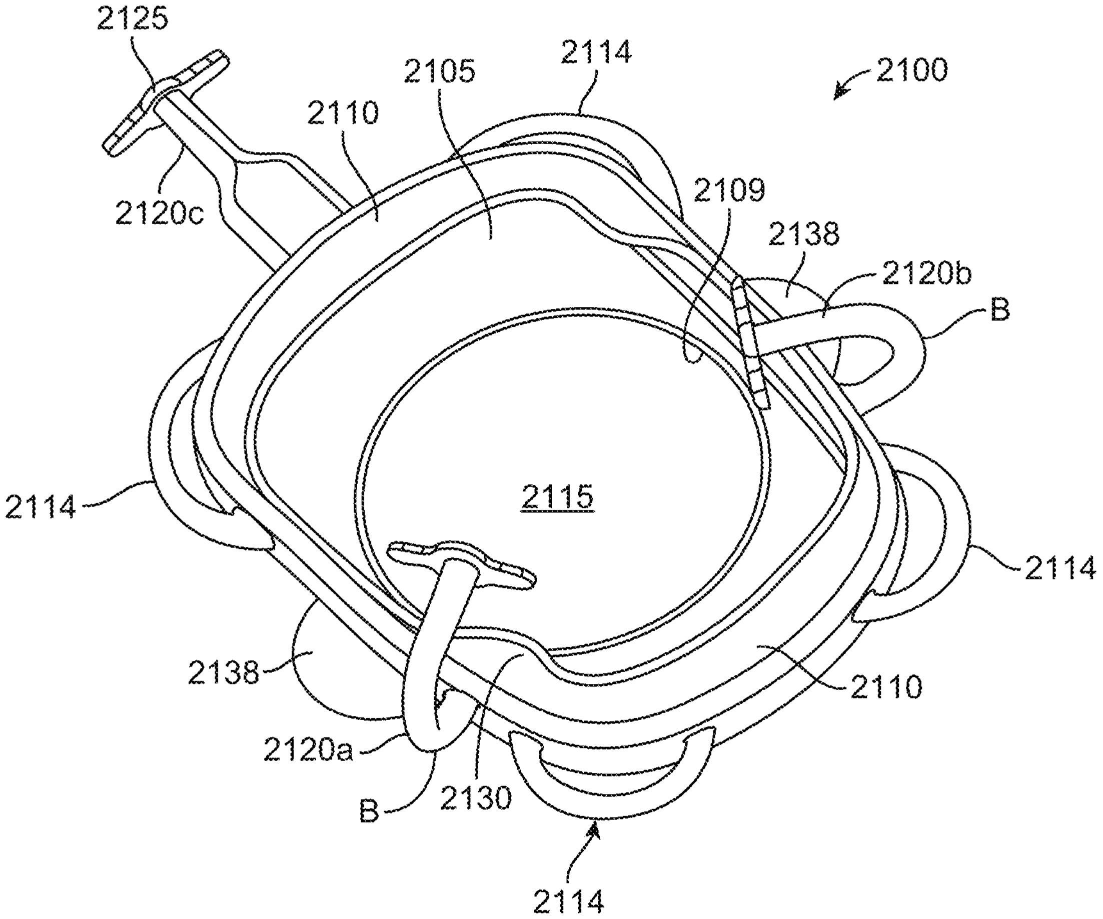
FIG. 18D shows a perspective view of an interrelated implementation of the device incorporating a plurality of trans-scleral fixation arms, a plurality of radially extending bumpers, and a posterior stabilization feature.

FIGS. 18B-18C illustrates a top down and perspective views, respectively, of the device 2100 of FIG. 18A incorporating a plurality of fixation arms 2120 (one or more of which may be biased into a folded configuration) additionally incorporating a posterior stabilization feature 2138. FIG. 18D illustrates the device of FIGS. 18B-18C incorporating a plurality of fixation arms 2120 (one or more of which may be biased into a folded configuration) and a posterior stabilization feature 2138 additionally incorporating a plurality of bumpers 2114.

The fixation arms 2120, once anchored in the eye, can impose forces on the device that can impair the optics of the IOL positioned relative to the device. For example, the posterior platform 2105, awnings 2110, side walls 2112, or other portion of the device 2100, particularly those that form a housing for the IOL, can distort depending on the tension on the fixation arms 2120. The device distortion can be transferred to the IOL and negatively impact the optics. The devices described herein can incorporate one or more features designed to resist distortion due to forces applied on the device whether due to tension of the fixation arms 2120 or forces applied by the eye onto the device 2100.

Figures 18E, 18F, 18G:
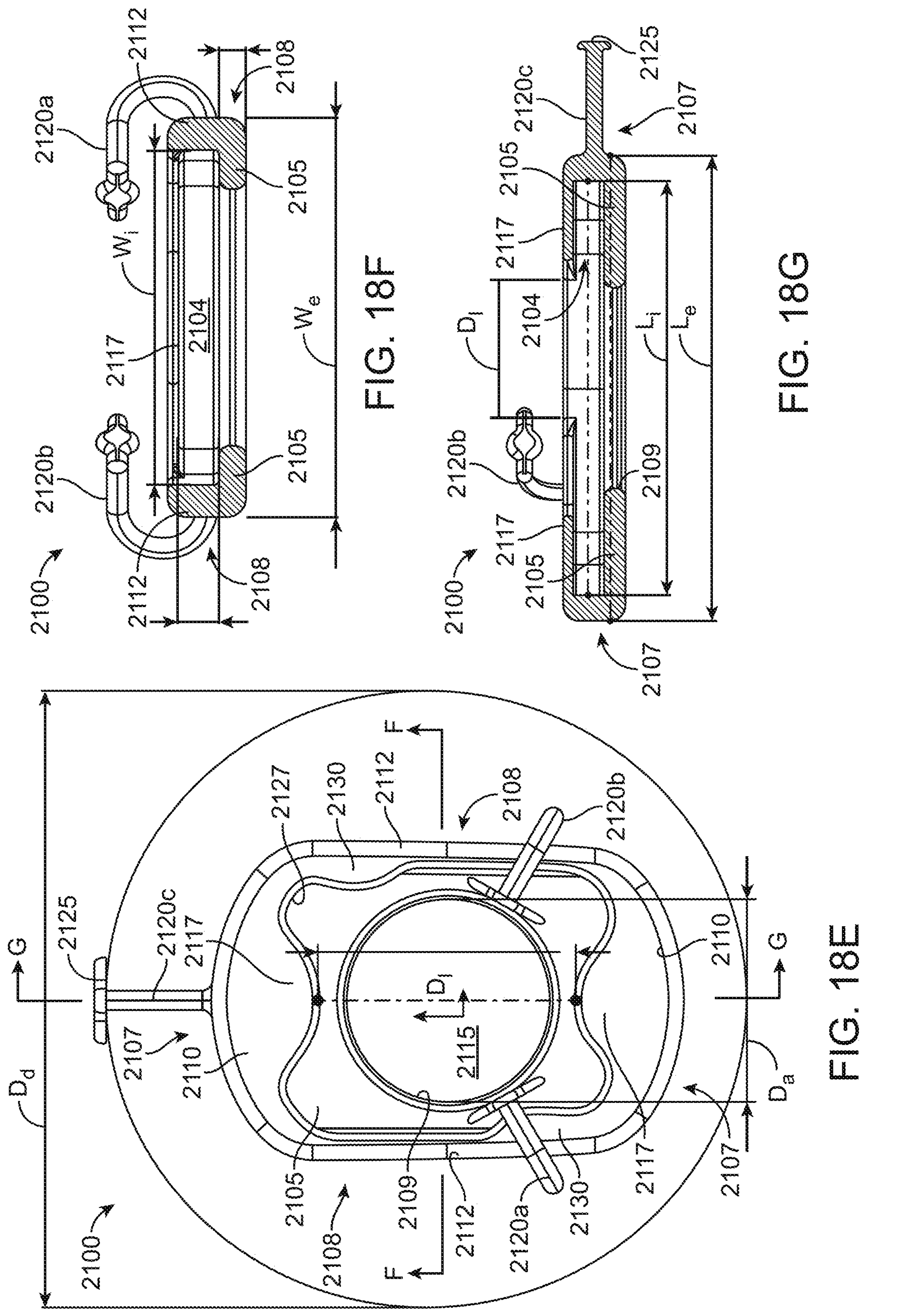
FIG. 18E shows a top down view of an interrelated implementation of the device incorporating a plurality of trans-scleral fixation arms.
FIG. 18F shows a cross-sectional view of the device of FIG. 18E taken along line F-F.
FIG. 18G shows a cross-sectional view of the device of FIG. 18E taken along line G-G.
Figure 18H:
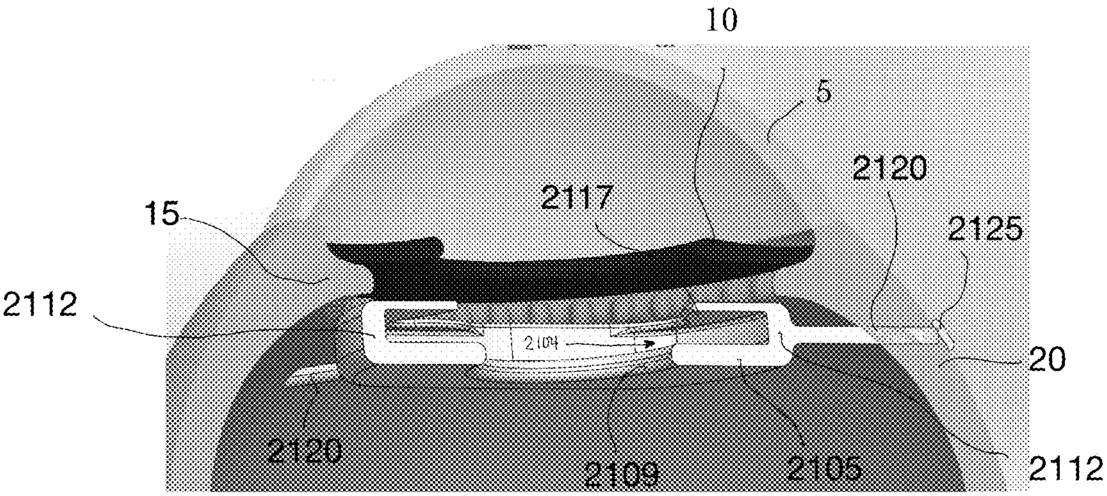
FIG. 18H shows the device of FIG. 18G implanted in an eye.

The devices can incorporate reinforcement material(s) to increase hoop strength and resist distortion, as discussed above with regard to FIGS. 20A-20D, that may or may not increase the material thickness of the region of the device being reinforced. The material thickness of one or more regions of the device 2100 can also be increased to provide increased hoop strength with or without the additional reinforcing materials. FIGS. 18E-18H illustrate an implementation of the device 2100 incorporating a plurality of fixation arms 2120. The posterior platform 2105 and the side walls 2112 are reinforced due to increased material thickness of those regions of the device. FIG. 18F is a cross-sectional view of the device 2100 in FIG. 18E taken along arrow F-F showing an increased cross-sectional thickness of the posterior platform 2105 (e.g., about 0.50 mm) and an increased thickness of the side wall 2112 (e.g., about 0.35 mm up to about 0.60 mm or up to about 1.5 mm). The increased stiffness of the lens support structure provided by the increased material thickness can facilitate easier insertion of the IOL following implantation. The increased material thickness can additionally increase the hoop strength of the central aperture 2115 extending through the posterior platform 2105, which can limit the risk of the IOL accidentally passing through the aperture 2115 upon implantation of the IOL in the device 2100.

The diameter Da of the central aperture 2115 also can be reduced to increase the hoop strength of the posterior platform 2105. For example, the central aperture 2115 can have a diameter that is less than about 5.0 mm down to about 4.0 mm, preferably about 4.75 mm so as not to interfere with the optics of the IOL. The aperture size alone or in combination with the posterior platform thickness and/or side wall thickness can resist distortion of the device that could otherwise be caused by the tensioned fixation arms. The aperture diameter can also limit the risk of accidentally passing the IOL through the aperture 2115 upon implantation due to not just the size, but the increased hoop strength of the aperture 2115. Smaller aperture diameters can increase the hoop strength compared to larger aperture diameters. A stiffer IOL housing limits distortion of the aperture 2115 when placed under tension and/or compression. The increased stiffness of the IOL housing can also facilitate easier insertion of the IOL following fixation in the eye.

The thicker side walls 2112 of the device can reduce the space within which the IOL can be manipulated. To provide more space for IOL manipulation within the recess 2104, the external length along the long axis of the device can be increased to accommodate the thicker side walls 2112 and provide an internal length of the recess along the same axis for IOL insertion and manipulation (see FIG. 18G). The posterior platform 2105 along the long axis of the device can have an external length L e of about 9.2 mm and an internal length $L_i$ along the same axis that is about 8.5 mm such that a thickness of the side wall is about 0.7 mm. To provide additional reinforcement to the device 2100, the side wall cross-sectional thickness can be increased to about 1.2 mm. The platform along the long axis can be increased to about 11 mm such that an internal length $L_i$ along the same axis is about 9.8 mm. The increased cavity length can provide more space within which the IOL can be manipulated that, combined with the increased side wall thickness, provides an external length $L_e$ of the device that is increased. The longer device can be fixated through the pars plana and thus, posterior to the ciliary apex, such that even if the device on the plane of the ciliary apex is too wide, there can still be space for implanting the larger IOL housing (see FIG. 18H). The short axis width can be impacted by the thicker side walls 2112 as well (see FIG. 18F). The posterior platform 2105 along the short axis of the device can have an external width $W_e$ of about 6.60 mm and an internal width $W_i$ along the same axis that is about 6.60 mm such that a thickness of the side wall 2112 is about 0.7 mm. The side wall 2112 cross-sectional thickness can be increased to 1.2 mm as discussed above. The platform 2105 along the short axis can be increased to about 7.4 mm such that an internal Width $W_i$ along the same axis is about 6.2 mm.

The devices described herein are used to support an IOL within an eye. The devices described herein can incorporate one or more features configured to engage with at least a portion of the capsular bag for centration or fixation in the eye. The devices described herein can incorporate one or more features configured to fix and center the device in the eye even where capsular bag support is lacking, for example, due to iatrogenically compromised lens support during the time of surgery or as a late complication of a previous surgery. Whether there is capsular bag support or not, visualization of the device during implantation is important. In some implementations, the curved or biased fixation arms 2120 can allow for direct visualization of the device through the pupil such that the arms 2120 may be more readily grasped, which is particularly useful during externalization and fixation of the device within the eye. The devices described herein can be viewed directly through the pupil even if there are no fixation arms 2120. In some implementations, the anterior geometry of the device 2100 is modified to improve anterior visualization through the pupil. For example, the anterior awnings 2110 can be sized and shaped to have at least a portion that projects inwardly or more centrally than another portion (e.g., towards a center axis extending through the central aperture 2115) such that the centrally-projecting portion of the awning 2110 is visible anteriorly through a dilated pupil without being substantially blocked by the iris. The geometry of the awnings 2110 can be visible relative to the IOL being implanted without impacting the optics of the IOL. This can increase the likelihood that the IOL will be properly secured within the recess 2104 of the device 2100. Post-operative lens dislocation can occur when the IOL haptic is left in a position that is anterior to the device 2100. Uncertainty of lens position can increase surgical time and the potential for tissue trauma as surgeons manipulate the device and/or tissue to confirm lens position relative to the device. Direct visualization of the device 2100 through the pupil lessens this uncertainty, particularly where intra-operative pupil diameter decreases mid-surgery.

Figure 18I:
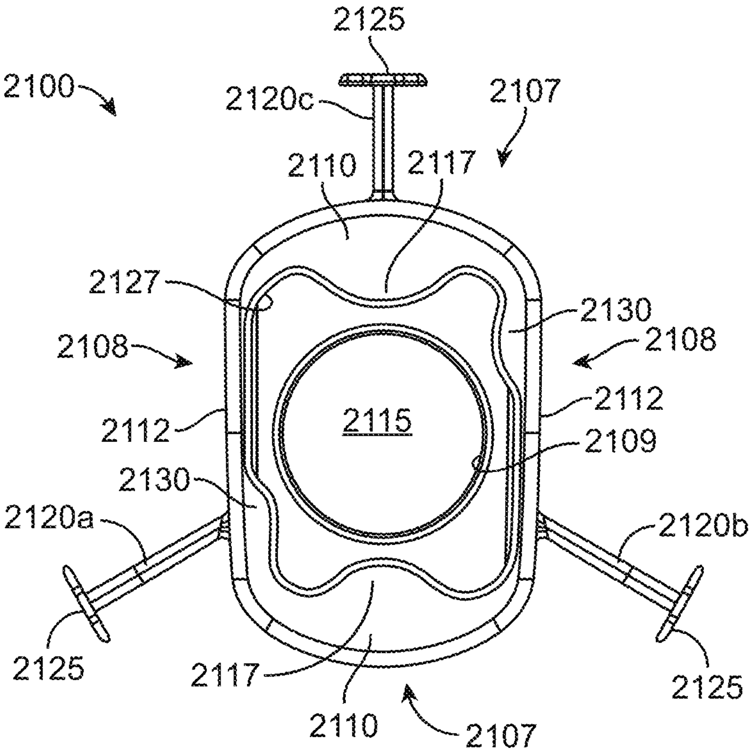
FIGS. 18I-18J show top down and perspective views of an interrelated implementation of the device incorporating a plurality of trans-scleral fixation arms.
Figure 18J:
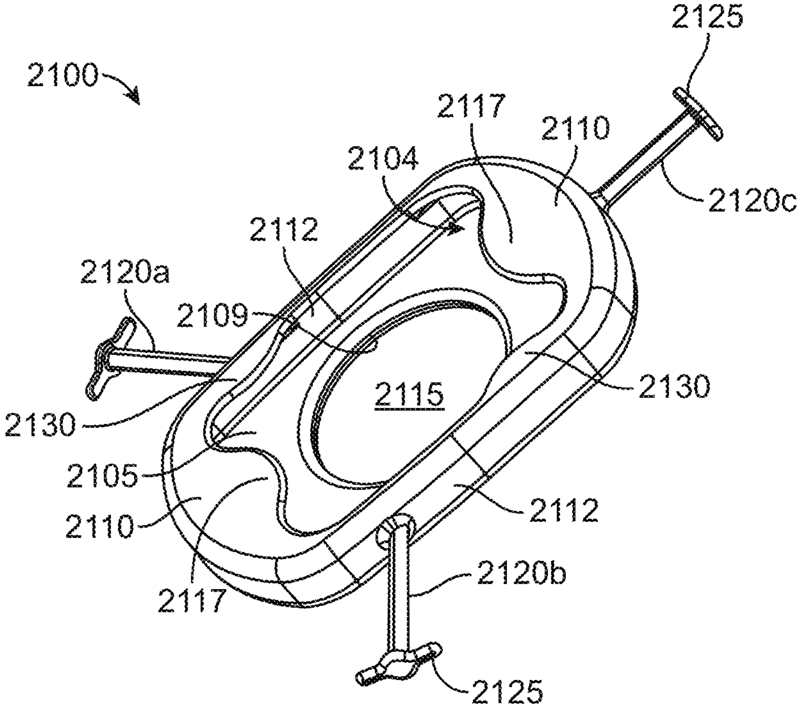

FIG. 18E and also FIGS. 18I-18J illustrate an example of the anterior awnings 2110 having a centrally-projecting visualization feature 2117. The visualization feature(s) 2117 can project centrally to allow for direct visualization of the device 2100 while avoiding interfering with optics of the IOL after implantation. The visualization features 2117 can project sufficiently towards a central axis of the central aperture 2115, for example, at least about 2.5 mm to about 3 mm away from the central axis so that the features 2117 are visible through the pupil during an implantation procedure. The centrally-projecting visualization feature 2117 can narrow an inner dimension of the anterior opening 2127, for example, a distance Di of the anterior opening 2127 along the long axis of the device (see FIGS. 18H and 18G) while the overall dimensions of the anterior opening 2127 remain relatively large for accessing the internal recess 2104. The distance Di along the long axis of the device between the central-most edges of the anterior opening 2127 formed by the opposing awnings' visualization features 2117 can be at least about 7.0 mm down to about 5.0 mm, preferably about 6.0 mm. This distance $D_I$ is selected to be larger than the diameter Da of the central aperture 2115. For example, the diameter $D_a$ of the central aperture 2115 can be about 4.75 mm and the distance $D_l$ between the visualization features 2117 can be about 5.00 mm, about 5.25 mm, about 5.50 mm, about 5.75 mm, about 6.00 mm up to about 7.00 mm. Thus, even where the awnings 2110 incorporate the one or more visualization features 2117, the dimension of the anterior opening 2127 defined by the features 2117 can be larger than the diameter $D_a$ of the central aperture 2115.

The features 2117 shown in FIG. 18E projects centrally away from the leading fixation arm 2120*c* such that coverage provided by the awning 2110 near this arm is greater than coverage provided by the awning 2110 near the corners of the device 2100 where the short sides 2107 meets the long sides 2108. The pair of features 2117 can therefore be positioned on the short sides 2107 of the device and project along the long axis. The visualization features 2117 can alternatively be positioned on the long sides 2108 of the device and project along the short axis (i.e., turned 90 degrees relative to what is shown in the figure). The visualization features 2117 can be located anywhere around the perimeter of the anterior region of the device so long as they extend sufficiently inward so as to be visible out from behind the iris fringe when the device is positioned in the eye. Discrete visualization features 2117 avoid narrowing the anterior opening 2127 around its full circumference providing anterior visualization without significantly impairing the user's ability to position the IOL through the anterior opening 2127 within the recess 2104 anterior to the platform 2105.

One or more components of the devices described herein may also incorporate a visual marker to provide guidance for positioning of the IOL 110 relative to the device 2100. For example, one or more markers can be located on the posterior platform 2105, an anterior-facing surface of the device, the awnings 2110, side walls 2112, or another portion of the device 2100. The markers can aid in the alignment and implantation of toric lenses relative to the device 2100. The markers can allow for intra-operative assessment of position of the device and/or the IOL 110 relative to the device 2100. One or more components of the device 2100 may be formed of materials such as silicone that are no clearly visible during evaluation using imaging techniques such as UBM. The one or more visualization markers can aid in the assessment of position of the device because the markers can be formed of a material that is visible. The markers can assist in ensuring the correct plane of the device is achieved prior to implantation of the IOL 110. The markers can assist in informing an operator of the relative position of the IOL 110 to achieve proper orientation. In some implementations, the one or more markers can be used to align a toric IOL 110 relative to the device 2100.

The devices described herein can be inserted through a corneal or scleral incision using forceps or other common ophthalmic instruments. Alternatively, the device can be inserted using an injector system similar to an intraocular lens injector. The injector allows the device to unfurl in a manner that presents portions of the device sequentially to the surgeon. Alternatively, the injector can present the full device into the anterior or posterior chamber in a configuration that limits the risk of surgical error. For instance, the injector can ensure that the device is inserted "right side up." Additionally, the injector can limit the risk of iris, endothelial, capsular, or zonular damage during implantation. The IOL 110 may be positioned within the device 2100 prior to implantation in the eye or after implantation in the eye. Similarly, the IOL 110 may be removed from the device 2100 and replaced postoperatively.

The IOL 110 can be positioned relative to the device 2100 such that it is securely fixed for proper orientation and optics. Despite being securely fixed relative to the device 2100, the IOL 110 is retrievable from the device 2100. This allows the IOL 110 to be removed and exchanged for another following implantation of the device 2100. Some patients may receive an IOL 110 during an implantation procedure that turns out to have the wrong power for proper vision. Other patients may receive a multifocal lens IOL 110 and decide later than visual quality is unsatisfactory. And still further, patient refraction may continue to drift over time. In any of these scenarios the patient may desire a new IOL. In a standard case, IOL exchange is virtually impossible because many IOLs are inserted within the capsular bag, which undergoes bag fibrosis around the lens. The device 2100 allows for easy and uncomplicated exchange of an already implanted IOL 110.

Suitable materials or combinations of materials for the preparation of the various components of the devices disclosed herein are provided throughout. It should be appreciated that other suitable materials are considered. The device can be constructed from any implant grade material that can provide the functions required of the side walls, posterior platform, the bumpers or stabilization features, and/or tethers. Materials that may be employed in this device could be but are not limited to silicone elastomer, fluorosilicone elastomer, polyurethane, hydrophilic or hydrophobic acrylics, polyolefins, nylons, PVDF, PMMA, polyimide, nitinol, titanium, stainless steel, or other implant grade materials. The device may be made from a combination of materials that are geometrically mated together, chemically bonded or welded to one another, overmolded, encapsulated, or other means for joining multiple materials. A given device element may be made of multiple materials. One or more components may be constructed from an inelastic or semi-rigid material common to ophthalmic applications such as polypropylene, Nylon, PVDF, polyimide, PMMA, polyurethane, hydrophilic or hydrophobic acrylics, or high durometer silicones. One or more components can incorporate or be formed of elastic materials such as acrylics, polyurethanes, silicone elastomers or copolymers thereof that facilitate manipulation during implantation. In still further implementations, one or more components can be formed of a semi-rigid or rigid plastic material such as polypropylene, Nylon, PVDF, polyimide, PMMA, polyurethane, hydrophilic or hydrophobic acrylics, or high durometer silicones embedded or coated with a soft, elastomeric material such as acrylics, polyurethanes, silicone elastomers or copolymers thereof. Additional materials can include PEG, HEMA, NVP, collagen or other hydrophilic biocompatible coatings, Nylon, polypropylene, Goretex, PVDF, Teflon, Nitinol, Stainless steel, silver, gold, for mechanical reinforcement and/or increased visualization. One or more of the components of the device can be formed as separate components that are coupled to one another by any of a variety of suitable methods. Alternatively, one or more components of the device can be formed as monolithic or unitary elements such as by injection or compression molding to provide relatively seamless and uninterrupted surfaces. Any of a variety of combination of materials is considered herein.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detain in order to not unnecessarily obscure the description. Reference throughout this specification to "one embodiment," "an embodiment," "one implementation, "an implementation," or the like, means that a particular feature, structure, configuration, or characteristic described is included in at least one embodiment or implementation. Thus, the appearance of the phrase "one embodiment," "an embodiment," "one implementation, "an implementation," or the like, in various placed throughout this specification are not necessarily referring to the same embodiment or implementation. Furthermore, the particular features, structures, configurations, or characteristics may be combined in any suitable manner in one or more implementations.

The devices and systems described herein can incorporate any of a variety of features. Elements or features of one implementation of a device and system described herein can be incorporated alternatively or in combination with elements or features of another implementation of a device and system described herein. For the sake of brevity, explicit descriptions of each of those combinations may be omitted although the various combinations are to be considered herein. Additionally, the devices and systems described herein can be positioned in the eye and need not be implanted specifically as shown in the figures or as described herein. The various devices can be implanted, positioned and adjusted etc. according to a variety of different methods and using a variety of different devices and systems. The various devices can be adjusted before, during as well as any time after implantation. Provided are some representative descriptions of how the various devices may be implanted and positioned, however, for the sake of brevity explicit descriptions of each method with respect to each implant or system may be omitted.

The use of relative terms throughout the description may denote a relative position or direction or orientation and is not intended to be limiting. For example, "distal" may indicate a first direction away from a reference point. Similarly, "proximal" may indicate a location in a second direction opposite to the first direction. Use of the terms "upper," "lower," "top", "bottom," "front," "side," and "back" as well as "anterior," "posterior," "caudal," "cephalad" and the like or used to establish relative frames of reference, and are not intended to limit the use or orientation of any of the devices described herein in the various implementations.

The word "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

P Embodiments

P Embodiment 1. An implantable device for supporting an intraocular lens in an eye having an anterior segment of a capsular bag, the device comprising: a posterior platform comprising an inner wall defining, at least in part, a central aperture, wherein when the device is implanted in a posterior chamber of an eye, light passes through the central aperture towards the retina; and at least one awning positioned over an anterior-facing surface of the posterior platform forming at least one recess between the awning and the posterior platform, wherein the device is configured to be deployed in the posterior chamber without trans-scleral fixation of the device.

P Embodiment 2. The device of P embodiment 1, wherein the at least one awning is adapted to mate with a perimeter of an intraocular lens or with one or more haptics of the intraocular lens.

P Embodiment 3. The device of P embodiment 1 or 2, wherein at least a portion of an intraocular lens is positioned within the at least recess.

P Embodiment 4. The device of any one of P embodiments 1-3, wherein an external surface of the at least one awning has a smooth geometry to protect the iris from the intraocular lens upon implantation of the device in the posterior chamber.

P Embodiment 5. The device of any one of P embodiments 1-3, wherein an internal surface of the at least one awning provides counter pressure to a haptic of the intraocular lens upon positioning of the intraocular lens on the device.

P Embodiment 6. A system including the device of any one of P embodiments 1-5, further comprising an intraocular lens.

P Embodiment 7. The system of P embodiment 6, wherein the intraocular lens is a one-piece intraocular lens or a multi-piece intraocular lens.

P Embodiment 8. The system of P embodiment 6 or 7, wherein the one-piece intraocular lens is selected from the group consisting of a unifocal, toric, multi-focal, extended depth of focus, and accommodating intraocular lens.

P Embodiment 9. A method of implanting the device of P embodiments 1-8, comprising: inserting the device into the posterior chamber of the eye; and positioning a one-piece intraocular lens relative to the posterior platform so at least a portion of the intraocular lens is positioned under the at least one awning.

P Embodiment 10. The method of P embodiment 9, wherein a haptic of the intraocular lens is positioned under the at least one awning.

P Embodiment 11. The method of implanting the device of P embodiment 9 or 10, wherein inserting the device into the posterior chamber of the eye comprises inserting the device without fixing the device trans-sclerally.

P Embodiment 12. The device of any one of P embodiments 1-11, wherein the posterior platform is generally ring-shaped.

P Embodiment 13. The device of any one of P embodiments 1-12, further comprising one or more stabilization features.

P Embodiment 14. The device of any one of P embodiments 1-13, wherein the one or more stabilization features comprise a plurality of bumpers projecting outward from the posterior platform providing non-penetrating contact with ciliary tissue in the eye for centration.

P Embodiment 15. The device of any one of P embodiments 1-14, wherein the posterior platform comprises an outer perimeter that is substantially non-circular and an inner perimeter that is substantially circular.

P Embodiment 16. The device of any one of P embodiments 1-15, wherein the outer perimeter is substantially rectangular and has a pair of elongate sides and a pair of short sides.

P Embodiment 17. The device of any one of P embodiments 1-16, wherein the plurality of bumpers comprises four bumpers, and wherein each of the four bumpers extend radially outward from a location where and elongate side meets a short side.

P Embodiment 18. The device of any one of P embodiments 1-17, wherein the one or more stabilization features comprise a posterior stabilization feature configured to engage with at least a portion of the capsular bag.

P Embodiment 19. The device of any one of P embodiments 1-18, wherein the posterior stabilization feature comprises a first portion projecting posteriorly from a posterior-facing surface of the posterior platform and a second portion projecting laterally outward from the first portion.

P Embodiment 20. The device of any one of P embodiments 1-13, wherein the one or more stabilization features comprises a plurality of bumpers projecting outward from the posterior platform providing non-penetrating contact with ciliary tissue in the eye for centration and comprises a posterior stabilization feature configured to engage with at least a portion of the capsular bag.

P Embodiment 21. The device of any one of P embodiments 1-20, wherein an anterior segment of the capsular bag provides support for the device along a Z-axis of the eye.

P Embodiment 22. A method for supporting an artificial intraocular lens (IOL) in an eye, the method comprising: preparing a lens support device for insertion into the eye, the lens support device comprising: a posterior platform having an anterior-facing surface and a posterior-facing surface; a central aperture extending through the posterior platform, wherein, when the lens support device is implanted in the eye light passes through the central aperture towards a retina; at least one awning projecting over at least a portion of the anterior-facing surface of the posterior platform, the at least one awning having an internal surface and an external surface, the awning forming at least one recess between the internal surface of the awning and the anterior-facing surface of the posterior platform; and bumpers projecting radially outward from the device, the bumpers having a radially-outermost portion for sutureless positioning within a posterior chamber for positioning of the lens support device in the eye; placing the lens support device posterior of the iris in the eye so the posterior-facing surface of the posterior platform is positioned anteriorly to an anterior segment of the capsular bag of the eye and without placing any portion of the device in contact with a sclera of the eye; positioning the radially outermost portion of the bumpers adjacent the sulcus to position the central aperture posterior to a pupil of the eye; positioning an optical portion of the IOL over the central aperture and anterior to at least a portion of the anterior-facing surface of the posterior platform; and positioning at least a portion of a haptic of the IOL within the at least one recessed portion to affix the IOL to the lens support device.

P Embodiment 23. A method for implanting an artificial intraocular lens (IOL) in an eye, said method comprising: creating an opening in an anterior wall of a capsular bag of said eye; preparing a lens-support device for insertion into said eye, said lens-support device comprising: a body portion comprising a central opening and a lens-support structure, said lens-support structure comprising a substantially planar lens-support surface at least partially surrounding a perimeter of said central opening, and at least one recess anterior to said lens-support surface, wherein, when said device is implanted in said eye, light passes through said central opening towards a retina; a plurality of radially extending structures coupled to said body portion, wherein each of said plurality of radially extended structures comprises a radially outermost portion for sutureless positioning of said device within a posterior chamber of said eye; and a plurality of stabilization features extending posteriorly from a posterior surface of said lens-support structure; inserting said lens-support device into said eye and posterior of an iris in said eye, such that, after insertion, no portion of said device rests in contact with a sclera of said eye; positioning said radially outermost portion of each of said plurality of structures adjacent a sulcus of the posterior chamber to stably position said central opening posterior to a pupil of said eye; inserting each of said plurality of stabilization features through said opening in said anterior wall of said capsular bag to assist in anchoring said device relative to said capsular bag; inserting an IOL into said eye; positioning an optical portion of said IOL over said central opening and anterior to at least a portion of said substantially planar lens-support surface; and positioning at least a portion of a haptic of said IOL within said at least one recess of said lens-support structure to affix the IOL to said lens-support device.

P Embodiment 24. An implantable device for supporting an intraocular lens in an eye having an anterior segment of a capsular bag, the device comprising: a posterior platform comprising an inner wall defining, at least in part, a central aperture, wherein when the device is implanted in a posterior chamber of an eye, light passes through the central optic and the central aperture towards the retina; and at least one awning positioned over an anterior-facing surface of the posterior platform forming at least one recess between the awning and the posterior platform, wherein the device is configured to be deployed without trans-scleral fixation of the device.

P Embodiment 25. The device of P embodiment 24, wherein the posterior platform further comprises one or more cut-outs peripheral to the central aperture.

P Embodiment 26. The device of P embodiments 24 or 25, wherein the posterior platform is sized and shaped to support a central optic of the intraocular lens on an anterior-facing surface of the posterior platform and the one or more cut-outs are sized and shaped to receive at least a portion of a haptic of the intraocular lens when the intraocular lens is implanted within the at least one recess of the device.

P Embodiment 27. The device of any one of P embodiments 24-26, further comprising one or more stabilization features configured to engage with at least a portion of the capsular bag.

P Embodiment 28. The device of any one of P embodiments 24-27, wherein the one or more stabilization features extend posterior to the at least one recess.

P Embodiment 29. The device of any one of P embodiments 24-28, wherein the one or more stabilization features extend anterior to the at least one recess.

P Embodiment 30. A method for implanting an artificial intraocular lens (IOL) in an eye, said method comprising: creating an opening in an anterior wall of a capsular bag of said eye; preparing a lens-support device for insertion into said eye, said lens-support device comprising: a body portion comprising a central opening, wherein, when said lens-support device is implanted in said eye, light passes through said central opening towards a retina, said body portion further comprising a lens-support surface at least partially surrounding a perimeter of said central opening, and at least one recess anterior to said lens-support surface; and at least one stabilization feature extending posteriorly from a posterior surface of said lens-support structure; inserting said lens-support device into said eye and posterior of an iris in said eye, such that, after insertion, no portion of said device rests in contact with a sclera of said eye; inserting said at least one stabilization feature through said opening in said anterior wall of said capsular bag to anchor said lens-support device relative to said capsular bag and position said central opening posterior to a pupil of said eye; inserting an IOL into said eye; positioning an optical portion of said IOL over said central opening and anterior to at least a portion of said lens-support surface; and positioning at least a portion of a haptic of said IOL within said at least one recess to secure the IOL to said lens-support device.

P Embodiment 31. The method of P embodiment 30, wherein the lens-support device further comprises a plurality of radially extending structures coupled to said body portion, wherein each of said plurality of radially extended structures comprises a radially outermost portion for sutureless positioning of said device within said eye, and wherein the method further comprises positioning said radially outermost portion of each of said plurality of radially extending structures adjacent a sulcus of the eye to prevent rotation around the visual axis and aid in centration of the device relative to said eye.

What is claimed is:

1. An implantable device for supporting an artificial intraocular lens (AIOL) in an eye, the device comprising:

a posterior platform comprising an anterior-facing surface and an inner wall defining, at least in part, a central aperture, wherein when the device is implanted in the eye and supports the AIOL, light passes through an optical portion of the AIOL and the central aperture of the posterior platform towards a retina of the eye;

at least one awning positioned over the anterior-facing surface of the posterior platform, wherein the at least one awning forms at least one recess anterior to the posterior platform, the at least one recess adapted to receive a portion of at least one haptic of the AIOL; and a plurality of radially extending structures for stabilizing the device within the eye, limiting rotation of the device within the eye after implantation and positioning of the device, and aiding in centration of the device relative to an optical axis of the eye, wherein each of the plurality of radially extending structures comprises a radially outermost portion adapted for sutureless positioning of the device within the eye by providing contact with internal structures of the eye such that when the device is implanted in the eye, the device resides posterior of an iris of the eye and no portion of the device rests external to a sclera of the eye after implantation, and wherein the posterior platform comprises an outer perimeter that is substantially non-circular and an inner perimeter that is substantially circular.

2. The device of claim 1, wherein the at least one awning positioned over the anterior-facing surface of the posterior platform defines an anterior opening.

3. The device of claim 2, wherein the at least one awning comprises a visualization feature that projects inward from the at least one awning so as to narrow a dimension of the anterior opening.

4. The device of claim 3, wherein, in use, the visualization feature is directly visualized through a pupil of the eye.

5. The device of claim 3, wherein the device has an elongate shape comprising a long axis and a short axis, wherein the dimension of the anterior opening that is narrowed is a distance between central-most edges of the anterior opening along the long axis of the device.

6. The device of claim 5, wherein the distance is at least about 5.0 mm up to about 7.0 mm.

7. The device of claim 5, wherein the visualization feature projects at least about 2.5 mm to about 3 mm away from a central axis through the central aperture.

8. The device of claim 5, wherein the distance is greater than a diameter of the central aperture.

9. The device of claim 1, wherein, during use, at least a portion of the artificial intraocular lens is positioned within the at least one recess against the anterior-facing surface.

10. The device of claim 9, wherein an external surface of the at least one awning has a smooth geometry to protect the iris from the artificial intraocular lens upon implantation of the device.

11. The device of claim 9, wherein an internal surface of the at least one awning provides counter pressure to a haptic of the artificial intraocular lens upon positioning of the artificial intraocular lens on the anterior-facing surface.

12. The device of claim 1, further comprising one or more posterior stabilization features.

13. The device of claim 12, wherein the one or more posterior stabilization features extend posteriorly from a posterior surface of the posterior platform, the one or more posterior stabilization features are configured to engage with at least a portion of a capsular bag.

14. The device of claim 13, wherein the one or more posterior stabilization features each comprises a first portion projecting posteriorly from a posterior surface of the posterior platform and a second portion projecting laterally outward from the first portion.

15. The device of claim 1, wherein the outer perimeter comprises a pair of elongate sides and a pair of short sides.

16. The device of claim 15, wherein the plurality of radially extending structures comprises four radially extending structures, and wherein each of the four radially extending structures extend radially outward from a location proximate to where one of the pair of elongate sides meets one of the pair of short sides.

17. The device of claim 1, wherein the posterior platform lies within a first plane, wherein each of the plurality of radially extending structures is coupled to the device at an angle to the first plane.

18. The device of claim 17, wherein the radially outermost portion of each of the plurality of radially extending structures is anterior of the first plane.

19. The device of claim 18, wherein the at least one awning projects anterior to the radially outermost portion.

20. The device of claim 1, wherein an anterior segment of a capsular bag provides support for the device along a Z-axis of the eye.

21. The device of claim 1, wherein the posterior platform further comprises one or more cut-outs peripheral to the central aperture.

22. The device of claim 21, wherein the posterior platform is sized and shaped to support a central optic of the artificial intraocular lens on an anterior-facing surface of the posterior platform and the one or more cut-outs are sized and shaped to receive at least a portion of a haptic of the artificial intraocular lens when the artificial intraocular lens is implanted within the at least one recess of the device.

23. The device of claim 1, further comprising one or more stabilization features configured to engage with at least a portion of a capsular bag.

24. The device of claim 23, wherein the one or more stabilization features extend posterior to the at least one recess or anterior to the at least one recess.

25. A system comprising the device of claim 1 and the AIOL.

26. The system of claim 25, wherein the device is configured to receive the AIOL forming the system before the system is implanted into the eye.

27. The system of claim 26, wherein the AIOL is a one-piece intraocular lens or a multi-piece intraocular lens.

28. The system of claim 27, wherein the one-piece intraocular lens is selected from a group consisting of a unifocal lens, a toric lens, a multi-focal lens, an extended-depth-of-focus lens, and an accommodating intraocular lens.

* * * * *